United States Patent
Simon et al.

(10) Patent No.: US 10,399,994 B2
(45) Date of Patent: *Sep. 3, 2019

(54) COMPOUNDS AND METHODS FOR PREVENTING OR TREATING SENSORY HAIR CELL DEATH

(71) Applicants: UNIVERSITY OF WASHINGTON, Seattle, WA (US); FRED HUTCHINSON CANCER RESEARCH CENTER, Seattle, WA (US); ORICULA THERAPEUTICS LLC, Seattle, WA (US)

(72) Inventors: Julian Simon, Seattle, WA (US); Graham Johnson, Sanbornton, NH (US); Edwin W. Rubel, Seattle, WA (US); David W. Raible, Seattle, WA (US); Mario D. Gonzalez, Winchester, MA (US); Peter C. Meltzer, Lexington, MA (US); Weishi Miao, Winchester, MA (US)

(73) Assignees: University of Washington, Seattle, WA (US); Oricula Therapeutics LLC, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,438

(22) PCT Filed: Feb. 5, 2016

(86) PCT No.: PCT/US2016/016880
§ 371 (c)(1),
(2) Date: Jul. 28, 2017

(87) PCT Pub. No.: WO2016/127123
PCT Pub. Date: Aug. 11, 2016

(65) Prior Publication Data
US 2018/0022756 A1 Jan. 25, 2018

Related U.S. Application Data

(60) Provisional application No. 62/113,245, filed on Feb. 6, 2015.

(51) Int. Cl.
*A61K 31/439* (2006.01)
*C07D 495/18* (2006.01)
*A61K 31/7036* (2006.01)
*A61P 27/00* (2006.01)

(52) U.S. Cl.
CPC .......... *C07D 495/18* (2013.01); *A61K 31/439* (2013.01); *A61K 31/7036* (2013.01); *A61P 27/00* (2018.01); *Y02A 50/411* (2018.01)

(58) Field of Classification Search
CPC .................................................. A61K 31/439
See application file for complete search history.

(56) References Cited

U.S. PATENT DOCUMENTS

| | | |
|---|---|---|
| 4,174,396 A | 11/1979 | Cartes et al. |
| 4,327,725 A | 5/1982 | Cortese et al. |
| 4,624,848 A | 11/1986 | Lee |
| 4,871,549 A | 10/1989 | Ueda et al. |
| 4,968,509 A | 11/1990 | Radebaugh et al. |
| 5,011,692 A | 4/1991 | Fujioka et al. |
| 5,017,381 A | 5/1991 | Maruyama et al. |
| 5,229,135 A | 7/1993 | Philippon et al. |
| 5,260,068 A | 11/1993 | Chen |
| 5,260,069 A | 11/1993 | Chen |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,686,105 A | 11/1997 | Kelm et al. |
| 5,700,410 A | 12/1997 | Nakamichi et al. |
| 5,837,284 A | 11/1998 | Mehta et al. |
| 5,840,329 A | 11/1998 | Bai |
| 5,977,175 A | 11/1999 | Lin |
| 6,465,014 B1 | 10/2002 | Moroni et al. |

(Continued)

FOREIGN PATENT DOCUMENTS

| | | |
|---|---|---|
| ES | 462993 A1 | 6/1978 |
| GB | 1582688 A | 1/1981 |

(Continued)

OTHER PUBLICATIONS

Allen et al. Transient-evoked otoacoustic emissions in children after cisplatin chemotherapy. Otolaryngol Head Neck Surg118(5):584-588 (1998).
Alvarez, et al. Benzomorphan related compounds. V. Synthesis of thienomorphans. Journal of Heterocyclic Chemistry. 1978; 15(2):193-201.
Arhin, et al. A new class of small molecule RNA polymerase inhibitors with activity against rifampicin-resistant *Staphylococcus aureus*. Bioorg Med Chem. Sep. 1, 2006;14(17):5812-32. Epub Jun. 8, 2006.
Berge, et al. Pharmaceutical salts. J Pharm Sci. Jan. 1977;66(1):1-19.
Bosch, et al. Compuestos relacionados con los benzomorfanos IX (1). Aplicacion del metodo de grewe a la sintesis de furomorfanos. Analas de Quimica. 1979; 75(5):360-365. (in Spanish with English abstract).

(Continued)

*Primary Examiner* — James D. Anderson
(74) *Attorney, Agent, or Firm* — Christensen O'Connor Johnson Kindness PLLC

(57) ABSTRACT

Disclosed herein are compounds, and pharmaceutical compositions that include such compounds, for preventing or treating hearing loss. The compounds and pharmaceutical compositions described herein prevent or treat hair cell death. In addition, the compounds and pharmaceutical compositions described herein protect against kidney damage in an individual receiving an aminoglycoside antibiotic. Methods of using the compounds, alone or in combination with other therapeutic agents, are also disclosed.

9 Claims, 4 Drawing Sheets

(56) References Cited

U.S. PATENT DOCUMENTS

| | | | |
|---|---|---|---|
| 6,932,983 | B1 | 8/2005 | Straub et al. |
| 9,493,482 | B2 | 11/2016 | Simon et al. |
| 2006/0188445 | A1 | 8/2006 | Ou et al. |
| 2015/0232476 | A1 | 8/2015 | Simon et al. |
| 2016/0229869 | A1 | 8/2016 | Simon et al. |

FOREIGN PATENT DOCUMENTS

| | | |
|---|---|---|
| WO | WO-03002569 A1 | 1/2003 |
| WO | WO-2005023818 A2 | 3/2005 |
| WO | WO-2005044008 A2 | 5/2005 |
| WO | WO-2005048948 A2 | 6/2005 |
| WO | WO-2005048948 A3 | 7/2005 |
| WO | WO-2005023818 A3 | 8/2005 |
| WO | WO-2005044008 A3 | 1/2008 |
| WO | WO-2009009550 A1 | 1/2009 |
| WO | WO-2012082331 A1 | 6/2012 |
| WO | WO-2014052914 A1 | 4/2014 |
| WO | WO-2016127123 A2 | 8/2016 |
| WO | WO-2016127123 A3 | 10/2016 |

OTHER PUBLICATIONS

Bundgaard. Design of Prodrugs. Elsevier, Amsterdam. 1985.
Claessen, et al. Quinine pharmacokinetics: ototoxic and cardiotoxic effects in healthy Caucasian subjects and in patients with falciparum malaria. Trop Med Int Health 3(6):482-489 (1998).
Devani, et al. Synthesis of 2-aminothiophenes and thieno [2, 3-D] pyrimidines. Indian Journal of Chemistry Section B—Organic Chemistry including Medicinal Chemistry. 1976; 14B(5):357-360.
Dhanireddy et al. Vestibular toxic effects induced by once-daily aminoglycoside therapy. Arch Otolaryngol Head Neck Surg 131(1):46-48 (2005).
Formann, et al. Sudden hearing loss in patients with chronic hepatitis C treated with pegylated interferon/ribavirin. Am J Gastroenterol 99(5):873-877 (2004).
Greenberg, Diuretic complications. Am J Med Sci319(1):10-24 (2000).
Higuchi, et al. Pro-drugs as Novel Delivery Systems. A.C.S. Symposium Series vol. 14 (1975).
International Preliminary Report on Patentability written opinion dated Aug. 17, 2017 for PCT Application US2016016880.
International search report and written opinion dated Aug. 25, 2016 for PCT/US2016/016880.
Liberman, et al. Pharmaceutical Dosage Forms. 2nd Ed. 1:209-214 (1990).
Matz, Clinical perspectives on ototoxic drugs. Ann Otol Rhinol Laryngol Suppl. 148:39-41 (1990).
Notice of allowance dated Jul. 6, 2016 for U.S. Appl. No. 15/017,472.
Owens, et al. Identification of genetic and chemical modulators of zebrafish mechanosensory hair cell death. PLoS Genet. Feb. 29, 2008;4(2):e1000020. doi: 10.1371/journal.pgen.1000020.
Singh, et al. Encyclopedia of Pharmaceutical Technology 2nd Ed. pp. 751-753 (2002).
Singh, et al. Encyclopedia of Pharmaceutical Technology, 2nd Ed., pp. 754-757 (2002).
Smith, et al. Controlled comparison of amikacin and gentamicin. N Engl J Med 296(7):349-353 (1977).
Theopold, Comparative surface studies of ototoxic effects of various aminoglycoside antibiotics on the organ of Corti in the guinea pig. A scanning electron microscopic study. Acta Otolaryngol84(1-2):57-64 (1977).
Toovey, et al. Audiometric changes associated with the treatment of uncomplicated falciparum malaria with co-artemether. Trans R Soc Trop Med Hyg98(5):261-267 (2004).
European search report with written opinion dated Jun. 27, 2018 for EP Application No. 16747385.

COMPOUNDS AND METHODS FOR PREVENTING OR TREATING SENSORY HAIR CELL DEATH

CROSS-REFERENCE

This application is a U.S. National Phase Application under 35 U.S.C. § 371 of International Application No. PCT/US2016/016880, filed Feb. 5, 2016, which claims the benefit of U.S. provisional application Ser. No. 62/113,245, filed Feb. 6, 2015, which are incorporated by reference in their entirety.

STATEMENT AS TO FEDERALLY SPONSORED RESEARCH

This invention was made with government support under Grants U01 NS074506, R01 DC009807, R43 DC013930, and R01 DC013688 awarded by the National Institutes of Health. The government has certain rights in the invention.

BACKGROUND

Aminoglycosides are clinically used drugs that cause dose-dependent sensorineural hearing loss (Smith et al., New Engl J Med, (1977) 296:349-53) and are known to kill hair cells in the mammalian inner ear (Theopold, Acta Otolaryngol (1977) 84:57-64). In the U.S. over 2,000,000 people receive treatment with aminoglycosides per year. The clinical efficacy of these antibiotics in treating drug-resistant bacterial infections and their low cost account for their continued worldwide use despite their known ototoxicity liability. The incidence of vestibulotoxic effects of such drugs on patient populations has been less well studied. Estimates range between 3% and 6% with continued reports in the literature of patients with aminoglycoside induced vestibulotoxicity (Dhanireddy et al., Arch Otolarngol Head Neck Surg (2005) 131:46-48). Other clinically important and commonly used drugs also have documented ototoxic effects, including cisplatin (Allen, et al, Otolaryngol Head Neck Surg (1998) 118:584-588), loop diuretics (Greenberg, Am J Med Sci, (2000) 319:10-24), antimalarial sesquiterpene lactone endoperoxides (i.e., artemesinins) (Toovey and Jamieson, Trans R Soc Trop Med Hyg (2004) 98:261-7), antimalarial quinines (Claessen, et al., Trop Med Int Health, (1998) 3:482-9), salicylates (Matz, Ann Otol Rhinol Laryngol Suppl (1990) 148:39-41), and interferon polypeptides (Formann, et al., Am J Gastroenterol (2004) 99:873-77).

BRIEF SUMMARY OF THE INVENTION

Described herein are compounds of Formula (I), Formula (Ia), Formula (Ib), Formula (II), Formula (IIa), or Formula (IIb) (hereinafter compounds of Formula (I), (Ia), (Ib), (II), (IIa), or (IIb)), pharmaceutical compositions comprising said compounds, and methods of use thereof, for preventing or treating sensory hair cell death and resulting hearing loss (ototoxicity) and loss of balance (vestibulotoxicity). In one aspect, compounds of Formula (I), (Ia), (Ib), (II), (IIa), or (IIb) prevent sensory hair cell death. In another aspect, compounds of Formula (I), (Ia), (Ib), (II), (IIa), or (IIb) treat sensory hair cell death. In another aspect, compounds of Formula (I), (Ia), (Ib), (II), (IIa), or (IIb) prevent hearing loss. In another aspect, compounds of Formula (I), (Ia), (Ib), (II), (IIa), or (IIb) treat hearing loss. In another aspect compounds of Formula (I), (Ia), (Ib), (II), (IIa), or (IIb) protect against kidney damage in an individual receiving an aminoglycoside antibiotic.

In another aspect, provided herein is a compound of Formula (I):

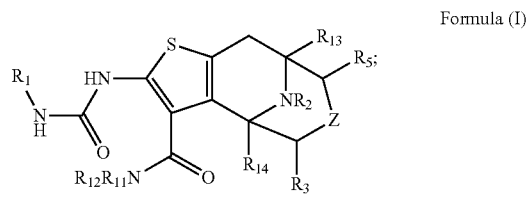

Formula (I)

wherein:

Z is a single bond, double bond, —$CH_2$—, or —O—;

$R_1$ is aryl or heteroaryl, wherein aryl and heteroaryl are optionally substituted with one or more $R_4$;

$R_2$ is H, $C_1$-$C_6$alkyl, —$C_1$-$C_6$alkyl-$OR_6$, —$C_1$-$C_6$alkyl$C_3$-$C_6$cycloalkyl, —$C_1$-$C_6$alkyl$C_2$-$C_7$heterocycloalkyl, —$C_1$-$C_6$alkyl-$CO_2R_6$, optionally substituted —$C_1$-$C_6$alkylaryl, or optionally substituted —$C_1$-$C_6$alkylheteroaryl;

$R_3$ and $R_5$ are each independently H, or $C_1$-$C_6$alkyl; or $R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring; each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;

$R_{10}$ is $C_1$-$C_6$alkyl, $C_3$-$C_6$cycloalkyl, $C_2$-$C_7$heterocycloalkyl, aryl, -heteroaryl, —$C_1$-$C_6$alkylaryl, or —$C_1$-$C_6$alkylheteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, aryl, -heteroaryl, —$C_1$-$C_6$alkyl$C_3$-$C_6$cycloalkyl, —$C_1$-$C_6$alkylaryl, or —$C_1$-$C_6$alkylheteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, -aryl, heteroaryl, —$C_1$-$C_6$alkyl$C_3$-$C_6$cycloalkyl, —$C_1$-$C_6$alkylaryl, or —$C_1$-$C_6$alkylheteroaryl; or $R_{11}$ and $R_{12}$ together with the nitrogen to which they are attached form an optionally substituted $C_2$-$C_7$heterocycloalkyl ring; and $R_{13}$ and $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In some embodiments is a compound of Formula (I) or a pharmaceutically acceptable salt, pharmaceutically acceptable solvate or hydrate, pharmaceutically acceptable salt hydrate, or pharmaceutically acceptable prodrug thereof, having the structure of Formula (Ia):

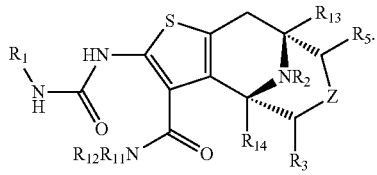

Formula (Ia)

In some embodiments is a compound of Formula (I) or a pharmaceutically acceptable salt, pharmaceutically acceptable solvate or hydrate, pharmaceutically acceptable salt hydrate, or pharmaceutically acceptable prodrug thereof, having the structure of Formula (Ib):

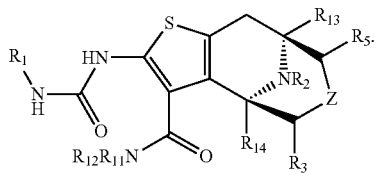

Formula (Ib)

In another embodiment is a compound of Formula (I), (Ia), or (Ib) wherein $R_1$ is aryl optionally substituted with one or more $R_4$. In another embodiment is a compound of Formula (I), (Ia), or (Ib) wherein $R_1$ is phenyl optionally substituted with one or more $R_4$. In another embodiment is a compound of Formula (I), (Ia), or (Ib) wherein $R_1$ is phenyl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In another embodiment is a compound of Formula (I), (Ia), or (Ib) wherein $R_1$ is phenyl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (I), (Ia), or (Ib) wherein $R_1$ is 4-chlorophenyl. In another embodiment is a compound of Formula (I), (Ia), or (Ib) wherein $R_{11}$ and $R_{12}$ are each H. In another embodiment is a compound of Formula (I), (Ia), or (Ib) wherein $R_2$ is H. In another embodiment is a compound of Formula (I), (Ia), or (Ib) wherein $R_2$ is $C_1$-$C_6$alkyl. In a further embodiment is a compound of Formula (I), (Ia), or (Ib) wherein $R_2$ is —CH$_3$. In another embodiment is a compound of Formula (I), (Ia), or (Ib) wherein $R_{13}$ and $R_{14}$ are each H. In another embodiment is a compound of Formula (I), (Ia), or (Ib) wherein $R_{13}$ and $R_{14}$ are each —CH$_3$. In another embodiment is a compound of Formula (I), (Ia), or (Ib) wherein $R_3$ and $R_5$ are each H. In another embodiment is a compound of Formula (I), (Ia), or (Ib) wherein Z is a single bond.

In another aspect, provided herein is a compound of Formula (II):

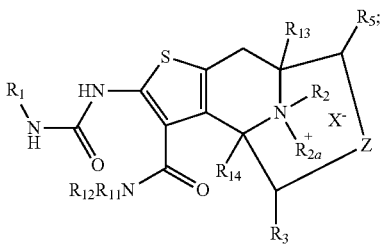

Formula (II)

wherein:

X$^-$ is a counterion;

Z is a single bond, double bond, —CH$_2$—, or —O—;

$R_1$ is aryl or heteroaryl, wherein aryl and heteroaryl are optionally substituted with one or more $R_4$;

$R_{2a}$ is $C_1$-$C_6$alkyl, —$C_1$-$C_6$alkyl-OR$_5$, or —$C_1$-$C_6$alkylC$_3$-$C_6$cycloalkyl;

$R_2$ is $C_1$-$C_6$alkyl, —$C_1$-$C_6$alkyl-OR$_6$, —$C_1$-$C_6$alkylC$_3$-$C_6$cycloalkyl, or —$C_1$-$C_6$alkyl-CO$_2$R$_6$;

$R_3$ and $R_5$ are each independently H, or $C_1$-$C_6$alkyl; or $R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring;

each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$) CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;

$R_{10}$ is $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —$C_1$-$C_6$alkylC$_3$-$C_6$cycloalkyl, —$C_1$-$C_6$alkylaryl, or —$C_1$-$C_6$alkylheteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —$C_1$-$C_6$alkylC$_3$-$C_6$cycloalkyl, —$C_1$-$C_6$alkylaryl, or —$C_1$-$C_6$alkylheteroaryl;

or $R_{11}$ and $R_{12}$ together with the nitrogen to which they are attached form an optionally substituted $C_2$-$C_7$heterocycloalkyl ring; and $R_{13}$ and $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In some embodiments is a compound of Formula (I) or a pharmaceutically acceptable salt, pharmaceutically acceptable solvate or hydrate, pharmaceutically acceptable salt hydrate, or pharmaceutically acceptable prodrug thereof, having the structure of Formula (IIa):

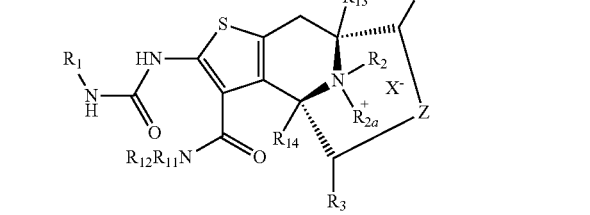

Formula (IIa)

In some embodiments is a compound of Formula (I) or a pharmaceutically acceptable salt, pharmaceutically acceptable solvate or hydrate, pharmaceutically acceptable salt hydrate, or pharmaceutically acceptable prodrug thereof, having the structure of Formula (IIb):

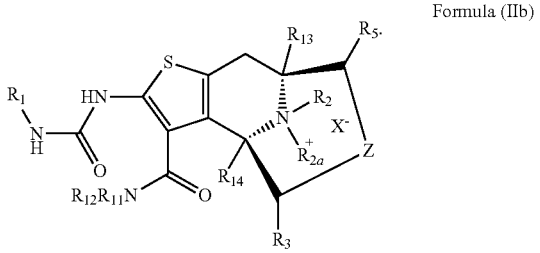

Formula (IIb)

In another embodiment is a compound of Formula (II), (IIa), or (IIb) wherein $R_1$ is aryl optionally substituted with one or more $R_4$. In another embodiment is a compound of Formula (II), (IIa), or (IIb) wherein $R_1$ is phenyl optionally substituted with one or more $R_4$. In another embodiment is a compound of Formula (II), (IIa), or (IIb) wherein $R_1$ is phenyl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In another embodiment is a compound of Formula (II), (IIa), or (IIb) wherein $R_1$ is phenyl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (II), (IIa), or (IIb) wherein $R_1$ is 4-chlorophenyl. In another embodiment is a compound of Formula (II), (IIa), or (IIb) wherein $R_{11}$ and $R_{12}$ are each H. In another embodiment is a compound of Formula (II), (IIa), or (IIb) wherein $R_2$ is —$C_1$-$C_6$alkyl-CO$_2$R$_6$. In another embodiment is a compound of Formula (II), (IIa), or (IIb) wherein $R_2$ is $C_1$-$C_6$alkyl. In a further embodiment is a compound of Formula (II), (IIa), or (IIb) wherein $R_{2a}$ is $C_1$-$C_6$alkyl. In another embodiment is a compound of Formula (II), (IIa), or (IIb) wherein $R_{13}$ and $R_{14}$ are each H. In another embodiment is a compound of Formula (II), (IIa), or (IIb) wherein $R_{13}$ and $R_{14}$ are each —CH$_3$. In another embodiment is a compound of Formula (II), (IIa), or (IIb) wherein $R_3$ and $R_5$ are each H. In another embodiment is a compound of Formula (II), (IIa), or (IIb) wherein Z is a single bond.

In another aspect is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient. In another embodiment is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic. In another embodiment is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is streptomycin. In some embodiments is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is neomycin. In some embodiments is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is amikacin. In some embodiments is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is gentamicin. In some embodiments is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is kanamycin. In some embodiments is a pharmaceutical composition comprising a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, and a pharmaceutically acceptable excipient further comprising an aminoglycoside antibiotic wherein the aminoglycoside antibiotic is tobramycin. In another embodiment of the aforementioned embodiments is a pharmaceutical composition formulated for oral, intravenous, intramuscular, or subcutaneous administration.

In another aspect is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to an ototoxic agent. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to an ototoxic agent and the ototoxic agent is an aminoglycoside antibiotic, chemotherapeutic agent, loop diuretic, antimalarial sesquiterpene lactone endoperoxide, antimalarial quinine, salicylate, or interferon polypeptide. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to an aminoglycoside antibiotic. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to an aminoglycoside antibiotic and the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to streptomycin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to neomycin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to amikacin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to gentamicin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to kanamycin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to tobramycin. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to a chemotherapeutic agent. In another embodiment is a method for preventing or treating sensory hair cell death in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the sensory hair cell death is associated with exposure to a chemotherapeutic agent and the chemotherapeutic agent is selected from cisplatin or carboplatin.

In another aspect is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to an ototoxic agent. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to an ototoxic agent and the ototoxic agent is an aminoglycoside antibiotic, chemotherapeutic agent, loop diuretic, antimalarial sesquiterpene lactone endoperoxide, antimalarial quinine, salicylate, or interferon polypeptide. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to an aminoglycoside antibiotic. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to an aminoglycoside antibiotic and the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to streptomycin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to neomycin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to amikacin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to gentamicin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to kanamycin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to tobramycin. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to a chemotherapeutic agent. In another embodiment is a method for preventing or treating hearing loss in an individual comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the hearing loss is associated with exposure to a chemotherapeutic agent and the chemotherapeutic agent is selected from cisplatin or carboplatin.

In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof. In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is streptomycin. In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is neomycin. In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is amikacin. In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is gentamicin. In another embodiment is a method for protecting against kidney damage in an individual receiving an aminoglycoside antibiotic comprising administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is kanamycin. In another embodiment is a method for protecting against kidney damage in an individual receiving an aminoglycoside antibiotic administering to the individual a therapeutically effective amount of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, wherein the aminoglycoside antibiotic is tobramycin.

In another aspect is a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof, with a maximum hair cell protection of greater than 50% in the assay described in Example 12.

In another aspect is the use of the assay described in Example 12 for the testing of a compound of Formula (I), (Ia), (Ib), (II), (IIa), or (IIb), or a pharmaceutically acceptable salt, pharmaceutically acceptable solvate or hydrate, pharmaceutically acceptable salt hydrate, or pharmaceutically acceptable prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
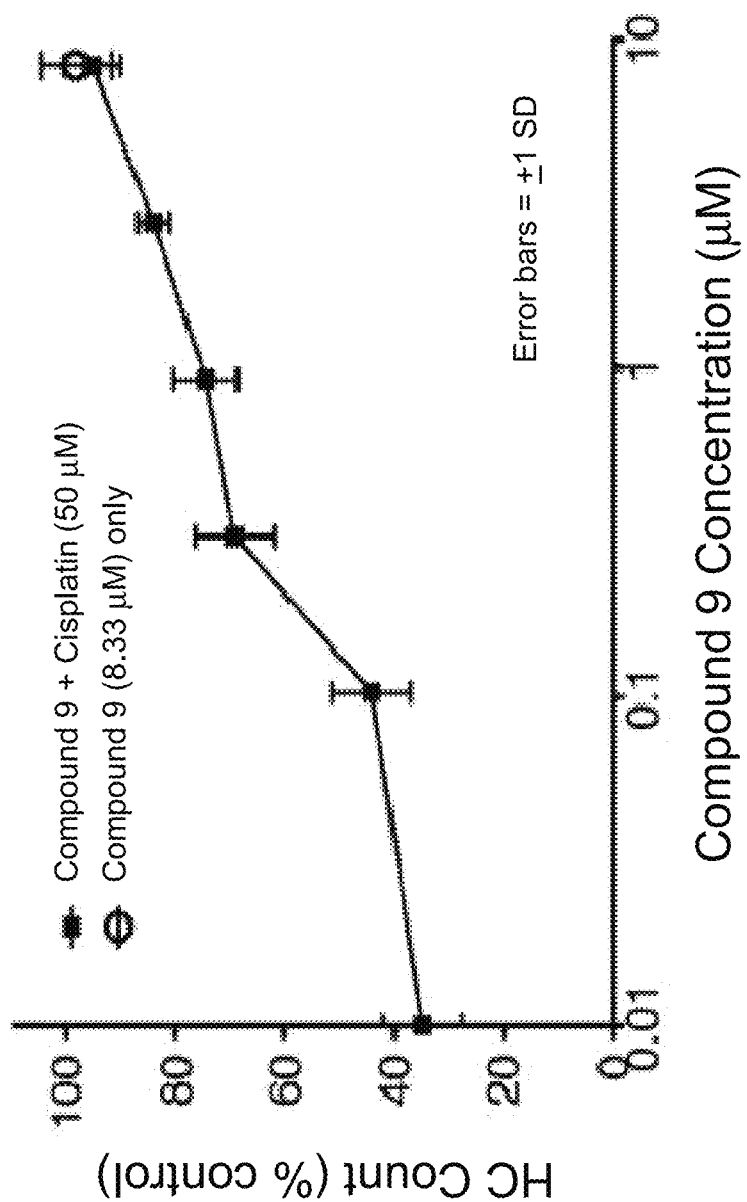
FIG. 1 shows the effect in the zebrafish hair cell toxicity assay following treatment with cisplatin plus compound 9.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to six carbon atoms (e.g., $C_2$-$C_6$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —OC(O)—N($R^a)_2$, —N($R^a$)C(O)$R^a$, —N($R^a$)S(O)$_t R^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl. Depending on the structure, an alkyl group is optionally a monoradical or a diradical (i.e. an alkylene group).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group is optionally through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heterocycloalkylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl may be saturated, (i.e., containing single C—C bonds only) or partially unsaturated. Examples of monocyclic cycloalkyls include, e.g., cyclopropyl, cyclobutyl, cyclopentyl, cyclohexyl, cycloheptyl, and cyclooctyl. An unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Cycloalkylalkyl" refers to a radical of the formula —R$^c$-cycloalkyl where R$^c$ is an alkylene chain as defined above. The alkylene chain and the cycloalkyl radical is optionally substituted as defined above.

"Cycloalkylalkoxy" refers to a radical bonded through an oxygen atom of the formula —O—R$^c$-cycloalkyl where R$^c$ is an alkylene chain as defined above. The alkylene chain and the cycloalkyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocycloalkyl" or "N-attached heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals.

Examples of such N-heterocycloalkyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocycloalkyl" or "C-attached heterocycloalkyl" refers to a heterocycloalkyl radical as defined above containing at least one heteroatom and where the point of attachment of the heterocycloalkyl radical to the rest of the molecule is through a carbon atom in the heterocycloalkyl radical. A C-heterocycloalkyl radical is optionally substituted as described above for heterocycloalkyl radicals. Examples of such C-heterocycloalkyl radicals include, but are not limited to, 2-morpholinyl, 2- or 3- or 4-piperidinyl, 2-piperazinyl, 2- or 3-pyrrolidinyl, and the like.

"Heterocycloalkylalkyl" refers to a radical of the formula —$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkyl radical is optionally substituted as defined above for an alkylene chain. The heterocycloalkyl part of the heterocycloalkylalkyl radical is optionally substituted as defined above for a heterocycloalkyl group.

"Heterocycloalkylalkoxy" refers to a radical bonded through an oxygen atom of the formula —O—$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkoxy radical is optionally substituted as defined above for an alkylene chain. The heterocycloalkyl part of the heterocycloalkylalkoxy radical is optionally substituted as defined above for a heterocycloalkyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

way of example, an optional substituents may be $L^s R^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —(C$_1$-C$_6$alkyl)-, or —(C$_2$-C$_6$alkenyl)-; and each $R^s$ is independently selected from among H, (C$_1$-C$_6$alkyl), (C$_3$-C$_8$cycloalkyl), aryl, heteroaryl, heterocycloalkyl, and C$_1$-C$_6$heteroalkyl. The protecting groups that may form the protective derivatives of the above substituents are found in sources such as Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric

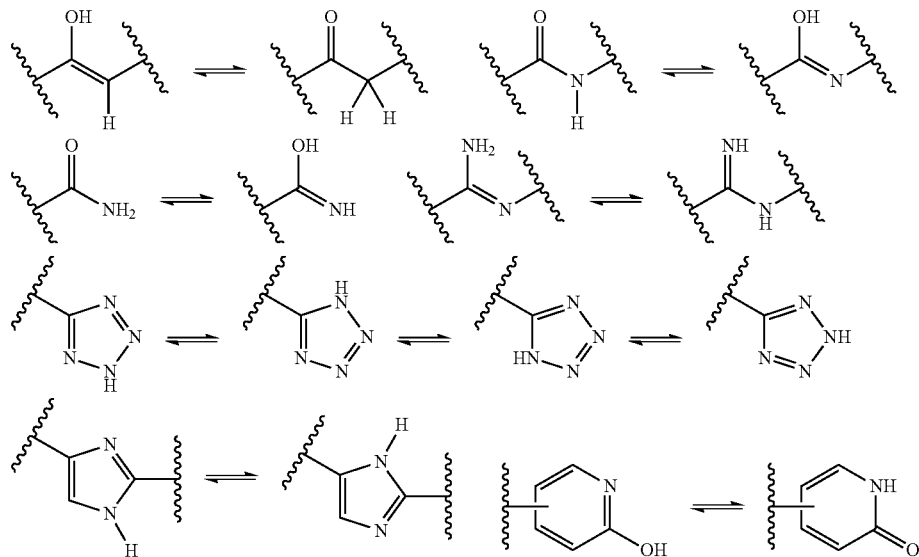

"Optional" or "optionally" means that a subsequently described event or circumstance may or may not occur and that the description includes instances when the event or circumstance occurs and instances in which it does not.

"Optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, C$_1$-C$_6$alkylalkyne, halo, acyl, acyloxy, —CO$_2$H, —CO$_2$-alkyl, nitro, haloalkyl, fluoroalkyl, and amino, including mono- and di-substituted amino groups (e.g. —NH$_2$, —NHR, —N(R)$_2$), and the protected derivatives thereof. By acid, nitric acid, phosphoric acid, hydroiodic acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, pyroglutamic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to known methods and techniques.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Counterion" refers to an ion that accompanies an ionic species in order to maintain electric neutrality. Examples of counterions include, but are not limited to, Cl⁻, Br⁻, I⁻, and $CF_3CO_2^-$.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

In some embodiments, the compounds, and compositions comprising these compounds, described herein are useful for preventing or treating sensory hair cell death. In some embodiments, the compounds, and compositions comprising these compounds, described herein are useful for preventing or treating hearing loss. In some embodiments, the compounds, and compositions comprising these compounds, described herein are useful for protecting against kidney damage in an individual receiving an aminoglycoside antibiotic.

In one embodiment is a compound of Formula (I):

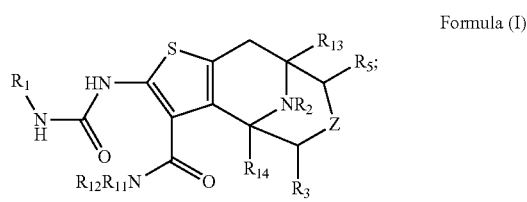

Formula (I)

wherein:
Z is a single bond, double bond, —$CH_2$—, or —O—;
$R_1$ is aryl or heteroaryl, wherein aryl and heteroaryl are optionally substituted with one or more $R_4$;
$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl;
$R_3$ and $R_5$ are each independently H, or $C_1$-$C_6$alkyl; or
$R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring;
each $R_4$ is independently selected from F, Cl, Br, I, —CN, —$NO_2$, —$CF_3$, —$OR_9$, —$OCF_3$, —$NR_8R_9$, —C(O)$R_{10}$, —$CO_2R_9$, —C(O)$NR_8R_9$, —N($R_8$)C(O)$R_{10}$, —N($R_8$)$CO_2R_{10}$, —NHS(O)$_2R_{10}$, —S(O)$_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl;

$R_{10}$ is $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, $C_1$-$C_6$alkyl$C_3$-$C_6$cycloalkyl, $C_1$-$C_6$alkylaryl, or $C_1$-$C_6$alkylheteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, $C_1$-$C_6$alkyl$C_3$-$C_6$cycloalkyl, $C_1$-$C_6$alkylaryl, or $C_1$-$C_6$alkylheteroaryl; or $R_{11}$ and $R_{12}$ together with the nitrogen to which they are attached form an optionally substituted $C_2$-$C_7$heterocycloalkyl ring; and $R_{13}$ and $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (I), wherein $R_1$ is aryl optionally substituted with one or more $R_4$. In another embodiment is a compound of Formula (I), wherein $R_1$ is phenyl optionally substituted with one or more $R_4$. In another embodiment is a compound of Formula (I), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —C(O)$R_{10}$, —$CO_2R_9$, $C_1$-$C_6$alkyl, and $C_1$-$C_6$haloalkyl. In another embodiment is a compound of Formula (I), wherein $R_1$ is phenyl substituted with one or more $R_4$, wherein each $R_4$ is independently selected F, Cl, Br, I, —CN, —$CF_3$, —$OR_9$, —$OCF_3$, —C(O)$R_{10}$, —$CO_2R_9$, and $C_1$-$C_6$alkyl. In another embodiment is a compound of Formula (I), wherein $R_1$ is 4-chlorophenyl.

In another embodiment is a compound of Formula (I) wherein $R_1$ is heteroaryl optionally substituted with one or more $R_4$. In another embodiment is a compound of Formula (I), wherein $R_1$ is heteroaryl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —C(O)$R_{10}$, —$CO_2R_9$, $C_1$-$C_6$alkyl, and $C_1$-$C_6$haloalkyl. In another embodiment is a compound of Formula (I), wherein $R_1$ is heteroaryl substituted with one or more $R_4$, wherein each $R_4$ is independently selected F, Cl, Br, I, —CN, —$CF_3$, —$OR_9$, —$OCF_3$, —C(O)$R_{10}$, —$CO_2R_9$, and $C_1$-$C_6$alkyl. In another embodiment is a compound of Formula (I), wherein heteroaryl is pyridyl.

In another embodiment is a compound of Formula (I) wherein $R_{11}$ and $R_{12}$ are each $C_1$-$C_6$alkyl. In another embodiment is a compound of Formula (I) wherein $R_{11}$ and $R_{12}$ are each —$CH_3$. In another embodiment is a compound of Formula (I) wherein $R_{11}$ is H and $R_{12}$ is $C_1$-$C_6$alkyl. In another embodiment is a compound of Formula (I) wherein $R_{11}$ is H and $R_{12}$ is —$CH_3$. In another embodiment is a compound of Formula (I) wherein $R_{11}$ is H and $R_{12}$ is $C_3$-$C_6$cycloalkyl. In another embodiment is a compound of Formula (I) wherein $R_{11}$ is H and $R_{12}$ is $C_1$-$C_6$alkyl$C_3$-$C_6$cycloalkyl. In another embodiment is a compound of Formula (I) wherein $R_{11}$ is H and $R_{12}$ is $C_1$-$C_6$alkylaryl. In another embodiment is a compound of Formula (I) wherein $R_{11}$ is H and $R_{12}$ is $C_1$-$C_6$alkylheteroaryl.

In another embodiment is a compound of Formula (I) wherein $R_{13}$ and $R_{14}$ are each H. In another embodiment is a compound of Formula (I) wherein $R_{13}$ and $R_{14}$ are each —$CH_3$.

In another embodiment is a compound of Formula (I) wherein $R_3$ and $R_5$ are each H. In another embodiment is a compound of Formula (I) wherein $R_3$ and $R_5$ are each —$CH_3$.

In another embodiment is a compound of Formula (I) wherein $R_{11}$ and $R_{12}$ are each H.

In another embodiment is a compound of Formula (I), wherein $R_2$ is H. In another embodiment is a compound of Formula (I), wherein $R_2$ is $C_1$-$C_6$alkyl. In a further embodiment is a compound of Formula (I), wherein $R_2$ is —$CH_3$. In another embodiment is a compound of Formula (I), wherein $R_2$ is —$CH_2CH_3$. In another embodiment is a compound of Formula (I), wherein $R_2$ is $C_1$-$C_6$alkyl-$OR_6$. In another embodiment is a compound of Formula (I), wherein $R_2$ is $C_1$-$C_6$alkyl-OH. In another embodiment is a compound of Formula (I), wherein $R_2$ is $C_1$-$C_6$alkyl$C_3$-$C_6$cycloalkyl. In another embodiment is a compound of Formula (I), wherein $R_2$ is —$CH_2$—$C_3$-$C_6$cycloalkyl. In another embodiment is a compound of Formula (I), wherein $R_2$ is —$CH_2$— cyclopropyl. In another embodiment is a compound of Formula (I), wherein $R_2$ is —$CH_2$-cyclobutyl. In another embodiment is a compound of Formula (I), wherein $R_2$ is —$CH_2$-cyclopentyl. In another embodiment is a compound of Formula (I), wherein $R_2$ is —$CH_2$-cyclohexyl. In another embodiment is a compound of Formula (I), wherein $R_2$ is $C_1$-$C_6$alkyl$C_2$-$C_7$heterocycloalkyl. In another embodiment is a compound of Formula (I), wherein $R_2$ is —$CH_2$—$C_2$-$C_7$heterocycloalkyl. In another embodiment is a compound of Formula (I), wherein $R_2$ is $C_1$-$C_6$alkyl-$CO_2R_6$. In another embodiment is a compound of Formula (I), wherein $R_2$ is $C_1$-$C_6$alkyl-$CO_2CH_3$. In another embodiment is a compound of Formula (I), wherein $R_2$ is $C_1$-$C_6$alkyl-$CO_2CH_2CH_3$. In another embodiment is a compound of Formula (I), wherein $R_2$ is optionally substituted $C_1$-$C_6$alkylaryl. In another embodiment is a compound of Formula (I), wherein $R_2$ is optionally substituted $C_1$-$C_6$alkylheteroaryl.

In another embodiment is a compound of Formula (I), wherein Z is a single bond. In another embodiment is a compound of Formula (I), wherein Z is a double bond. In another embodiment is a compound of Formula (I), wherein Z is —$CH_2$—. In another embodiment is a compound of Formula (I), wherein Z is —O—.

In another embodiment is a compound of Formula (I), having the structure of Formula (I'):

Formula (I')

wherein:

$R_1$ is aryl or heteroaryl, wherein aryl and heteroaryl are optionally substituted with one or more $R_4$;

$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl;

each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, C$_1$-C$_6$alkyl, C$_3$-C$_6$cycloalkyl, C$_1$-C$_6$heteroalkyl, C$_1$-C$_6$haloalkyl, C$_2$-C$_7$heterocycloalkyl, aryl, and heteroaryl;

$R_6$ is H, or C$_1$-C$_6$alkyl;

$R_8$ is H, or C$_1$-C$_6$alkyl;

$R_9$ is H, C$_1$-C$_6$alkyl, C$_3$-C$_6$cycloalkyl, C$_2$-C$_7$heterocycloalkyl, aryl, heteroaryl, C$_1$-C$_6$alkylaryl, or C$_1$-C$_6$alkylheteroaryl; and $R_{10}$ is C$_1$-C$_6$alkyl, C$_3$-C$_6$cycloalkyl, C$_2$-C$_7$heterocycloalkyl, aryl, heteroaryl, C$_1$-C$_6$alkylaryl, or C$_1$-C$_6$alkylheteroaryl;

or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (I'), wherein $R_1$ is aryl optionally substituted with one or more $R_4$. In another embodiment is a compound of Formula (I'), wherein $R_1$ is phenyl optionally substituted with one or more $R_4$. In another embodiment is a compound of Formula (I'), wherein $R_1$ is phenyl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (I'), wherein $R_1$ is phenyl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (I'), wherein $R_1$ is 4-chlorophenyl.

In another embodiment is a compound of Formula (I') wherein $R_1$ is heteroaryl optionally substituted with one or more $R_4$. In another embodiment is a compound of Formula (I'), wherein $R_1$ is heteroaryl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (I'), wherein $R_1$ is heteroaryl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (I'), wherein heteroaryl is pyridyl.

In another embodiment is a compound of Formula (I'), wherein $R_2$ is H. In another embodiment is a compound of Formula (I'), wherein $R_2$ is C$_1$-C$_6$alkyl. In a further embodiment is a compound of Formula (I'), wherein $R_2$ is —CH$_3$. In another embodiment is a compound of Formula (I'), wherein $R_2$ is —CH$_2$CH$_3$. In another embodiment is a compound of Formula (I'), wherein $R_2$ is C$_1$-C$_6$alkyl-OR$_6$. In another embodiment is a compound of Formula (I'), wherein $R_2$ is C$_1$-C$_6$alkyl-OH. In another embodiment is a compound of Formula (I'), wherein $R_2$ is C$_1$-C$_6$alkylC$_3$-C$_6$cycloalkyl. In another embodiment is a compound of Formula (I'), wherein $R_2$ is —CH$_2$—C$_3$-C$_6$cycloalkyl. In another embodiment is a compound of Formula (I'), wherein $R_2$ is —CH$_2$— cyclopropyl. In another embodiment is a compound of Formula (I'), wherein $R_2$ is —CH$_2$— cyclobutyl. In another embodiment is a compound of Formula (I'), wherein $R_2$ is —CH$_2$-cyclopentyl. In another embodiment is a compound of Formula (I'), wherein $R_2$ is —CH$_2$-cyclohexyl. In another embodiment is a compound of Formula (I'), wherein $R_2$ is C$_1$-C$_6$alkylC$_2$-C$_7$heterocycloalkyl. In another embodiment is a compound of Formula (I'), wherein $R_2$ is —CH$_2$—C$_2$-C$_7$heterocycloalkyl. In another embodiment is a compound of Formula (I'), wherein $R_2$ is C$_1$-C$_6$alkyl-CO$_2$R$_6$. In another embodiment is a compound of Formula (I'), wherein $R_2$ is C$_1$-C$_6$alkyl-CO$_2$CH$_3$. In another embodiment is a compound of Formula (I'), wherein $R_2$ is C$_1$-C$_6$alkyl-CO$_2$CH$_2$CH$_3$. In another embodiment is a compound of Formula (I'), wherein $R_2$ is optionally substituted C$_1$-C$_6$alkylaryl. In another embodiment is a compound of Formula (I'), wherein $R_2$ is optionally substituted C$_1$-C$_6$alkylheteroaryl.

In another embodiment is a compound of Formula (I), having the structure of Formula (I''):

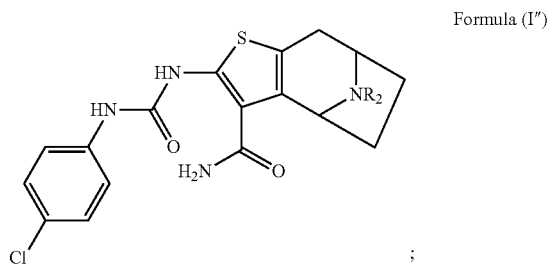

Formula (I'')

wherein:

$R_2$ is H, C$_1$-C$_6$alkyl, C$_1$-C$_6$alkyl-OR$_6$, C$_1$-C$_6$alkylC$_3$-C$_6$cycloalkyl, C$_1$-C$_6$alkylC$_2$-C$_7$heterocycloalkyl, C$_1$-C$_6$alkyl-CO$_2$R$_6$, optionally substituted C$_1$-C$_6$alkylaryl, or optionally substituted C$_1$-C$_6$alkylheteroaryl; and $R_6$ is H, or C$_1$-C$_6$alkyl;

or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (I''), wherein $R_2$ is H. In another embodiment is a compound of Formula (I''), wherein $R_2$ is C$_1$-C$_6$alkyl. In a further embodiment is a compound of Formula (I''), wherein $R_2$ is —CH$_3$. In another embodiment is a compound of Formula (I''), wherein $R_2$ is —CH$_2$CH$_3$. In another embodiment is a compound of Formula (I''), wherein $R_2$ is C$_1$-C$_6$alkyl-OR$_6$. In another embodiment is a compound of Formula (I''), wherein $R_2$ is C$_1$-C$_6$alkyl-OH. In another embodiment is a compound of Formula (I''), wherein $R_2$ is C$_1$-C$_6$alkylC$_3$-C$_6$cycloalkyl. In another embodiment is a compound of Formula (I''), wherein $R_2$ is —CH$_2$—C$_3$-C$_6$cycloalkyl. In another embodiment is a compound of Formula (I''), wherein $R_2$ is —CH$_2$— cyclopropyl. In another embodiment is a compound of Formula (I''), wherein $R_2$ is —CH$_2$— cyclobutyl. In another embodiment is a compound of Formula (I''), wherein $R_2$ is —CH$_2$— cyclopentyl. In another embodiment is a compound of Formula (I''), wherein $R_2$ is —CH$_2$— cyclohexyl. In another embodiment is a compound of Formula (I''), wherein $R_2$ is C$_1$-C$_6$alkylC$_2$-C$_7$heterocycloalkyl. In another embodiment is a compound of Formula (I''), wherein $R_2$ is —CH$_2$—C$_2$-C$_7$heterocycloalkyl. In another embodiment is a compound of Formula (I''), wherein $R_2$ is C$_1$-C$_6$alkyl-CO$_2$R$_6$. In another embodiment is a compound of Formula (I''), wherein $R_2$ is C$_1$-C$_6$alkyl-CO$_2$CH$_3$. In another embodiment is a compound of Formula (I''), wherein $R_2$ is C$_1$-C$_6$alkyl-CO$_2$CH$_2$CH$_3$. In another embodiment is a compound of Formula (I''), wherein $R_2$ is optionally substituted C$_1$-C$_6$alkylaryl. In another embodiment is a compound of Formula (I''), wherein $R_2$ is optionally substituted C$_1$-C$_6$alkylheteroaryl.

In another embodiment is a compound of Formula (Ia):

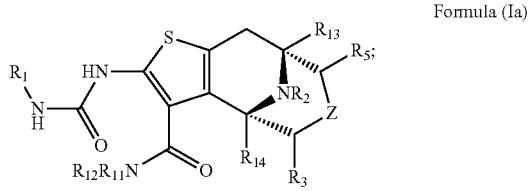

Formula (Ia)

wherein:
Z is a single bond, double bond, —CH$_2$—, or —O—;
R$_1$ is aryl or heteroaryl, wherein aryl and heteroaryl are optionally substituted with one or more R$_4$;
R$_2$ is H, C$_1$-C$_6$alkyl, C$_1$-C$_6$alkyl-OR$_6$, C$_1$-C$_6$alkylC$_3$-C$_6$cycloalkyl, C$_1$-C$_6$alkylC$_2$-C$_7$heterocycloalkyl, C$_1$-C$_6$alkyl-CO$_2$R$_6$, optionally substituted C$_1$-C$_6$alkylaryl, or optionally substituted C$_1$-C$_6$alkylheteroaryl;
R$_3$ and R$_5$ are each independently H, or C$_1$-C$_6$alkyl; or
R$_3$ and R$_5$ together form an optionally substituted C$_3$-C$_6$cycloalkyl ring, optionally substituted C$_2$-C$_7$heterocycloalkyl ring, optionally substituted aryl ring, or an optionally substituted heteroaryl ring;
each R$_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, C$_1$-C$_6$alkyl, C$_3$-C$_6$cycloalkyl, C$_1$-C$_6$heteroalkyl, C$_1$-C$_6$haloalkyl, C$_2$-C$_7$heterocycloalkyl, aryl, and heteroaryl;
R$_6$ is H, or C$_1$-C$_6$alkyl;
R$_8$ is H, or C$_1$-C$_6$alkyl;
R$_9$ is H, C$_1$-C$_6$alkyl, C$_3$-C$_6$cycloalkyl, C$_2$-C$_7$heterocycloalkyl, aryl, heteroaryl, C$_1$-C$_6$alkylaryl, or C$_1$-C$_6$alkylheteroaryl;
R$_{10}$ is C$_1$-C$_6$alkyl, C$_3$-C$_6$cycloalkyl, C$_2$-C$_7$heterocycloalkyl, aryl, heteroaryl, C$_1$-C$_6$alkylaryl, or C$_1$-C$_6$alkylheteroaryl;
R$_{11}$ is H, C$_1$-C$_6$alkyl, C$_1$-C$_6$haloalkyl, C$_3$-C$_6$cycloalkyl, C$_2$-C$_7$heterocycloalkyl, aryl, heteroaryl, C$_1$-C$_6$alkylC$_3$-C$_6$cycloalkyl, C$_1$-C$_6$alkylaryl, or C$_1$-C$_6$alkylheteroaryl;
R$_{12}$ is H, C$_1$-C$_6$alkyl, C$_1$-C$_6$haloalkyl, C$_3$-C$_6$cycloalkyl, C$_2$-C$_7$heterocycloalkyl, aryl, heteroaryl, C$_1$-C$_6$alkylC$_3$-C$_6$cycloalkyl, C$_1$-C$_6$alkylaryl, or C$_1$-C$_6$alkylheteroaryl; or
R$_{11}$ and R$_{12}$ together with the nitrogen to which they are attached form an optionally substituted C$_2$-C$_7$heterocycloalkyl ring; and
R$_{13}$ and R$_{14}$ are each independently H, or C$_1$-C$_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (Ia), wherein R$_1$ is aryl optionally substituted with one or more R$_4$. In another embodiment is a compound of Formula (Ia), wherein R$_1$ is phenyl optionally substituted with one or more R$_4$. In another embodiment is a compound of Formula (Ia), wherein R$_1$ is phenyl substituted with one or more R$_4$, wherein each R$_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (Ia), wherein R$_1$ is phenyl substituted with one or more R$_4$, wherein each R$_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (Ia), wherein R$_1$ is 4-chlorophenyl.

In another embodiment is a compound of Formula (Ia) wherein R$_1$ is heteroaryl optionally substituted with one or more R$_4$. In another embodiment is a compound of Formula (Ia), wherein R$_1$ is heteroaryl substituted with one or more R$_4$, wherein each R$_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (Ia), wherein R$_1$ is heteroaryl substituted with one or more R$_4$, wherein each R$_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (Ia), wherein heteroaryl is pyridyl.

In another embodiment is a compound of Formula (Ia) wherein R$_{11}$ and R$_{12}$ are each C$_1$-C$_6$alkyl. In another embodiment is a compound of Formula (Ia) wherein R$_{11}$ and R$_{12}$ are each —CH$_3$. In another embodiment is a compound of Formula (Ia) wherein R$_{11}$ is H and R$_{12}$ is C$_1$-C$_6$alkyl. In another embodiment is a compound of Formula (Ia) wherein R$_{11}$ is H and R$_{12}$ is —CH$_3$. In another embodiment is a compound of Formula (Ia) wherein R$_{11}$ is H and R$_{12}$ is C$_3$-C$_6$cycloalkyl. In another embodiment is a compound of Formula (Ia) wherein R$_{11}$ is H and R$_{12}$ is C$_1$-C$_6$alkylC$_3$-C$_6$cycloalkyl. In another embodiment is a compound of Formula (Ia) wherein R$_{11}$ is H and R$_{12}$ is C$_1$-C$_6$alkylaryl. In another embodiment is a compound of Formula (Ia) wherein R$_{11}$ is H and R$_{12}$ is C$_1$-C$_6$alkylheteroaryl.

In another embodiment is a compound of Formula (Ia) wherein R$_{13}$ and R$_{14}$ are each H. In another embodiment is a compound of Formula (Ia) wherein R$_{13}$ and R$_{14}$ are each —CH$_3$.

In another embodiment is a compound of Formula (Ia) wherein R$_3$ and R$_5$ are each H. In another embodiment is a compound of Formula (Ia) wherein R$_3$ and R$_5$ are each —CH$_3$.

In another embodiment is a compound of Formula (Ia) wherein R$_{11}$ and R$_{12}$ are each H.

In another embodiment is a compound of Formula (Ia), wherein R$_2$ is H. In another embodiment is a compound of Formula (Ia), wherein R$_2$ is C$_1$-C$_6$alkyl. In a further embodiment is a compound of Formula (Ia), wherein R$_2$ is —CH$_3$. In another embodiment is a compound of Formula (Ia), wherein R$_2$ is —CH$_2$CH$_3$. In another embodiment is a compound of Formula (Ia), wherein R$_2$ is C$_1$-C$_6$alkyl-OR$_6$. In another embodiment is a compound of Formula (Ia), wherein R$_2$ is C$_1$-C$_6$alkyl-OH. In another embodiment is a compound of Formula (Ia), wherein R$_2$ is C$_1$-C$_6$alkylC$_3$-C$_6$cycloalkyl. In another embodiment is a compound of Formula (Ia), wherein R$_2$ is —CH$_2$—C$_3$-C$_6$cycloalkyl. In another embodiment is a compound of Formula (Ia), wherein R$_2$ is —CH$_2$— cyclopropyl. In another embodiment is a compound of Formula (Ia), wherein R$_2$ is —CH$_2$— cyclobutyl. In another embodiment is a compound of Formula (Ia), wherein R$_2$ is —CH$_2$— cyclopentyl. In another embodiment is a compound of Formula (Ia), wherein R$_2$ is —CH$_2$— cyclohexyl. In another embodiment is a compound of Formula (Ia), wherein R$_2$ is C$_1$-C$_6$alkylC$_2$-C$_7$heterocycloalkyl. In another embodiment is a compound of Formula (Ia), wherein R$_2$ is —CH$_2$—C$_2$-C$_7$heterocycloalkyl. In another embodiment is a compound of Formula (Ia), wherein R$_2$ is C$_1$-C$_6$alkyl-CO$_2$R$_6$. In another embodiment is a compound of Formula (Ia), wherein R$_2$ is C$_1$-C$_6$alkyl-CO$_2$CH$_3$. In another embodiment is a compound of Formula (Ia), wherein R$_2$ is C$_1$-C$_6$alkyl-CO$_2$CH$_2$CH$_3$. In another embodiment is a compound of Formula (Ia), wherein R$_2$ is optionally substituted $C_1$-$C_6$alkylaryl. In another embodiment is a compound of Formula (Ia), wherein $R_2$ is optionally substituted $C_1$-$C_6$alkylheteroaryl.

In another embodiment is a compound of Formula (Ia), wherein Z is a single bond. In another embodiment is a compound of Formula (Ia), wherein Z is a double bond. In another embodiment is a compound of Formula (Ia), wherein Z is —$CH_2$—. In another embodiment is a compound of Formula (Ia), wherein Z is —O—.

In another embodiment is a compound of Formula (Ia), having the structure of Formula (Ia'):

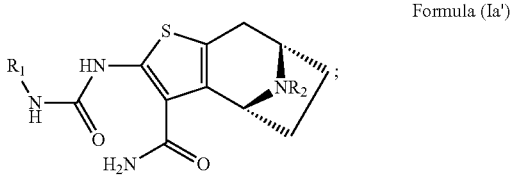

Formula (Ia')

wherein:
$R_1$ is aryl or heteroaryl, wherein aryl and heteroaryl are optionally substituted with one or more $R_4$;
$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl;
each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl; and
$R_{10}$ is $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (Ia'), wherein $R_1$ is aryl optionally substituted with one or more $R_4$. In another embodiment is a compound of Formula (Ia'), wherein $R_1$ is phenyl optionally substituted with one or more $R_4$. In another embodiment is a compound of Formula (Ia'), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (Ia'), wherein $R_1$ is phenyl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (Ia'), wherein $R_1$ is 4-chlorophenyl.

In another embodiment is a compound of Formula (Ia') wherein $R_1$ is heteroaryl optionally substituted with one or more $R_4$. In another embodiment is a compound of Formula (Ia'), wherein $R_1$ is heteroaryl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (Ia'), wherein $R_1$ is heteroaryl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (Ia'), wherein heteroaryl is pyridyl.

In another embodiment is a compound of Formula (Ia'), wherein $R_2$ is H. In another embodiment is a compound of Formula (Ia'), wherein $R_2$ is $C_1$-$C_6$alkyl. In a further embodiment is a compound of Formula (Ia'), wherein $R_2$ is —$CH_3$. In another embodiment is a compound of Formula (Ia'), wherein $R_2$ is —$CH_2CH_3$. In another embodiment is a compound of Formula (Ia'), wherein $R_2$ is $C_1$-$C_6$alkyl-$OR_6$. In another embodiment is a compound of Formula (Ia'), wherein $R_2$ is $C_1$-$C_6$alkyl-OH. In another embodiment is a compound of Formula (Ia'), wherein $R_2$ is $C_1$-$C_6$alkyl$C_3$-$C_6$cycloalkyl. In another embodiment is a compound of Formula (Ia'), wherein $R_2$ is —$CH_2$—$C_3$-$C_6$cycloalkyl. In another embodiment is a compound of Formula (Ia'), wherein $R_2$ is —$CH_2$— cyclopropyl. In another embodiment is a compound of Formula (Ia'), wherein $R_2$ is —$CH_2$— cyclobutyl. In another embodiment is a compound of Formula (Ia'), wherein $R_2$ is —$CH_2$— cyclopentyl. In another embodiment is a compound of Formula (Ia'), wherein $R_2$ is —$CH_2$— cyclohexyl. In another embodiment is a compound of Formula (Ia'), wherein $R_2$ is $C_1$-$C_6$alkyl$C_2$-$C_7$heterocycloalkyl. In another embodiment is a compound of Formula (Ia'), wherein $R_2$ is —$CH_2$—$C_2$-$C_7$heterocycloalkyl. In another embodiment is a compound of Formula (Ia'), wherein $R_2$ is $C_1$-$C_6$alkyl-$CO_2R_6$. In another embodiment is a compound of Formula (Ia'), wherein $R_2$ is $C_1$-$C_6$alkyl-$CO_2CH_3$. In another embodiment is a compound of Formula (Ia'), wherein $R_2$ is $C_1$-$C_6$alkyl-$CO_2CH_2CH_3$. In another embodiment is a compound of Formula (Ia'), wherein $R_2$ is optionally substituted $C_1$-$C_6$alkylaryl. In another embodiment is a compound of Formula (Ia'), wherein $R_2$ is optionally substituted $C_1$-$C_6$alkylheteroaryl.

In another embodiment is a compound of Formula (Ia), having the structure of Formula (Ia"):

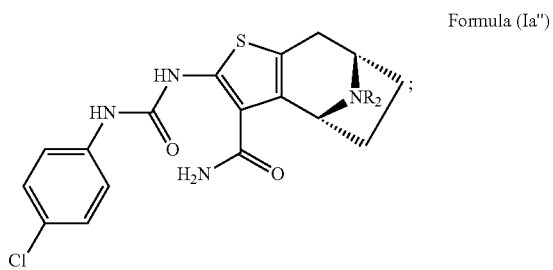

Formula (Ia")

wherein:
$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl; and
$R_6$ is H, or $C_1$-$C_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (Ia"), wherein $R_2$ is H. In another embodiment is a compound of Formula (Ia"), wherein $R_2$ is $C_1$-$C_6$alkyl. In a further embodiment is a compound of Formula (Ia"), wherein $R_2$ is —$CH_3$. In another embodiment is a compound of Formula (Ia"), wherein $R_2$ is —$CH_2CH_3$. In another embodiment is a compound of Formula (Ia"), wherein $R_2$ is $C_1$-$C_6$alkyl-$OR_6$. In another embodiment is a compound of Formula (Ia"), wherein $R_2$ is $C_1$-$C_6$alkyl-OH. In another embodiment is a compound of Formula (Ia"), wherein $R_2$ is $C_1$-$C_6$alkyl$C_3$-$C_6$cycloalkyl. In another embodiment is a compound of Formula (Ia"), wherein $R_2$ is —$CH_2$—$C_3$-$C_6$cycloalkyl. In another embodiment is a compound of Formula (Ia"), wherein $R_2$ is —$CH_2$— cyclopropyl. In another embodiment is a compound of Formula (Ia"), wherein $R_2$ is —$CH_2$— cyclobutyl. In another embodiment is a compound of Formula (Ia"), wherein $R_2$ is —$CH_2$— cyclopentyl. In another embodiment is a compound of Formula (Ia"), wherein $R_2$ is —$CH_2$— cyclohexyl. In another embodiment is a compound of Formula (Ia"), wherein $R_2$ is $C_1$-$C_6$alkyl$C_2$-$C_7$heterocycloalkyl. In another embodiment is a compound of Formula (Ia"), wherein $R_2$ is —$CH_2$—$C_2$-$C_7$heterocycloalkyl. In another embodiment is a compound of Formula (Ia"), wherein $R_2$ is $C_1$-$C_6$alkyl-$CO_2R_6$. In another embodiment is a compound of Formula (Ia"), wherein $R_2$ is $C_1$-$C_6$alkyl-$CO_2CH_3$. In another embodiment is a compound of Formula (Ia"), wherein $R_2$ is $C_1$-$C_6$alkyl-$CO_2CH_2CH_3$. In another embodiment is a compound of Formula (Ia"), wherein $R_2$ is optionally substituted $C_1$-$C_6$alkylaryl. In another embodiment is a compound of Formula (Ia"), wherein $R_2$ is optionally substituted $C_1$-$C_6$alkylheteroaryl.

In another embodiment is a compound of Formula (Ib):

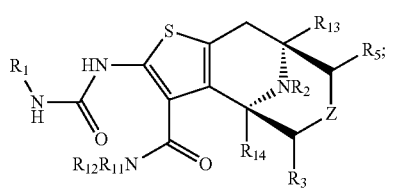

Formula (Ib)

wherein:
Z is a single bond, double bond, —$CH_2$—, or —O—;
$R_1$ is aryl or heteroaryl, wherein aryl and heteroaryl are optionally substituted with one or more $R_4$;
$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl;
$R_3$ and $R_5$ are each independently H, or $C_1$-$C_6$alkyl; or
$R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring;
each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl;
$R_{10}$ is $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl;
$R_{11}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, $C_1$-$C_6$alkyl$C_3$-$C_6$cycloalkyl, $C_1$-$C_6$alkylaryl, or $C_1$-$C_6$alkylheteroaryl;
$R_{12}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, $C_1$-$C_6$alkyl$C_3$-$C_6$cycloalkyl, $C_1$-$C_6$alkylaryl, or $C_1$-$C_6$alkylheteroaryl; or
$R_{11}$ and $R_{12}$ together with the nitrogen to which they are attached form an optionally substituted $C_2$-$C_7$heterocycloalkyl ring; and
$R_{13}$ and $R_{14}$ are each independently H, or $C_1$-$C_6$alkyl;
or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (Ib) wherein $R_{11}$ and $R_{12}$ are each $C_1$-$C_6$alkyl. In another embodiment is a compound of Formula (Ib) wherein $R_{11}$ and $R_{12}$ are each —$CH_3$. In another embodiment is a compound of Formula (Ib) wherein $R_{11}$ is H and $R_{12}$ is $C_1$-$C_6$alkyl. In another embodiment is a compound of Formula (Ib) wherein $R_{11}$ is H and $R_{12}$ is —$CH_3$. In another embodiment is a compound of Formula (Ib) wherein $R_{11}$ is H and $R_{12}$ is $C_3$-$C_6$cycloalkyl. In another embodiment is a compound of Formula (Ib) wherein $R_{11}$ is H and $R_{12}$ is $C_1$-$C_6$alkyl$C_3$-$C_6$cycloalkyl. In another embodiment is a compound of Formula (Ib) wherein $R_{11}$ is H and $R_{12}$ is $C_1$-$C_6$alkylaryl. In another embodiment is a compound of Formula (Ib) wherein $R_{11}$ is H and $R_{12}$ is $C_1$-$C_6$alkylheteroaryl.

In another embodiment is a compound of Formula (Ib) wherein $R_{13}$ and $R_{14}$ are each H. In another embodiment is a compound of Formula (Ib) wherein $R_{13}$ and $R_{14}$ are each —$CH_3$.

In another embodiment is a compound of Formula (Ib) wherein $R_3$ and $R_5$ are each H. In another embodiment is a compound of Formula (Ib) wherein $R_3$ and $R_5$ are each —$CH_3$.

In another embodiment is a compound of Formula (Ib) wherein $R_{11}$ and $R_{12}$ are each H.

In another embodiment is a compound of Formula (Ib), wherein $R_2$ is H. In another embodiment is a compound of Formula (Ib), wherein $R_2$ is $C_1$-$C_6$alkyl. In a further embodiment is a compound of Formula (Ib), wherein $R_2$ is —$CH_3$. In another embodiment is a compound of Formula (Ib), wherein $R_2$ is —$CH_2CH_3$. In another embodiment is a compound of Formula (Ib), wherein $R_2$ is $C_1$-$C_6$alkyl-$OR_6$. In another embodiment is a compound of Formula (Ib), wherein $R_2$ is $C_1$-$C_6$alkyl-OH. In another embodiment is a compound of Formula (Ib), wherein $R_2$ is $C_1$-$C_6$alkyl$C_3$-$C_6$cycloalkyl. In another embodiment is a compound of Formula (Ib), wherein $R_2$ is —$CH_2$—$C_3$-$C_6$cycloalkyl. In another embodiment is a compound of Formula (Ib), wherein $R_2$ is —$CH_2$— cyclopropyl. In another embodiment is a compound of Formula (Ib), wherein $R_2$ is —$CH_2$— cyclobutyl. In another embodiment is a compound of Formula (Ib), wherein $R_2$ is —$CH_2$— cyclopentyl. In another embodiment is a compound of Formula (Ib), wherein $R_2$ is —$CH_2$— cyclohexyl. In another embodiment is a compound of Formula (Ib), wherein $R_2$ is $C_1$-$C_6$alkyl$C_2$-$C_7$heterocycloalkyl. In another embodiment is a compound of Formula (Ib), wherein $R_2$ is —$CH_2$—$C_2$-$C_7$heterocycloalkyl. In another embodiment is a compound of Formula (Ib), wherein $R_2$ is $C_1$-$C_6$alkyl-$CO_2R_6$. In another embodiment is a compound of Formula (Ib), wherein $R_2$ is $C_1$-$C_6$alkyl-$CO_2CH_3$. In another embodiment is a compound of Formula (Ib), wherein $R_2$ is $C_1$-$C_6$alkyl- $CO_2CH_2CH_3$. In another embodiment is a compound of Formula (Ib), wherein $R_2$ is optionally substituted $C_1$-$C_6$alkylaryl. In another embodiment is a compound of Formula (Ib), wherein $R_2$ is optionally substituted $C_1$-$C_6$alkylheteroaryl.

In another embodiment is a compound of Formula (Ib), wherein Z is a single bond. In another embodiment is a compound of Formula (Ib), wherein Z is a double bond. In another embodiment is a compound of Formula (Ib), wherein Z is —$CH_2$—. In another embodiment is a compound of Formula (Ib), wherein Z is —O—.

In another embodiment is a compound of Formula (Ib), having the structure of Formula (Ib'):

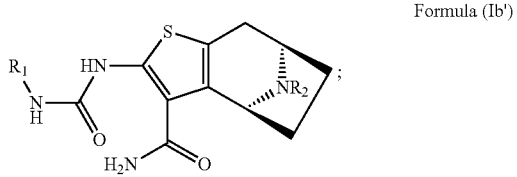

Formula (Ib')

wherein:
$R_1$ is aryl or heteroaryl, wherein aryl and heteroaryl are optionally substituted with one or more $R_4$;
$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl;
each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl; and
$R_{10}$ is $C_1$-$C_6$alkyl, $C_3$-$C_6$cycloalkyl, $C_2$-$C_7$heterocycloalkyl, aryl, heteroaryl, $C_1$-$C_6$alkylaryl, or $C_1$-$C_6$alkylheteroaryl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (Ib'), wherein $R_1$ is aryl optionally substituted with one or more $R_4$. In another embodiment is a compound of Formula (Ib'), wherein $R_1$ is phenyl optionally substituted with one or more $R_4$. In another embodiment is a compound of Formula (Ib'), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (Ib'), wherein $R_1$ is phenyl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (Ib'), wherein $R_1$ is 4-chlorophenyl.

In another embodiment is a compound of Formula (Ib') wherein $R_1$ is heteroaryl optionally substituted with one or more $R_4$. In another embodiment is a compound of Formula (Ib'), wherein $R_1$ is heteroaryl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (Ib'), wherein $R_1$ is heteroaryl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (Ib'), wherein heteroaryl is pyridyl.

In another embodiment is a compound of Formula (Ib'), wherein $R_2$ is H. In another embodiment is a compound of Formula (Ib'), wherein $R_2$ is $C_1$-$C_6$alkyl. In a further embodiment is a compound of Formula (Ib'), wherein $R_2$ is —$CH_3$. In another embodiment is a compound of Formula (Ib'), wherein $R_2$ is —$CH_2CH_3$. In another embodiment is a compound of Formula (Ib'), wherein $R_2$ is $C_1$-$C_6$alkyl-$OR_6$. In another embodiment is a compound of Formula (Ib'), wherein $R_2$ is $C_1$-$C_6$alkyl-OH. In another embodiment is a compound of Formula (Ib'), wherein $R_2$ is $C_1$-$C_6$alkyl$C_3$-$C_6$cycloalkyl. In another embodiment is a compound of Formula (Ib'), wherein $R_2$ is —$CH_2$—$C_3$-$C_6$cycloalkyl. In another embodiment is a compound of Formula (Ib'), wherein $R_2$ is —$CH_2$— cyclopropyl. In another embodiment is a compound of Formula (Ib'), wherein $R_2$ is —$CH_2$— cyclobutyl. In another embodiment is a compound of Formula (Ib'), wherein $R_2$ is —$CH_2$— cyclopentyl. In another embodiment is a compound of Formula (Ib'), wherein $R_2$ is —$CH_2$— cyclohexyl. In another embodiment is a compound of Formula (Ib'), wherein $R_2$ is $C_1$-$C_6$alkyl$C_2$-$C_7$heterocycloalkyl. In another embodiment is a compound of Formula (Ib'), wherein $R_2$ is —$CH_2$—$C_2$-$C_7$heterocycloalkyl. In another embodiment is a compound of Formula (Ib'), wherein $R_2$ is $C_1$-$C_6$alkyl-$CO_2R_6$. In another embodiment is a compound of Formula (Ib'), wherein $R_2$ is $C_1$-$C_6$alkyl-$CO_2CH_3$. In another embodiment is a compound of Formula (Ib'), wherein $R_2$ is $C_1$-$C_6$alkyl-$CO_2CH_2CH_3$. In another embodiment is a compound of Formula (Ib'), wherein $R_2$ is optionally substituted $C_1$-$C_6$alkylaryl. In another embodiment is a compound of Formula (Ib'), wherein $R_2$ is optionally substituted $C_1$-$C_6$alkylheteroaryl.

In another embodiment is a compound of Formula (Ib), having the structure of Formula (Ib"):

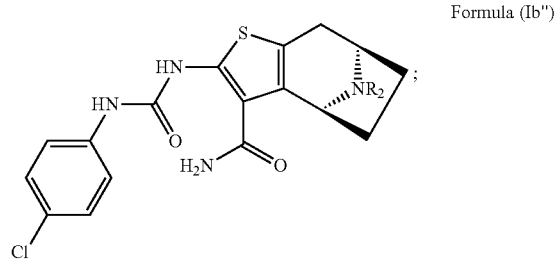

Formula (Ib")

wherein:
$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkylaryl, or optionally substituted $C_1$-$C_6$alkylheteroaryl;
$R_6$ is H, or $C_1$-$C_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (Ib"), wherein $R_2$ is H. In another embodiment is a compound of Formula (Ib"), wherein $R_2$ is $C_1$-$C_6$alkyl. In a further embodiment is a compound of Formula (Ib"), wherein $R_2$ is —$CH_3$. In another embodiment is a compound of Formula (Ib"), wherein $R_2$ is —$CH_2CH_3$. In another embodiment is a compound of Formula (Ib"), wherein $R_2$ is $C_1$-$C_6$alkyl-$OR_6$. In another embodiment is a compound of Formula (Ib"), wherein $R_2$ is $C_1$-$C_6$alkyl-OH. In another embodiment is a compound of Formula (Ib"), wherein $R_2$ is $C_1$-$C_6$alkyl$C_3$-$C_6$cycloalkyl. In another embodiment is a compound of Formula (Ib"), wherein $R_2$ is —$CH_2$—$C_3$-$C_6$cycloalkyl. In another embodiment is a compound of Formula (Ib"), wherein $R_2$ is —$CH_2$— cyclopropyl. In another embodiment is a compound of Formula (Ib"), wherein $R_2$ is —$CH_2$— cyclobutyl. In another embodiment is a compound of Formula (Ib"), wherein $R_2$ is —$CH_2$— cyclopentyl. In another embodiment is a compound of Formula (Ib"), wherein $R_2$ is —$CH_2$— cyclohexyl. In another embodiment is a compound of Formula (Ib"), wherein $R_2$ is $C_1$-$C_6$alkyl$C_2$-$C_7$heterocycloalkyl. In another embodiment is a compound of Formula (Ib"), wherein $R_2$ is —$CH_2$—$C_2$-$C_7$heterocycloalkyl. In another embodiment is a compound of Formula (Ib"), wherein $R_2$ is $C_1$-$C_6$alkyl-$CO_2R_6$. In another embodiment is a compound of Formula (Ib"), wherein $R_2$ is $C_1$-$C_6$alkyl-$CO_2CH_3$. In another embodiment is a compound of Formula (Ib"), wherein $R_2$ is $C_1$-$C_6$alkyl-$CO_2CH_2CH_3$. In another embodiment is a compound of Formula (Ib"), wherein $R_2$ is optionally substituted $C_1$-$C_6$alkylaryl. In another embodiment is a compound of Formula (Ib"), wherein $R_2$ is optionally substituted $C_1$-$C_6$alkylheteroaryl.

In another embodiment is a compound of Formula (II):

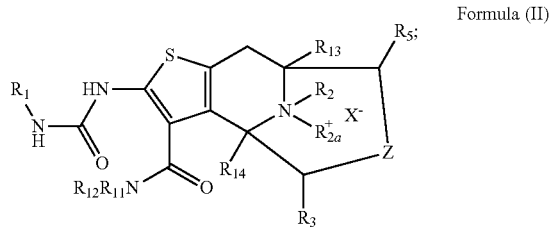

Formula (II)

wherein:
$X^-$ is a counterion;
Z is a single bond, double bond, —$CH_2$—, or —O—;
$R_1$ is aryl or heteroaryl, wherein aryl and heteroaryl are optionally substituted with one or more $R_4$;
$R_{2a}$ is $C_1$-$C_6$alkyl, —$C_1$-$C_6$alkyl-$OR_5$, or —$C_1$-$C_6$alkyl$C_3$-$C_6$cycloalkyl;
$R_2$ is $C_1$-$C_6$alkyl, —$C_1$-$C_6$alkyl-$OR_6$, —$C_1$-$C_6$alkyl$C_3$-$C_6$cycloalkyl, or —$C_1$-$C_6$alkyl-$CO_2R_6$;
$R_3$ and $R_5$ are each independently H, or $C_1$-$C_6$alkyl; or
$R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring;
each $R_4$ is independently selected from F, Cl, Br, I, —CN, —$NO_2$, —$CF_3$, —$OR_9$, —$OCF_3$, —$NR_8R_9$, —C(O)$R_{10}$, —$CO_2R_9$, —C(O)$NR_8R_9$, —N($R_8$)C(O)$R_{10}$, —N($R_8$)$CO_2R_{10}$, —NHS(O)$_2R_{10}$, —S(O)$_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_6$ is H, or $C_1$-$C_6$alkyl;

$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;
$R_{10}$ is $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;
$R_{11}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —$C_1$-$C_6$alkyl$C_3$-$C_6$cycloalkyl, —$C_1$-$C_6$alkylaryl, or —$C_1$-$C_6$alkylheteroaryl;
$R_{12}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —$C_1$-$C_6$alkyl$C_3$-$C_6$cycloalkyl, —$C_1$-$C_6$alkylaryl, or —$C_1$-$C_6$alkylheteroaryl;
or $R_{11}$ and $R_{12}$ together with the nitrogen to which they are attached form an optionally substituted $C_2$-$C_7$heterocycloalkyl ring; and
$R_{13}$ and $R_{14}$ are each independently H, or $C_1$-$C_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (II), wherein $R_1$ is aryl optionally substituted with one or more $R_4$. In another embodiment is a compound of Formula (II), wherein $R_1$ is phenyl optionally substituted with one or more $R_4$. In another embodiment is a compound of Formula (II), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —C(O)$R_{10}$, —$CO_2R_9$, $C_1$-$C_6$alkyl, and $C_1$-$C_6$haloalkyl. In another embodiment is a compound of Formula (II), wherein $R_1$ is phenyl substituted with one or more $R_4$, wherein each $R_4$ is independently selected F, Cl, Br, I, —CN, —$CF_3$, —$OR_9$, —$OCF_3$, —C(O)$R_{10}$, —$CO_2R_9$, and $C_1$-$C_6$alkyl. In another embodiment is a compound of Formula (II), wherein $R_1$ is 4-chlorophenyl.

In another embodiment is a compound of Formula (II) wherein $R_1$ is heteroaryl optionally substituted with one or more $R_4$. In another embodiment is a compound of Formula (II), wherein $R_1$ is heteroaryl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —C(O)$R_{10}$, —$CO_2R_9$, $C_1$-$C_6$alkyl, and $C_1$-$C_6$haloalkyl. In another embodiment is a compound of Formula (II), wherein $R_1$ is heteroaryl substituted with one or more $R_4$, wherein each $R_4$ is independently selected F, Cl, Br, I, —CN, —$CF_3$, —$OR_9$, —$OCF_3$, —C(O)$R_{10}$, —$CO_2R_9$, and $C_1$-$C_6$alkyl. In another embodiment is a compound of Formula (II), wherein heteroaryl is pyridyl.

In another embodiment is a compound of Formula (II) wherein $R_{11}$ and $R_{12}$ are each $C_1$-$C_6$alkyl. In another embodiment is a compound of Formula (II) wherein $R_{11}$ and $R_{12}$ are each —$CH_3$. In another embodiment is a compound of Formula (II) wherein $R_{11}$ is H and $R_{12}$ is $C_1$-$C_6$alkyl. In another embodiment is a compound of Formula (II) wherein $R_{11}$ is H and $R_{12}$ is —$CH_3$. In another embodiment is a compound of Formula (II) wherein $R_{11}$ is H and $R_{12}$ is $C_3$-$C_6$cycloalkyl. In another embodiment is a compound of Formula (II) wherein $R_{11}$ is H and $R_{12}$ is $C_1$-$C_6$alkyl$C_3$-$C_6$cycloalkyl. In another embodiment is a compound of Formula (II) wherein $R_{11}$ is H and $R_{12}$ is $C_1$-$C_6$alkylaryl. In another embodiment is a compound of Formula (II) wherein $R_{11}$ is H and $R_{12}$ is $C_1$-$C_6$alkylheteroaryl.

In another embodiment is a compound of Formula (II) wherein $R_{13}$ and $R_{14}$ are each H. In another embodiment is a compound of Formula (II) wherein $R_{13}$ and $R_{14}$ are each —$CH_3$.

In another embodiment is a compound of Formula (II) wherein $R_3$ and $R_5$ are each H. In another embodiment is a compound of Formula (II) wherein $R_3$ and $R_5$ are each —$CH_3$.

In another embodiment is a compound of Formula (II) wherein $R_{11}$ and $R_{12}$ are each H.

In another embodiment is a compound of Formula (II), wherein $R_2$ is $C_1$-$C_6$alkyl. In a further embodiment is a compound of Formula (II), wherein $R_2$ is —$CH_3$. In another embodiment is a compound of Formula (II), wherein $R_2$ is —$CH_2CH_3$. In another embodiment is a compound of Formula (II), wherein $R_2$ is $C_1$-$C_6$alkyl-$OR_6$. In another embodiment is a compound of Formula (II), wherein $R_2$ is $C_1$-$C_6$alkyl-OH. In another embodiment is a compound of Formula (II), wherein $R_2$ is $C_1$-$C_6$alkyl$C_3$-$C_6$cycloalkyl. In another embodiment is a compound of Formula (II), wherein $R_2$ is —$CH_2$—$C_3$-$C_6$cycloalkyl. In another embodiment is a compound of Formula (II), wherein $R_2$ is —$CH_2$-cyclopropyl. In another embodiment is a compound of Formula (II), wherein $R_2$ is —$CH_2$— cyclobutyl. In another embodiment is a compound of Formula (II), wherein $R_2$ is —$CH_2$-cyclopentyl. In another embodiment is a compound of Formula (II), wherein $R_2$ is —$CH_2$-cyclohexyl. In another embodiment is a compound of Formula (II), wherein $R_2$ is $C_1$-$C_6$alkyl-$CO_2R_6$. In another embodiment is a compound of Formula (II), wherein $R_2$ is $C_1$-$C_6$alkyl-$CO_2CH_3$. In another embodiment is a compound of Formula (II), wherein $R_2$ is $C_1$-$C_6$alkyl-$CO_2CH_2CH_3$.

In another embodiment is a compound of Formula (II), wherein $R_{2a}$ is $C_1$-$C_6$alkyl. In a further embodiment is a compound of Formula (II), wherein $R_{2a}$ is —$CH_3$. In another embodiment is a compound of Formula (II), wherein $R_{2a}$ is —$CH_2CH_3$. In another embodiment is a compound of Formula (II), wherein $R_{2a}$ is $C_1$-$C_6$alkyl-$OR_5$. In another embodiment is a compound of Formula (II), wherein $R_{2a}$ is $C_1$-$C_6$alkyl-OH. In another embodiment is a compound of Formula (II), wherein $R_{2a}$ is $C_1$-$C_6$alkyl$C_3$-$C_6$cycloalkyl. In another embodiment is a compound of Formula (II), wherein $R_{2a}$ is —$CH_2$—$C_3$-$C_6$cycloalkyl. In another embodiment is a compound of Formula (II), wherein $R_{2a}$ is —$CH_2$-cyclopropyl. In another embodiment is a compound of Formula (II), wherein $R_{2a}$ is —$CH_2$-cyclobutyl. In another embodiment is a compound of Formula (II), wherein $R_{2a}$ is —$CH_2$-cyclopentyl. In another embodiment is a compound of Formula (II), wherein $R_{2a}$ is —$CH_2$-cyclohexyl.

In another embodiment is a compound of Formula (II), wherein $R_2$ is $C_1$-$C_6$alkyl and $R_{2a}$ is $C_1$-$C_6$alkyl. In another embodiment is a compound of Formula (II), wherein $R_2$ is —$CH_3$ and $R_{2a}$ is —$CH_3$. In another embodiment is a compound of Formula (II), wherein $R_2$ is —$CH_2CH_3$ and $R_{2a}$ is —$CH_3$. In another embodiment is a compound of Formula (II), wherein $R_2$ is —$C_1$-$C_6$alkyl-$OR_6$ and $R_{2a}$ is $C_1$-$C_6$alkyl. In another embodiment is a compound of Formula (II), wherein $R_2$ is —$C_1$-$C_6$alkyl-OH and $R_{2a}$ is $C_1$-$C_6$alkyl. In another embodiment is a compound of Formula (II), wherein $R_2$ is —$C_1$-$C_6$alkyl-OH and $R_{2a}$ is —$CH_3$. In another embodiment is a compound of Formula (II), wherein $R_2$ is —$C_1$-$C_6$alkyl$C_3$-$C_6$cycloalkyl and $R_{2a}$ is $C_1$-$C_6$alkyl. In another embodiment is a compound of Formula (II), wherein $R_2$ is —$C_1$-$C_6$alkyl$C_3$-$C_6$cycloalkyl and $R_{2a}$ is —$CH_3$. In another embodiment is a compound of Formula (II), wherein $R_2$ is —$CH_2$—$C_3$-$C_6$cycloalkyl and $R_{2a}$ is —$CH_3$. In another embodiment is a compound of Formula (II), wherein $R_2$ is —$C_1$-$C_6$alkyl-$CO_2R_6$ and $R_{2a}$ is $C_1$-$C_6$alkyl. In another embodiment is a compound of Formula (II), wherein $R_2$ is —$C_1$-$C_6$alkyl-$CO_2CH_3$ and $R_{2a}$ is —$CH_3$.

In another embodiment is a compound of Formula (II), wherein Z is a single bond. In another embodiment is a compound of Formula (II), wherein Z is a double bond. In another embodiment is a compound of Formula (II), wherein Z is —$CH_2$—. In another embodiment is a compound of Formula (II), wherein Z is —O—.

In another embodiment is a compound of Formula (II), wherein $X^-$ is $Cl^-$. In another embodiment is a compound of Formula (II), wherein $X^-$ is $Br^-$. In another embodiment is a compound of Formula (II), wherein $X^-$ is $I^-$. In another embodiment is a compound of Formula (II), wherein $X^-$ is $CF_3CO_2^-$. In another embodiment is a compound of Formula (II), wherein $X^-$ is $Cl^-$, $Br^-$, $I^-$, or $CF_3CO_2^-$.

In another embodiment is a compound of Formula (II), having the structure of Formula (II'):

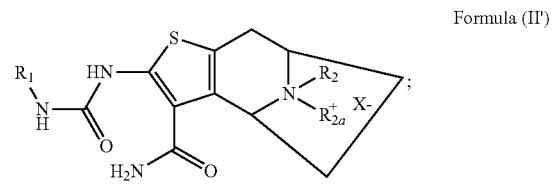

Formula (II')

wherein:
$X^-$ is a counterion;
$R_1$ is aryl or heteroaryl, wherein aryl and heteroaryl are optionally substituted with one or more $R_4$;
$R_{2a}$ is $C_1$-$C_6$alkyl, —$C_1$-$C_6$alkyl-$OR_5$, or —$C_1$-$C_6$alkyl$C_3$-$C_6$cycloalkyl;
$R_2$ is $C_1$-$C_6$alkyl, —$C_1$-$C_6$alkyl-$OR_6$, —$C_1$-$C_6$alkyl$C_3$-$C_6$cycloalkyl, or —$C_1$-$C_6$alkyl-$CO_2R_6$;
each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_5$ is H, or $C_1$-$C_6$alkyl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl; and
$R_{10}$ is $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (II'), wherein $R_1$ is aryl optionally substituted with one or more $R_4$. In another embodiment is a compound of Formula (II'), wherein $R_1$ is phenyl optionally substituted with one or more $R_4$. In another embodiment is a compound of Formula (II'), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (II'), wherein $R_1$ is phenyl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (II'), wherein $R_1$ is 4-chlorophenyl.

In another embodiment is a compound of Formula (II') wherein $R_1$ is heteroaryl optionally substituted with one or more $R_4$. In another embodiment is a compound of Formula (II'), wherein $R_1$ is heteroaryl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In another embodiment is a compound of Formula (II'), wherein $R_1$ is heteroaryl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (II'), wherein heteroaryl is pyridyl.

In another embodiment is a compound of Formula (II'), wherein $R_2$ is $C_1$-$C_6$alkyl. In a further embodiment is a compound of Formula (II'), wherein $R_2$ is —CH$_3$. In another embodiment is a compound of Formula (II'), wherein $R_2$ is —CH$_2$CH$_3$. In another embodiment is a compound of Formula (II'), wherein $R_2$ is $C_1$-$C_6$alkyl-OR$_6$. In another embodiment is a compound of Formula (II'), wherein $R_2$ is $C_1$-$C_6$alkyl-OH. In another embodiment is a compound of Formula (II'), wherein $R_2$ is $C_1$-$C_6$alkylC$_3$-$C_6$cycloalkyl. In another embodiment is a compound of Formula (II'), wherein $R_2$ is —CH$_2$—C$_3$-$C_6$cycloalkyl. In another embodiment is a compound of Formula (II'), wherein $R_2$ is —CH$_2$-cyclopropyl. In another embodiment is a compound of Formula (II'), wherein $R_2$ is —CH$_2$-cyclobutyl. In another embodiment is a compound of Formula (II'), wherein $R_2$ is —CH$_2$— cyclopentyl. In another embodiment is a compound of Formula (II'), wherein $R_2$ is —CH$_2$— cyclohexyl. In another embodiment is a compound of Formula (II'), wherein $R_2$ is $C_1$-$C_6$alkyl-CO$_2$R$_6$. In another embodiment is a compound of Formula (II'), wherein $R_2$ is $C_1$-$C_6$alkyl-CO$_2$CH$_3$. In another embodiment is a compound of Formula (II'), wherein $R_2$ is $C_1$-$C_6$alkyl-CO$_2$CH$_2$CH$_3$.

In another embodiment is a compound of Formula (II'), wherein $R_{2a}$ is $C_1$-$C_6$alkyl. In a further embodiment is a compound of Formula (II'), wherein $R_{2a}$ is —CH$_3$. In another embodiment is a compound of Formula (II'), wherein $R_{2a}$ is —CH$_2$CH$_3$. In another embodiment is a compound of Formula (II'), wherein $R_{2a}$ is $C_1$-$C_6$alkyl-OR$_5$. In another embodiment is a compound of Formula (II'), wherein $R_{2a}$ is $C_1$-$C_6$alkyl-OH. In another embodiment is a compound of Formula (II'), wherein $R_{2a}$ is $C_1$-$C_6$alkylC$_3$-$C_6$cycloalkyl. In another embodiment is a compound of Formula (II'), wherein $R_{2a}$ is —CH$_2$—C$_3$-$C_6$cycloalkyl. In another embodiment is a compound of Formula (II'), wherein $R_{2a}$ is —CH$_2$-cyclopropyl. In another embodiment is a compound of Formula (II'), wherein $R_{2a}$ is —CH$_2$-cyclobutyl. In another embodiment is a compound of Formula (II'), wherein $R_{2a}$ is —CH$_2$-cyclopentyl. In another embodiment is a compound of Formula (II'), wherein $R_{2a}$ is —CH$_2$-cyclohexyl.

In another embodiment is a compound of Formula (II'), wherein $R_2$ is $C_1$-$C_6$alkyl and $R_{2a}$ is $C_1$-$C_6$alkyl. In another embodiment is a compound of Formula (II'), wherein $R_2$ is —CH$_3$ and $R_{2a}$ is —CH$_3$. In another embodiment is a compound of Formula (II'), wherein $R_2$ is —CH$_2$CH$_3$ and $R_{2a}$ is —CH$_3$. In another embodiment is a compound of Formula (II'), wherein $R_2$ is —C$_1$-C$_6$alkyl-OR$_6$ and $R_{2a}$ is $C_1$-$C_6$alkyl. In another embodiment is a compound of Formula (II'), wherein $R_2$ is —C$_1$-C$_6$alkyl-OH and $R_{2a}$ is $C_1$-$C_6$alkyl. In another embodiment is a compound of Formula (II'), wherein $R_2$ is —C$_1$-C$_6$alkyl-OH and $R_{2a}$ is —CH$_3$. In another embodiment is a compound of Formula (II'), wherein $R_2$ is —C$_1$-C$_6$alkylC$_3$-$C_6$cycloalkyl and $R_{2a}$ is $C_1$-$C_6$alkyl. In another embodiment is a compound of Formula (II'), wherein $R_2$ is —C$_1$-C$_6$alkylC$_3$-$C_6$cycloalkyl and $R_{2a}$ is —CH$_3$. In another embodiment is a compound of Formula (II'), wherein $R_2$ is —CH$_2$—C$_3$-$C_6$cycloalkyl and $R_{2a}$ is —CH$_3$. In another embodiment is a compound of Formula (II'), wherein $R_2$ is —C$_1$-C$_6$alkyl-CO$_2$R$_6$ and $R_{2a}$ is $C_1$-$C_6$alkyl. In another embodiment is a compound of Formula (II'), wherein $R_2$ is —C$_1$-C$_6$alkyl-CO$_2$CH$_3$ and $R_{2a}$ is —CH$_3$.

In another embodiment is a compound of Formula (II'), wherein X$^-$ is Cl$^-$. In another embodiment is a compound of Formula (II'), wherein X$^-$ is Br$^-$. In another embodiment is a compound of Formula (II'), wherein X$^-$ is I$^-$. In another embodiment is a compound of Formula (II'), wherein X$^-$ is CF$_3$CO$_2$. In another embodiment is a compound of Formula (II'), wherein X$^-$ is Cl$^-$, Br$^-$, I$^-$, or CF$_3$CO$_2^-$.

In another embodiment is a compound of Formula (II), having the structure of Formula (II"):

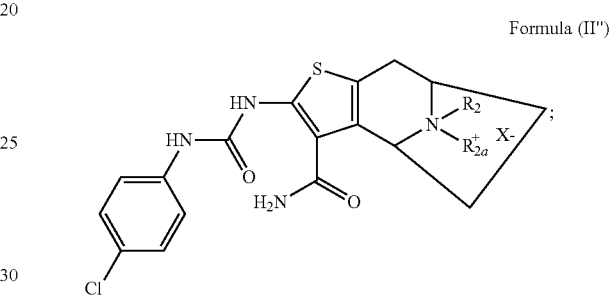

Formula (II")

wherein:
X$^-$ is a counterion;
$R_{2a}$ is $C_1$-$C_6$alkyl;
$R_2$ is $C_1$-$C_6$alkyl, —$C_1$-$C_6$alkyl-OR$_6$, —$C_1$-$C_6$alkylC$_3$-$C_6$cycloalkyl, or —$C_1$-$C_6$alkyl-CO$_2$R$_6$; and
$R_6$ is H, or $C_1$-$C_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (II"), wherein $R_2$ is $C_1$-$C_6$alkyl. In a further embodiment is a compound of Formula (II"), wherein $R_2$ is —CH$_3$. In another embodiment is a compound of Formula (II"), wherein $R_2$ is —CH$_2$CH$_3$. In another embodiment is a compound of Formula (II"), wherein $R_2$ is $C_1$-$C_6$alkyl-OR$_6$. In another embodiment is a compound of Formula (II"), wherein $R_2$ is $C_1$-$C_6$alkyl-OH. In another embodiment is a compound of Formula (II"), wherein $R_2$ is $C_1$-$C_6$alkylC$_3$-$C_6$cycloalkyl. In another embodiment is a compound of Formula (II"), wherein $R_2$ is —CH$_2$—C$_3$-$C_6$cycloalkyl. In another embodiment is a compound of Formula (II"), wherein $R_2$ is —CH$_2$-cyclopropyl. In another embodiment is a compound of Formula (II"), wherein $R_2$ is —CH$_2$-cyclobutyl. In another embodiment is a compound of Formula (II"), wherein $R_2$ is —CH$_2$-cyclopentyl. In another embodiment is a compound of Formula (II"), wherein $R_2$ is —CH$_2$— cyclohexyl. In another embodiment is a compound of Formula (II"), wherein $R_2$ is $C_1$-$C_6$alkyl-CO$_2$R$_6$. In another embodiment is a compound of Formula (II"), wherein $R_2$ is $C_1$-$C_6$alkyl-CO$_2$CH$_3$. In another embodiment is a compound of Formula (II"), wherein $R_2$ is $C_1$-$C_6$alkyl-CO$_2$CH$_2$CH$_3$.

In another embodiment is a compound of Formula (II"), wherein $R_{2a}$ is $C_1$-$C_6$alkyl. In a further embodiment is a compound of Formula (II"), wherein $R_{2a}$ is —CH$_3$. In another embodiment is a compound of Formula (II"), wherein $R_{2a}$ is —CH$_2$CH$_3$.

In another embodiment is a compound of Formula (II"), wherein $R_2$ is $C_1$-$C_6$alkyl and $R_{2a}$ is $C_1$-$C_6$alkyl. In another embodiment is a compound of Formula (II"), wherein $R_2$ is —CH$_3$ and $R_{2a}$ is —CH$_3$. In another embodiment is a compound of Formula (II"), wherein $R_2$ is —CH$_2$CH$_3$ and $R_{2a}$ is —CH$_3$. In another embodiment is a compound of Formula (II"), wherein $R_2$ is —C$_1$-C$_6$alkyl-OR$_6$ and $R_{2a}$ is $C_1$-$C_6$alkyl. In another embodiment is a compound of Formula (II"), wherein $R_2$ is —C$_1$-C$_6$alkyl-OH and $R_{2a}$ is $C_1$-$C_6$alkyl. In another embodiment is a compound of Formula (II"), wherein $R_2$ is —C$_1$-C$_6$alkyl-OH and $R_{2a}$ is —CH$_3$. In another embodiment is a compound of Formula (II"), wherein $R_2$ is —C$_1$-C$_6$alkylC$_3$-C$_6$cycloalkyl and $R_{2a}$ is $C_1$-$C_6$alkyl. In another embodiment is a compound of Formula (II"), wherein $R_2$ is —C$_1$-C$_6$alkylC$_3$-C$_6$cycloalkyl and $R_{2a}$ is —CH$_3$. In another embodiment is a compound of Formula (II"), wherein $R_2$ is —CH$_2$—C$_3$-C$_6$cycloalkyl and $R_{2a}$ is —CH$_3$. In another embodiment is a compound of Formula (II"), wherein $R_2$ is —C$_1$-C$_6$alkyl-CO$_2$R$_6$ and $R_{2a}$ is $C_1$-$C_6$alkyl. In another embodiment is a compound of Formula (II"), wherein $R_2$ is —C$_1$-C$_6$alkyl-CO$_2$CH$_3$ and $R_{2a}$ is —CH$_3$.

In another embodiment is a compound of Formula (II"), wherein X$^-$ is Cl$^-$. In another embodiment is a compound of Formula (II"), wherein X$^-$ is Br$^-$. In another embodiment is a compound of Formula (II"), wherein X$^-$ is I$^-$. In another embodiment is a compound of Formula (II"), wherein X$^-$ is CF$_3$CO$_2^-$. In another embodiment is a compound of Formula (II"), wherein X is Cl$^-$, Br$^-$, I$^-$, or CF$_3$CO$_2^-$.

In another embodiment is a compound of Formula (IIa):

Formula (IIa)

wherein:
X$^-$ is a counterion;
Z is a single bond, double bond, —CH$_2$—, or —O—;
$R_1$ is aryl or heteroaryl, wherein aryl and heteroaryl are optionally substituted with one or more $R_4$;
$R_{2a}$ is $C_1$-$C_6$alkyl, —C$_1$-C$_6$alkyl-OR$_5$, or —C$_1$-C$_6$alkylC$_3$-C$_6$cycloalkyl;
$R_2$ is $C_1$-$C_6$alkyl, —C$_1$-C$_6$alkyl-OR$_6$, —C$_1$-C$_6$alkylC$_3$-C$_6$cycloalkyl, or —C$_1$-C$_6$alkyl-CO$_2$R$_6$;
$R_3$ and $R_5$ are each independently H, or $C_1$-$C_6$alkyl; or
$R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring;
each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, —C$_1$-C$_6$alkylaryl, or —C$_1$-C$_6$alkylheteroaryl;
$R_{10}$ is $C_1$-$C_6$alkyl, $C_3$-$C_6$cycloalkyl, $C_2$-$C_7$heterocycloalkyl, aryl, heteroaryl, —C$_1$-C$_6$alkylaryl, or —C$_1$-C$_6$alkylheteroaryl;
$R_{11}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —C$_1$-C$_6$alkylC$_3$-C$_6$cycloalkyl, —C$_1$-C$_6$alkylaryl, or —C$_1$-C$_6$alkylheteroaryl;
$R_{12}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —C$_1$-C$_6$alkylC$_3$-C$_6$cycloalkyl, —C$_1$-C$_6$alkylaryl, or —C$_1$-C$_6$alkylheteroaryl;
or $R_{11}$ and $R_{12}$ together with the nitrogen to which they are attached form an optionally substituted $C_2$-$C_7$heterocycloalkyl ring; and
$R_{13}$ and $R_{14}$ are each independently H, or $C_1$-$C_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (IIa), wherein $R_1$ is aryl optionally substituted with one or more $R_4$. In another embodiment is a compound of Formula (IIa), wherein $R_1$ is phenyl optionally substituted with one or more $R_4$. In another embodiment is a compound of Formula (IIa), wherein $R_1$ is phenyl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In another embodiment is a compound of Formula (IIa), wherein $R_1$ is phenyl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (IIa), wherein $R_1$ is 4-chlorophenyl.

In another embodiment is a compound of Formula (IIa) wherein $R_1$ is heteroaryl optionally substituted with one or more $R_4$. In another embodiment is a compound of Formula (IIa), wherein $R_1$ is heteroaryl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In another embodiment is a compound of Formula (IIa), wherein $R_1$ is heteroaryl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (IIa), wherein heteroaryl is pyridyl.

In another embodiment is a compound of Formula (IIa) wherein $R_{11}$ and $R_{12}$ are each $C_1$-$C_6$alkyl. In another embodiment is a compound of Formula (IIa) wherein $R_{11}$ and $R_{12}$ are each —CH$_3$. In another embodiment is a compound of Formula (IIa) wherein $R_{11}$ is H and $R_{12}$ is $C_1$-$C_6$alkyl. In another embodiment is a compound of Formula (IIa) wherein $R_{11}$ is H and $R_{12}$ is —CH$_3$. In another embodiment is a compound of Formula (IIa) wherein $R_{11}$ is H and $R_{12}$ is $C_3$-$C_6$cycloalkyl. In another embodiment is a compound of Formula (IIa) wherein $R_{11}$ is H and $R_{12}$ is $C_1$-$C_6$alkylC$_3$-$C_6$cycloalkyl. In another embodiment is a compound of Formula (IIa) wherein $R_{11}$ is H and $R_{12}$ is $C_1$-$C_6$alkylaryl. In another embodiment is a compound of Formula (IIa) wherein $R_{11}$ is H and $R_{12}$ is $C_1$-$C_6$alkylheteroaryl.

In another embodiment is a compound of Formula (IIa) wherein $R_{13}$ and $R_{14}$ are each H. In another embodiment is a compound of Formula (IIa) wherein $R_{13}$ and $R_{14}$ are each —$CH_3$.

In another embodiment is a compound of Formula (IIa) wherein $R_3$ and $R_5$ are each H. In another embodiment is a compound of Formula (IIa) wherein $R_3$ and $R_5$ are each —$CH_3$.

In another embodiment is a compound of Formula (IIa) wherein $R_{11}$ and $R_{12}$ are each H.

In another embodiment is a compound of Formula (IIa), wherein $R_2$ is $C_1$-$C_6$alkyl. In a further embodiment is a compound of Formula (IIa), wherein $R_2$ is —$CH_3$. In another embodiment is a compound of Formula (II), wherein $R_2$ is —$CH_2CH_3$. In another embodiment is a compound of Formula (IIa), wherein $R_2$ is $C_1$-$C_6$alkyl-$OR_6$. In another embodiment is a compound of Formula (IIa), wherein $R_2$ is $C_1$-$C_6$alkyl-OH. In another embodiment is a compound of Formula (IIa), wherein $R_2$ is $C_1$-$C_6$alkyl$C_3$-$C_6$cycloalkyl. In another embodiment is a compound of Formula (IIa), wherein $R_2$ is —$CH_2$—$C_3$-$C_6$cycloalkyl. In another embodiment is a compound of Formula (IIa), wherein $R_2$ is —$CH_2$-cyclopropyl. In another embodiment is a compound of Formula (IIa), wherein $R_2$ is —$CH_2$-cyclobutyl. In another embodiment is a compound of Formula (IIa), wherein $R_2$ is —$CH_2$-cyclopentyl. In another embodiment is a compound of Formula (IIa), wherein $R_2$ is —$CH_2$— cyclohexyl. In another embodiment is a compound of Formula (IIa), wherein $R_2$ is $C_1$-$C_6$alkyl-$CO_2R_6$. In another embodiment is a compound of Formula (IIa), wherein $R_2$ is $C_1$-$C_6$alkyl-$CO_2CH_3$. In another embodiment is a compound of Formula (IIa), wherein $R_2$ is $C_1$-$C_6$alkyl-$CO_2CH_2CH_3$.

In another embodiment is a compound of Formula (IIa), wherein $R_{2a}$ is $C_1$-$C_6$alkyl. In a further embodiment is a compound of Formula (IIa), wherein $R_{2a}$ is —$CH_3$. In another embodiment is a compound of Formula (IIa), wherein $R_{2a}$ is —$CH_2CH_3$. In another embodiment is a compound of Formula (IIa), wherein $R_{2a}$ is $C_1$-$C_6$alkyl-$OR_5$. In another embodiment is a compound of Formula (IIa), wherein $R_{2a}$ is $C_1$-$C_6$alkyl-OH. In another embodiment is a compound of Formula (IIa), wherein $R_{2a}$ is $C_1$-$C_6$alkyl$C_3$-$C_6$cycloalkyl. In another embodiment is a compound of Formula (IIa), wherein $R_{2a}$ is —$CH_2$—$C_3$-$C_6$cycloalkyl. In another embodiment is a compound of Formula (IIa), wherein $R_{2a}$ is —$CH_2$-cyclopropyl. In another embodiment is a compound of Formula (IIa), wherein $R_{2a}$ is —$CH_2$-cyclobutyl. In another embodiment is a compound of Formula (IIa), wherein $R_{2a}$ is —$CH_2$-cyclopentyl. In another embodiment is a compound of Formula (IIa), wherein $R_{2a}$ is —$CH_2$-cyclohexyl.

In another embodiment is a compound of Formula (IIa), wherein $R_2$ is $C_1$-$C_6$alkyl and $R_{2a}$ is $C_1$-$C_6$alkyl. In another embodiment is a compound of Formula (IIa), wherein $R_2$ is —$CH_3$ and $R_{2a}$ is —$CH_3$. In another embodiment is a compound of Formula (IIa), wherein $R_2$ is —$CH_2CH_3$ and $R_{2a}$ is —$CH_3$. In another embodiment is a compound of Formula (IIa), wherein $R_2$ is —$C_1$-$C_6$alkyl-$OR_6$ and $R_{2a}$ is $C_1$-$C_6$alkyl. In another embodiment is a compound of Formula (IIa), wherein $R_2$ is —$C_1$-$C_6$alkyl-OH and $R_{2a}$ is $C_1$-$C_6$alkyl. In another embodiment is a compound of Formula (IIa), wherein $R_2$ is —$C_1$-$C_6$alkyl-OH and $R_{2a}$ is —$CH_3$. In another embodiment is a compound of Formula (IIa), wherein $R_2$ is —$C_1$-$C_6$alkyl$C_3$-$C_6$cycloalkyl and $R_{2a}$ is $C_1$-$C_6$alkyl. In another embodiment is a compound of Formula (IIa), wherein $R_2$ is —$C_1$-$C_6$alkyl$C_3$-$C_6$cycloalkyl and $R_{2a}$ is —$CH_3$. In another embodiment is a compound of Formula (IIa), wherein $R_2$ is —$CH_2$—$C_3$-$C_6$cycloalkyl and $R_{2a}$ is —$CH_3$. In another embodiment is a compound of Formula (IIa), wherein $R_2$ is —$C_1$-$C_6$alkyl-$CO_2R_6$ and $R_{2a}$ is $C_1$-$C_6$alkyl. In another embodiment is a compound of Formula (IIa), wherein $R_2$ is —$C_1$-$C_6$alkyl-$CO_2CH_3$ and $R_{2a}$ is —$CH_3$.

In another embodiment is a compound of Formula (IIa), wherein Z is a single bond. In another embodiment is a compound of Formula (IIa), wherein Z is a double bond. In another embodiment is a compound of Formula (IIa), wherein Z is —$CH_2$—. In another embodiment is a compound of Formula (IIa), wherein Z is —O—.

In another embodiment is a compound of Formula (IIa), wherein $X^-$ is $Cl^-$. In another embodiment is a compound of Formula (IIa), wherein $X^-$ is $Br^-$. In another embodiment is a compound of Formula (IIa), wherein $X^-$ is $I^-$. In another embodiment is a compound of Formula (IIa), wherein $X^-$ is $CF_3CO_2^-$. In another embodiment is a compound of Formula (IIa), wherein $X^-$ is $Cl^-$, $Br^-$, $I^-$, or $CF_3CO_2^-$.

In another embodiment is a compound of Formula (IIa), having the structure of Formula (IIa'):

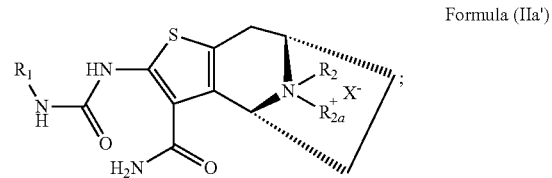

Formula (IIa')

wherein:

$X^-$ is a counterion;

$R_1$ is aryl or heteroaryl, wherein aryl and heteroaryl are optionally substituted with one or more $R_4$;

$R_{2a}$ is $C_1$-$C_6$alkyl, —$C_1$-$C_6$alkyl-$OR_5$, or —$C_1$-$C_6$alkyl$C_3$-$C_6$cycloalkyl;

$R_2$ is $C_1$-$C_6$alkyl, —$C_1$-$C_6$alkyl-$OR_6$, —$C_1$-$C_6$alkyl$C_3$-$C_6$cycloalkyl, or —$C_1$-$C_6$alkyl-$CO_2R_6$;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;

$R_5$ is H, or $C_1$-$C_6$alkyl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl; and $R_{10}$ is $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;

or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (IIa'), wherein $R_1$ is aryl optionally substituted with one or more $R_4$. In another embodiment is a compound of Formula (IIa'), wherein $R_1$ is phenyl optionally substituted with one or more $R_4$. In another embodiment is a compound of Formula (IIa'), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (IIa'), wherein $R_1$ is phenyl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (IIa'), wherein $R_1$ is 4-chlorophenyl.

In another embodiment is a compound of Formula (IIa') wherein $R_1$ is heteroaryl optionally substituted with one or more $R_4$. In another embodiment is a compound of Formula (IIa'), wherein $R_1$ is heteroaryl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (IIa'), wherein $R_1$ is heteroaryl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (IIa'), wherein heteroaryl is pyridyl.

In another embodiment is a compound of Formula (IIa'), wherein $R_2$ is C$_1$-C$_6$alkyl. In a further embodiment is a compound of Formula (IIa'), wherein $R_2$ is —CH$_3$. In another embodiment is a compound of Formula (IIa'), wherein $R_2$ is —CH$_2$CH$_3$. In another embodiment is a compound of Formula (IIa'), wherein $R_2$ is C$_1$-C$_6$alkyl-OR$_6$. In another embodiment is a compound of Formula (IIa'), wherein $R_2$ is C$_1$-C$_6$alkyl-OH. In another embodiment is a compound of Formula (IIa'), wherein $R_2$ is C$_1$-C$_6$alkylC$_3$-C$_6$cycloalkyl. In another embodiment is a compound of Formula (IIa'), wherein $R_2$ is —CH$_2$—C$_3$-C$_6$cycloalkyl. In another embodiment is a compound of Formula (IIa'), wherein $R_2$ is —CH$_2$-cyclopropyl. In another embodiment is a compound of Formula (IIa'), wherein $R_2$ is —CH$_2$-cyclobutyl. In another embodiment is a compound of Formula (IIa'), wherein $R_2$ is —CH$_2$-cyclopentyl. In another embodiment is a compound of Formula (IIa'), wherein $R_2$ is —CH$_2$—cyclohexyl. In another embodiment is a compound of Formula (IIa'), wherein $R_2$ is C$_1$-C$_6$alkyl-CO$_2$R$_6$. In another embodiment is a compound of Formula (IIa'), wherein $R_2$ is C$_1$-C$_6$alkyl-CO$_2$CH$_3$. In another embodiment is a compound of Formula (IIa'), wherein $R_2$ is C$_1$-C$_6$alkyl-CO$_2$CH$_2$CH$_3$.

In another embodiment is a compound of Formula (IIa'), wherein $R_{2a}$ is C$_1$-C$_6$alkyl. In a further embodiment is a compound of Formula (IIa'), wherein $R_{2a}$ is —CH$_3$. In another embodiment is a compound of Formula (IIa'), wherein $R_{2a}$ is —CH$_2$CH$_3$. In another embodiment is a compound of Formula (IIa'), wherein $R_{2a}$ is C$_1$-C$_6$alkyl-OR$_5$. In another embodiment is a compound of Formula (IIa'), wherein $R_{2a}$ is C$_1$-C$_6$alkyl-OH. In another embodiment is a compound of Formula (IIa'), wherein $R_{2a}$ is C$_1$-C$_6$alkylC$_3$-C$_6$cycloalkyl. In another embodiment is a compound of Formula (IIa'), wherein $R_{2a}$ is —CH$_2$—C$_3$-C$_6$cycloalkyl. In another embodiment is a compound of Formula (IIa'), wherein $R_{2a}$ is —CH$_2$-cyclopropyl. In another embodiment is a compound of Formula (IIa'), wherein $R_{2a}$ is —CH$_2$-cyclobutyl. In another embodiment is a compound of Formula (IIa'), wherein $R_{2a}$ is —CH$_2$-cyclopentyl. In another embodiment is a compound of Formula (IIa'), wherein $R_{2a}$ is —CH$_2$-cyclohexyl.

In another embodiment is a compound of Formula (IIa'), wherein $R_2$ is C$_1$-C$_6$alkyl and $R_{2a}$ is C$_1$-C$_6$alkyl. In another embodiment is a compound of Formula (IIa'), wherein $R_2$ is —CH$_3$ and $R_{2a}$ is —CH$_3$. In another embodiment is a compound of Formula (IIa'), wherein $R_2$ is —CH$_2$CH$_3$ and $R_{2a}$ is —CH$_3$. In another embodiment is a compound of Formula (IIa'), wherein $R_2$ is —C$_1$-C$_6$alkyl-OR$_6$ and $R_{2a}$ is C$_1$-C$_6$alkyl. In another embodiment is a compound of Formula (IIa'), wherein $R_2$ is —C$_1$-C$_6$alkyl-OH and $R_{2a}$ is C$_1$-C$_6$alkyl. In another embodiment is a compound of Formula (IIa'), wherein $R_2$ is —C$_1$-C$_6$alkyl-OH and $R_{2a}$ is —CH$_3$. In another embodiment is a compound of Formula (IIa'), wherein $R_2$ is —C$_1$-C$_6$alkylC$_3$-C$_6$cycloalkyl and $R_{2a}$ is C$_1$-C$_6$alkyl. In another embodiment is a compound of Formula (IIa'), wherein $R_2$ is —C$_1$-C$_6$alkylC$_3$-C$_6$cycloalkyl and $R_{2a}$ is —CH$_3$. In another embodiment is a compound of Formula (IIa'), wherein $R_2$ is —CH$_2$—C$_3$-C$_6$cycloalkyl and $R_{2a}$ is —CH$_3$. In another embodiment is a compound of Formula (IIa'), wherein $R_2$ is —C$_1$-C$_6$alkyl-CO$_2$R$_6$ and $R_{2a}$ is C$_1$-C$_6$alkyl. In another embodiment is a compound of Formula (IIa'), wherein $R_2$ is —C$_1$-C$_6$alkyl-CO$_2$CH$_3$ and $R_{2a}$ is —CH$_3$.

In another embodiment is a compound of Formula (IIa'), wherein $X^-$ is Cl$^-$. In another embodiment is a compound of Formula (IIa'), wherein $X^-$ is Br$^-$. In another embodiment is a compound of Formula (IIa'), wherein $X^-$ is I$^-$. In another embodiment is a compound of Formula (IIa'), wherein $X^-$ is CF$_3$CO$_2$. In another embodiment is a compound of Formula (IIa'), wherein X is Cl$^-$, Br$^-$, I$^-$, or CF$_3$CO$_2^-$.

In another embodiment is a compound of Formula (IIa), having the structure of Formula (IIa"):

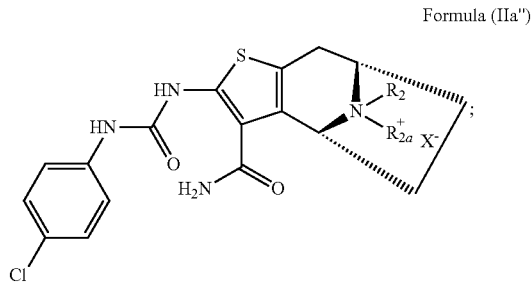

Formula (IIa")

wherein:
$X^-$ is a counterion;
$R_{2a}$ is C$_1$-C$_6$alkyl;
$R_2$ is C$_1$-C$_6$alkyl, —C$_1$-C$_6$alkyl-OR$_6$, —C$_1$-C$_6$alkylC$_3$-C$_6$cycloalkyl, or —C$_1$-C$_6$alkyl-CO$_2$R$_6$; and
$R_6$ is H, or C$_1$-C$_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (IIa"), wherein $R_2$ is C$_1$-C$_6$alkyl. In a further embodiment is a compound of Formula (IIa"), wherein $R_2$ is —CH$_3$. In another embodiment is a compound of Formula (IIa"), wherein $R_2$ is —CH$_2$CH$_3$. In another embodiment is a compound of Formula (IIa"), wherein $R_2$ is C$_1$-C$_6$alkyl-OR$_6$. In another embodiment is a compound of Formula (IIa"), wherein $R_2$ is C$_1$-C$_6$alkyl-OH. In another embodiment is a compound of Formula (IIa"), wherein $R_2$ is C$_1$-C$_6$alkylC$_3$-C$_6$cycloalkyl. In another embodiment is a compound of Formula (IIa"), wherein $R_2$ is —CH$_2$—C$_3$-C$_6$cycloalkyl. In another embodiment is a compound of Formula (IIa"), wherein $R_2$ is —CH$_2$-cyclopropyl. In another embodiment is a compound of Formula (IIa"), wherein $R_2$ is —CH$_2$-cyclobutyl. In another embodiment is a compound of Formula (IIa"), wherein $R_2$ is —CH$_2$-cyclopentyl. In another embodiment is a compound of Formula (IIa"), wherein $R_2$ is —CH$_2$—cyclohexyl. In another embodiment is a compound of Formula (IIa"), wherein $R_2$ is C$_1$-C$_6$alkyl-CO$_2$R$_6$. In another embodiment is a compound of Formula (IIa"), wherein $R_2$ is $C_1$-$C_6$alkyl-$CO_2CH_3$. In another embodiment is a compound of Formula (IIa"), wherein $R_2$ is $C_1$-$C_6$alkyl-$CO_2CH_2CH_3$.

In another embodiment is a compound of Formula (IIa"), wherein $R_{2a}$ is $C_1$-$C_6$alkyl. In a further embodiment is a compound of Formula (IIa"), wherein $R_{2a}$ is —$CH_3$. In another embodiment is a compound of Formula (IIa"), wherein $R_{2a}$ is —$CH_2CH_3$.

In another embodiment is a compound of Formula (IIa"), wherein $R_2$ is $C_1$-$C_6$alkyl and $R_{2a}$ is $C_1$-$C_6$alkyl. In another embodiment is a compound of Formula (IIa"), wherein $R_2$ is —$CH_3$ and $R_{2a}$ is —$CH_3$. In another embodiment is a compound of Formula (IIa"), wherein $R_2$ is —$CH_2CH_3$ and $R_{2a}$ is —$CH_3$. In another embodiment is a compound of Formula (IIa"), wherein $R_2$ is —$C_1$-$C_6$alkyl-$OR_6$ and $R_{2a}$ is $C_1$-$C_6$alkyl. In another embodiment is a compound of Formula (IIa"), wherein $R_2$ is —$C_1$-$C_6$alkyl-OH and $R_{2a}$ is $C_1$-$C_6$alkyl. In another embodiment is a compound of Formula (IIa"), wherein $R_2$ is —$C_1$-$C_6$alkyl-OH and $R_{2a}$ is —$CH_3$. In another embodiment is a compound of Formula (IIa"), wherein $R_2$ is —$C_1$-$C_6$alkyl$C_3$-$C_6$cycloalkyl and $R_{2a}$ is $C_1$-$C_6$alkyl. In another embodiment is a compound of Formula (IIa"), wherein $R_2$ is —$C_1$-$C_6$alkyl$C_3$-$C_6$cycloalkyl and $R_{2a}$ is —$CH_3$. In another embodiment is a compound of Formula (IIa"), wherein $R_2$ is —$CH_2$—$C_3$-$C_6$cycloalkyl and $R_{2a}$ is —$CH_3$. In another embodiment is a compound of Formula (IIa"), wherein $R_2$ is —$C_1$-$C_6$alkyl-$CO_2R_6$ and $R_{2a}$ is $C_1$-$C_6$alkyl. In another embodiment is a compound of Formula (IIa"), wherein $R_2$ is —$C_1$-$C_6$alkyl-$CO_2CH_3$ and $R_{2a}$ is —$CH_3$.

In another embodiment is a compound of Formula (IIa"), wherein $X^-$ is $Cl^-$. In another embodiment is a compound of Formula (IIa"), wherein $X^-$ is $Br^-$. In another embodiment is a compound of Formula (IIa"), wherein $X^-$ is $I^-$. In another embodiment is a compound of Formula (IIa"), wherein $X^-$ is $CF_3CO_2^-$. In another embodiment is a compound of Formula (IIa"), wherein $X^-$ is $Cl^-$, $Br^-$, $I^-$, or $CF_3CO_2^-$.

In another embodiment is a compound of Formula (IIb):

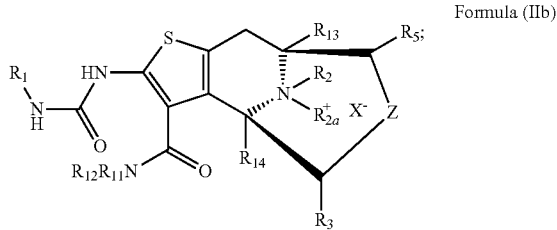

Formula (IIb)

wherein:

$X^-$ is a counterion;

Z is a single bond, double bond, —$CH_2$—, or —O—;

$R_1$ is aryl or heteroaryl, wherein aryl and heteroaryl are optionally substituted with one or more $R_4$;

$R_{2a}$ is $C_1$-$C_6$alkyl, —$C_1$-$C_6$alkyl-$OR_5$, or —$C_1$-$C_6$alkyl$C_3$-$C_6$cycloalkyl;

$R_2$ is $C_1$-$C_6$alkyl, —$C_1$-$C_6$alkyl-$OR_6$, —$C_1$-$C_6$alkyl$C_3$-$C_6$cycloalkyl, or —$C_1$-$C_6$alkyl-$CO_2R_6$;

$R_3$ and $R_5$ are each independently H, or $C_1$-$C_6$alkyl; or $R_3$ and $R_5$ together form an optionally substituted $C_3$-$C_6$cycloalkyl ring, optionally substituted $C_2$-$C_7$heterocycloalkyl ring, optionally substituted aryl ring, or an optionally substituted heteroaryl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;

$R_{10}$ is $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —$C_1$-$C_6$alkyl$C_3$-$C_6$cycloalkyl, —$C_1$-$C_6$alkylaryl, or —$C_1$-$C_6$alkylheteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, aryl, heteroaryl, —$C_1$-$C_6$alkyl$C_3$-$C_6$cycloalkyl, —$C_1$-$C_6$alkylaryl, or —$C_1$-$C_6$alkylheteroaryl;

or $R_{11}$ and $R_{12}$ together with the nitrogen to which they are attached form an optionally substituted $C_2$-$C_7$heterocycloalkyl ring; and $R_{13}$ and $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (IIb), wherein $R_1$ is aryl optionally substituted with one or more $R_4$. In another embodiment is a compound of Formula (IIb), wherein $R_1$ is phenyl optionally substituted with one or more $R_4$. In another embodiment is a compound of Formula (IIb), wherein $R_1$ is phenyl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (IIb), wherein $R_1$ is phenyl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (IIb), wherein $R_1$ is 4-chlorophenyl.

In another embodiment is a compound of Formula (IIb) wherein $R_1$ is heteroaryl optionally substituted with one or more $R_4$. In another embodiment is a compound of Formula (IIb), wherein $R_1$ is heteroaryl substituted with one or more $R_4$, wherein each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, $C_1$-$C_6$alkyl, and $C_1$-$C_6$haloalkyl. In another embodiment is a compound of Formula (IIb), wherein $R_1$ is heteroaryl substituted with one or more $R_4$, wherein each $R_4$ is independently selected F, Cl, Br, I, —CN, —$CF_3$, —$OR_9$, —$OCF_3$, —$C(O)R_{10}$, —$CO_2R_9$, and $C_1$-$C_6$alkyl. In another embodiment is a compound of Formula (IIb), wherein heteroaryl is pyridyl.

In another embodiment is a compound of Formula (IIb) wherein $R_{11}$ and $R_{12}$ are each $C_1$-$C_6$alkyl. In another embodiment is a compound of Formula (IIb) wherein $R_{11}$ and $R_{12}$ are each —$CH_3$. In another embodiment is a compound of Formula (IIb) wherein $R_{11}$ is H and $R_{12}$ is $C_1$-$C_6$alkyl. In another embodiment is a compound of Formula (IIb) wherein $R_{11}$ is H and $R_{12}$ is —$CH_3$. In another embodiment is a compound of Formula (IIb) wherein $R_{11}$ is H and $R_{12}$ is $C_3$-$C_6$cycloalkyl. In another embodiment is a compound of Formula (IIb) wherein $R_{11}$ is H and $R_{12}$ is $C_1$-$C_6$alkyl$C_3$-$C_6$cycloalkyl. In another embodiment is a compound of Formula (IIb) wherein $R_{11}$ is H and $R_{12}$ is $C_1$-$C_6$alkylaryl. In another embodiment is a compound of Formula (IIb) wherein $R_{11}$ is H and $R_{12}$ is $C_1$-$C_6$alkylheteroaryl.

In another embodiment is a compound of Formula (IIb) wherein $R_{13}$ and $R_{14}$ are each H. In another embodiment is a compound of Formula (IIb) wherein $R_{13}$ and $R_{14}$ are each —$CH_3$.

In another embodiment is a compound of Formula (IIb) wherein $R_3$ and $R_5$ are each H. In another embodiment is a compound of Formula (IIb) wherein $R_3$ and $R_5$ are each —$CH_3$.

In another embodiment is a compound of Formula (IIb) wherein $R_{11}$ and $R_{12}$ are each H.

In another embodiment is a compound of Formula (IIb), wherein $R_2$ is $C_1$-$C_6$alkyl. In a further embodiment is a compound of Formula (IIb), wherein $R_2$ is —$CH_3$. In another embodiment is a compound of Formula (II), wherein $R_2$ is —$CH_2CH_3$. In another embodiment is a compound of Formula (IIb), wherein $R_2$ is $C_1$-$C_6$alkyl-$OR_6$. In another embodiment is a compound of Formula (IIb), wherein $R_2$ is $C_1$-$C_6$alkyl-OH. In another embodiment is a compound of Formula (IIb), wherein $R_2$ is $C_1$-$C_6$alkyl$C_3$-$C_6$cycloalkyl. In another embodiment is a compound of Formula (IIb), wherein $R_2$ is —$CH_2$—$C_3$-$C_6$cycloalkyl. In another embodiment is a compound of Formula (IIb), wherein $R_2$ is —$CH_2$-cyclopropyl. In another embodiment is a compound of Formula (IIb), wherein $R_2$ is —$CH_2$-cyclobutyl. In another embodiment is a compound of Formula (IIb), wherein $R_2$ is —$CH_2$-cyclopentyl. In another embodiment is a compound of Formula (IIb), wherein $R_2$ is —$CH_2$— cyclohexyl. In another embodiment is a compound of Formula (IIb), wherein $R_2$ is $C_1$-$C_6$alkyl-$CO_2R_6$. In another embodiment is a compound of Formula (IIb), wherein $R_2$ is $C_1$-$C_6$alkyl-$CO_2CH_3$. In another embodiment is a compound of Formula (IIb), wherein $R_2$ is $C_1$-$C_6$alkyl-$CO_2CH_2CH_3$.

In another embodiment is a compound of Formula (IIb), wherein $R_{2a}$ is $C_1$-$C_6$alkyl. In a further embodiment is a compound of Formula (IIb), wherein $R_{2a}$ is —$CH_3$. In another embodiment is a compound of Formula (IIb), wherein $R_{2a}$ is —$CH_2CH_3$. In another embodiment is a compound of Formula (IIb), wherein $R_{2a}$ is $C_1$-$C_6$alkyl-$OR_5$. In another embodiment is a compound of Formula (IIb), wherein $R_{2a}$ is $C_1$-$C_6$alkyl-OH. In another embodiment is a compound of Formula (IIb), wherein $R_{2a}$ is $C_1$-$C_6$alkyl$C_3$-$C_6$cycloalkyl. In another embodiment is a compound of Formula (IIb), wherein $R_{2a}$ is —$CH_2$—$C_3$-$C_6$cycloalkyl. In another embodiment is a compound of Formula (IIb), wherein $R_{2a}$ is —$CH_2$-cyclopropyl. In another embodiment is a compound of Formula (IIb), wherein $R_{2a}$ is —$CH_2$-cyclobutyl. In another embodiment is a compound of Formula (IIb), wherein $R_{2a}$ is —$CH_2$-cyclopentyl. In another embodiment is a compound of Formula (IIb), wherein $R_{2a}$ is —$CH_2$-cyclohexyl.

In another embodiment is a compound of Formula (IIb), wherein $R_2$ is $C_1$-$C_6$alkyl and $R_{2a}$ is $C_1$-$C_6$alkyl. In another embodiment is a compound of Formula (IIb), wherein $R_2$ is —$CH_3$ and $R_{2a}$ is —$CH_3$. In another embodiment is a compound of Formula (IIb), wherein $R_2$ is —$CH_2CH_3$ and $R_{2a}$ is —$CH_3$. In another embodiment is a compound of Formula (IIb), wherein $R_2$ is —$C_1$-$C_6$alkyl-$OR_6$ and $R_{2a}$ is $C_1$-$C_6$alkyl. In another embodiment is a compound of Formula (IIb), wherein $R_2$ is —$C_1$-$C_6$alkyl-OH and $R_{2a}$ is $C_1$-$C_6$alkyl. In another embodiment is a compound of Formula (IIb), wherein $R_2$ is —$C_1$-$C_6$alkyl-OH and $R_{2a}$ is —$CH_3$. In another embodiment is a compound of Formula (IIb), wherein $R_2$ is —$C_1$-$C_6$alkyl$C_3$-$C_6$cycloalkyl and $R_{2a}$ is $C_1$-$C_6$alkyl. In another embodiment is a compound of Formula (IIb), wherein $R_2$ is —$C_1$-$C_6$alkyl$C_3$-$C_6$cycloalkyl and $R_{2a}$ is —$CH_3$. In another embodiment is a compound of Formula (IIb), wherein $R_2$ is —$CH_2$—$C_3$-$C_6$cycloalkyl and $R_{2a}$ is —$CH_3$. In another embodiment is a compound of Formula (IIb), wherein $R_2$ is —$C_1$-$C_6$alkyl-$CO_2R_6$ and $R_{2a}$ is $C_1$-$C_6$alkyl. In another embodiment is a compound of Formula (IIb), wherein $R_2$ is —$C_1$-$C_6$alkyl-$CO_2CH_3$ and $R_{2a}$ is —$CH_3$.

In another embodiment is a compound of Formula (IIb), wherein Z is a single bond. In another embodiment is a compound of Formula (IIb), wherein Z is a double bond. In another embodiment is a compound of Formula (IIb), wherein Z is —$CH_2$—. In another embodiment is a compound of Formula (IIb), wherein Z is —O—.

In another embodiment is a compound of Formula (IIb), wherein $X^-$ is $Cl^-$. In another embodiment is a compound of Formula (IIb), wherein $X^-$ is $Br^-$. In another embodiment is a compound of Formula (IIb), wherein $X^-$ is $I^-$. In another embodiment is a compound of Formula (IIb), wherein $X^-$ is $CF_3CO_2^-$. In another embodiment is a compound of Formula (IIb), wherein X is $Cl^-$, $Br^-$, $I^-$, or $CF_3CO_2^-$.

In another embodiment is a compound of Formula (IIb), having the structure of Formula (IIb'):

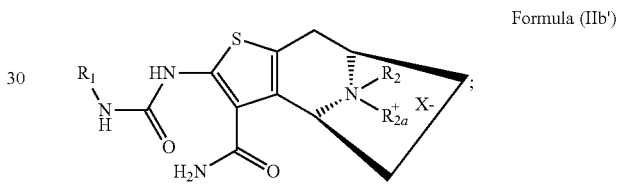

Formula (IIb')

wherein:
$X^-$ is a counterion;
$R_1$ is aryl or heteroaryl, wherein aryl and heteroaryl are optionally substituted with one or more $R_4$;
$R_{2a}$ is $C_1$-$C_6$alkyl, —$C_1$-$C_6$alkyl-$OR_5$, or —$C_1$-$C_6$alkyl$C_3$-$C_6$cycloalkyl;
$R_2$ is $C_1$-$C_6$alkyl, —$C_1$-$C_6$alkyl-$OR_6$, —$C_1$-$C_6$alkyl$C_3$-$C_6$cycloalkyl, or —$C_1$-$C_6$alkyl-$CO_2R_6$;
each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, aryl, and heteroaryl;
$R_5$ is H, or $C_1$-$C_6$alkyl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl; and
$R_{10}$ is $C_1$-$C_6$alkyl, $C_3$-$C_6$cycloalkyl, $C_2$-$C_7$heterocycloalkyl, aryl, heteroaryl, —$C_1$-$C_6$alkylaryl, or —$C_1$-$C_6$alkylheteroaryl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (IIb'), wherein $R_1$ is aryl optionally substituted with one or more $R_4$. In another embodiment is a compound of Formula (IIb'), wherein $R_1$ is phenyl optionally substituted with one or more $R_4$. In another embodiment is a compound of Formula (IIb'), wherein $R_1$ is phenyl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (IIb'), wherein $R_1$ is phenyl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (IIb'), wherein $R_1$ is 4-chlorophenyl.

In another embodiment is a compound of Formula (IIb') wherein $R_1$ is heteroaryl optionally substituted with one or more $R_4$. In another embodiment is a compound of Formula (IIb'), wherein $R_1$ is heteroaryl substituted with one or more $R_4$, wherein each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, C$_1$-C$_6$alkyl, and C$_1$-C$_6$haloalkyl. In another embodiment is a compound of Formula (IIb'), wherein $R_1$ is heteroaryl substituted with one or more $R_4$, wherein each $R_4$ is independently selected F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (IIb'), wherein heteroaryl is pyridyl.

In another embodiment is a compound of Formula (IIb'), wherein $R_2$ is C$_1$-C$_6$alkyl. In a further embodiment is a compound of Formula (IIb'), wherein $R_2$ is —CH$_3$. In another embodiment is a compound of Formula (II), wherein $R_2$ is —CH$_2$CH$_3$. In another embodiment is a compound of Formula (IIb'), wherein $R_2$ is C$_1$-C$_6$alkyl-OR$_6$. In another embodiment is a compound of Formula (IIb'), wherein $R_2$ is C$_1$-C$_6$alkyl-OH. In another embodiment is a compound of Formula (IIb'), wherein $R_2$ is C$_1$-C$_6$alkylC$_3$-C$_6$cycloalkyl. In another embodiment is a compound of Formula (IIb'), wherein $R_2$ is —CH$_2$—C$_3$-C$_6$cycloalkyl. In another embodiment is a compound of Formula (IIb'), wherein $R_2$ is —CH$_2$-cyclopropyl. In another embodiment is a compound of Formula (IIb'), wherein $R_2$ is —CH$_2$-cyclobutyl. In another embodiment is a compound of Formula (IIb'), wherein $R_2$ is —CH$_2$-cyclopentyl. In another embodiment is a compound of Formula (IIb'), wherein $R_2$ is —CH$_2$—cyclohexyl. In another embodiment is a compound of Formula (IIb'), wherein $R_2$ is C$_1$-C$_6$alkyl-CO$_2$R$_6$. In another embodiment is a compound of Formula (IIb'), wherein $R_2$ is C$_1$-C$_6$alkyl-CO$_2$CH$_3$. In another embodiment is a compound of Formula (IIb'), wherein $R_2$ is C$_1$-C$_6$alkyl-CO$_2$CH$_2$CH$_3$.

In another embodiment is a compound of Formula (IIb'), wherein $R_{2a}$ is C$_1$-C$_6$alkyl. In a further embodiment is a compound of Formula (IIb'), wherein $R_{2a}$ is —CH$_3$. In another embodiment is a compound of Formula (IIb'), wherein $R_{2a}$ is —CH$_2$CH$_3$. In another embodiment is a compound of Formula (IIb'), wherein $R_{2a}$ is C$_1$-C$_6$alkyl-OR$_5$. In another embodiment is a compound of Formula (IIb'), wherein $R_{2a}$ is C$_1$-C$_6$alkyl-OH. In another embodiment is a compound of Formula (IIb'), wherein $R_{2a}$ is C$_1$-C$_6$alkylC$_3$-C$_6$cycloalkyl. In another embodiment is a compound of Formula (IIb'), wherein $R_{2a}$ is —CH$_2$—C$_3$-C$_6$cycloalkyl. In another embodiment is a compound of Formula (IIb'), wherein $R_{2a}$ is —CH$_2$-cyclopropyl. In another embodiment is a compound of Formula (IIb'), wherein $R_{2a}$ is —CH$_2$-cyclobutyl. In another embodiment is a compound of Formula (IIb'), wherein $R_{2a}$ is —CH$_2$-cyclopentyl. In another embodiment is a compound of Formula (IIb'), wherein $R_{2a}$ is —CH$_2$-cyclohexyl.

In another embodiment is a compound of Formula (IIb'), wherein $R_2$ is C$_1$-C$_6$alkyl and $R_{2a}$ is C$_1$-C$_6$alkyl. In another embodiment is a compound of Formula (IIb'), wherein $R_2$ is —CH$_3$ and $R_{2a}$ is —CH$_3$. In another embodiment is a compound of Formula (IIb'), wherein $R_2$ is —CH$_2$CH$_3$ and $R_{2a}$ is —CH$_3$. In another embodiment is a compound of Formula (IIb'), wherein $R_2$ is —C$_1$-C$_6$alkyl-OR$_6$ and $R_{2a}$ is C$_1$-C$_6$alkyl. In another embodiment is a compound of Formula (IIb'), wherein $R_2$ is —C$_1$-C$_6$alkyl-OH and $R_{2a}$ is C$_1$-C$_6$alkyl. In another embodiment is a compound of Formula (IIb'), wherein $R_2$ is —C$_1$-C$_6$alkyl-OH and $R_{2a}$ is —CH$_3$. In another embodiment is a compound of Formula (IIb'), wherein $R_2$ is —C$_1$-C$_6$alkylC$_3$-C$_6$cycloalkyl and $R_{2a}$ is C$_1$-C$_6$alkyl. In another embodiment is a compound of Formula (IIb'), wherein $R_2$ is —C$_1$-C$_6$alkylC$_3$-C$_6$cycloalkyl and $R_{2a}$ is —CH$_3$. In another embodiment is a compound of Formula (IIb'), wherein $R_2$ is —CH$_2$—C$_3$-C$_6$cycloalkyl and $R_{2a}$ is —CH$_3$. In another embodiment is a compound of Formula (IIb'), wherein $R_2$ is —C$_1$-C$_6$alkyl-CO$_2$R$_6$ and $R_{2a}$ is C$_1$-C$_6$alkyl. In another embodiment is a compound of Formula (IIb'), wherein $R_2$ is —C$_1$-C$_6$alkyl-CO$_2$CH$_3$ and $R_{2a}$ is —CH$_3$.

In another embodiment is a compound of Formula (IIb'), wherein X$^-$ is Cl$^-$. In another embodiment is a compound of Formula (IIb'), wherein X$^-$ is Br$^-$. In another embodiment is a compound of Formula (IIb'), wherein X$^-$ is I$^-$. In another embodiment is a compound of Formula (IIb'), wherein X$^-$ is CF$_3$CO$_2$$^-$. In another embodiment is a compound of Formula (IIb'), wherein X$^-$ is Cl$^-$, Br$^-$, I$^-$, or CF$_3$CO$_2$$^-$.

In another embodiment is a compound of Formula (IIb), having the structure of Formula (IIb"):

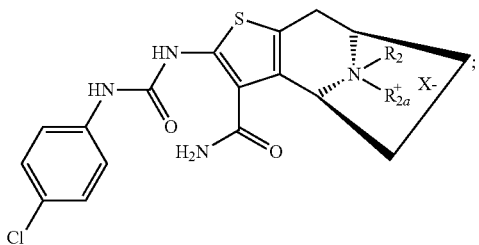

Formula (IIb")

wherein:
X$^-$ is a counterion;
$R_{2a}$ is C$_1$-C$_6$alkyl;
$R_2$ is C$_1$-C$_6$alkyl, —C$_1$-C$_6$alkyl-OR$_6$, —C$_1$-C$_6$alkylC$_3$-C$_6$cycloalkyl, or —C$_1$-C$_6$alkyl-CO$_2$R$_6$; and
$R_6$ is H, or C$_1$-C$_6$alkyl;
or a pharmaceutically acceptable salt, pharmaceutically acceptable solvate or hydrate, pharmaceutically acceptable salt hydrate, or pharmaceutically acceptable prodrug thereof.

In one embodiment is a compound of Formula (IIb"), wherein $R_2$ is C$_1$-C$_6$alkyl. In a further embodiment is a compound of Formula (IIb"), wherein $R_2$ is —CH$_3$. In another embodiment is a compound of Formula (IIb"), wherein $R_2$ is —CH$_2$CH$_3$. In another embodiment is a compound of Formula (IIb"), wherein $R_2$ is C$_1$-C$_6$alkyl-OR$_6$. In another embodiment is a compound of Formula (IIb"), wherein $R_2$ is C$_1$-C$_6$alkyl-OH. In another embodiment is a compound of Formula (IIb"), wherein $R_2$ is C$_1$-C$_6$alkylC$_3$-C$_6$cycloalkyl. In another embodiment is a compound of Formula (IIb"), wherein $R_2$ is —CH$_2$—C$_3$-C$_6$cycloalkyl. In another embodiment is a compound of Formula (IIb"), wherein $R_2$ is —CH$_2$-cyclopropyl. In another embodiment is a compound of Formula (IIb"), wherein $R_2$ is —CH$_2$-cyclobutyl. In another embodiment is a compound of Formula (IIb"), wherein $R_2$ is —CH$_2$-cyclopentyl. In another embodiment is a compound of Formula (IIb"), wherein $R_2$ is —CH$_2$— cyclohexyl. In another embodiment is a compound of Formula (IIb"), wherein $R_2$ is $C_1$-$C_6$alkyl-$CO_2R_6$. In another embodiment is a compound of Formula (IIb"), wherein $R_2$ is $C_1$-$C_6$alkyl-$CO_2CH_3$. In another embodiment is a compound of Formula (IIb"), wherein $R_2$ is $C_1$-$C_6$alkyl-$CO_2CH_2CH_3$.

In another embodiment is a compound of Formula (IIb"), wherein $R_{2a}$ is $C_1$-$C_6$alkyl. In a further embodiment is a compound of Formula (IIb"), wherein $R_{2a}$ is —$CH_3$. In another embodiment is a compound of Formula (IIb"), wherein $R_{2a}$ is —$CH_2CH_3$.

In another embodiment is a compound of Formula (IIb"), wherein $R_2$ is $C_1$-$C_6$alkyl and $R_{2a}$ is $C_1$-$C_6$alkyl. In another embodiment is a compound of Formula (IIb"), wherein $R_2$ is —$CH_3$ and $R_{2a}$ is —$CH_3$. In another embodiment is a compound of Formula (IIb"), wherein $R_2$ is —$CH_2CH_3$ and $R_{2a}$ is —$CH_3$. In another embodiment is a compound of Formula (IIb"), wherein $R_2$ is —$C_1$-$C_6$alkyl-$OR_6$ and $R_{2a}$ is $C_1$-$C_6$alkyl. In another embodiment is a compound of Formula (IIb"), wherein $R_2$ is —$C_1$-$C_6$alkyl-OH and $R_{2a}$ is $C_1$-$C_6$alkyl. In another embodiment is a compound of Formula (IIb"), wherein $R_2$ is —$C_1$-$C_6$alkyl-OH and $R_{2a}$ is —$CH_3$. In another embodiment is a compound of Formula (IIb"), wherein $R_2$ is —$C_1$-$C_6$alkyl$C_3$-$C_6$cycloalkyl and $R_{2a}$ is $C_1$-$C_6$alkyl. In another embodiment is a compound of Formula (IIb"), wherein $R_2$ is —$C_1$-$C_6$alkyl$C_3$-$C_6$cycloalkyl and $R_{2a}$ is —$CH_3$. In another embodiment is a compound of Formula (IIb"), wherein $R_2$ is —$CH_2$—$C_3$-$C_6$cycloalkyl and $R_{2a}$ is —$CH_3$. In another embodiment is a compound of Formula (IIb"), wherein $R_2$ is —$C_1$-$C_6$alkyl-$CO_2R_6$ and $R_{2a}$ is $C_1$-$C_6$alkyl. In another embodiment is a compound of Formula (IIb"), wherein $R_2$ is —$C_1$-$C_6$alkyl-$CO_2CH_3$ and $R_{2a}$ is —$CH_3$.

In another embodiment is a compound of Formula (IIb"), wherein $X^-$ is $Cl^-$. In another embodiment is a compound of Formula (IIb"), wherein $X^-$ is $Br^-$. In another embodiment is a compound of Formula (IIb"), wherein $X^-$ is $I^-$. In another embodiment is a compound of Formula (IIb"), wherein $X^-$ is $CF_3CO_2^-$. In another embodiment is a compound of Formula (IIb"), wherein $X^-$ is $Cl^-$, $Br^-$, $I^-$, or $CF_3CO_2^-$.

In some embodiments is a compound having the structure:

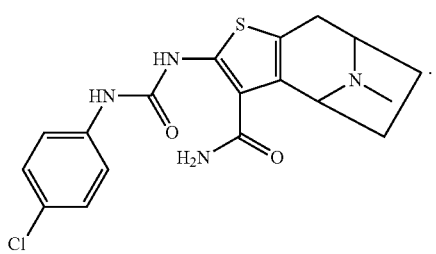 [SMILES: CN1C2CCC1c1c(sc(NC(=O)Nc3ccc(Cl)cc3)c1C(N)=O)C2]

In some embodiments is a compound having the structure:

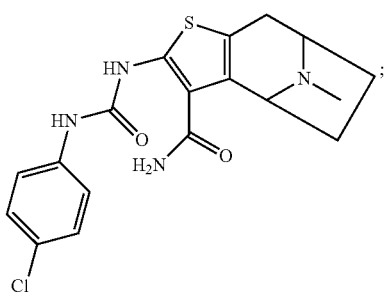 [SMILES: CN1C2CCC1c1c(sc(NC(=O)Nc3ccc(Cl)cc3)c1C(N)=O)C2]

or a pharmaceutically acceptable salt, pharmaceutically acceptable solvate or hydrate, pharmaceutically acceptable salt hydrate, or pharmaceutically acceptable prodrug thereof.

In some embodiments is a compound having the structure:

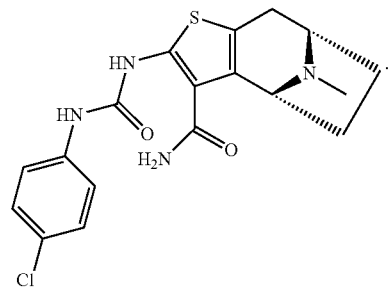

In some embodiments is a compound having the structure:

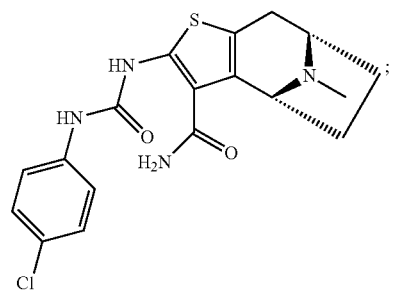

or a pharmaceutically acceptable salt, pharmaceutically acceptable solvate or hydrate, pharmaceutically acceptable salt hydrate, or pharmaceutically acceptable prodrug thereof.

In some embodiments is a compound having the structure:

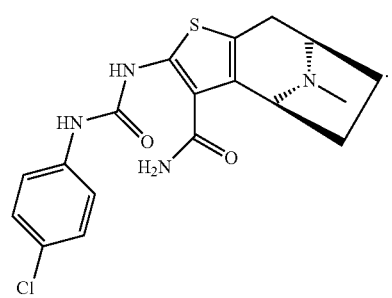

In some embodiments is a compound having the structure:

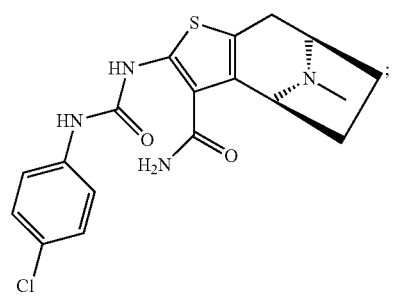

or a pharmaceutically acceptable salt, pharmaceutically acceptable solvate or hydrate, pharmaceutically acceptable salt hydrate, or pharmaceutically acceptable prodrug thereof.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

In some embodiments, described herein, the process for the preparation of (4R,7S)-2-(3-(4-chlorophenyl)ureido)-9-methyl-5,6,7,8-tetrahydro-4H-4,7-epiminocyclohepta[b]thiophene-3-carboxamide hydrochloride, is outlined in Scheme 1:

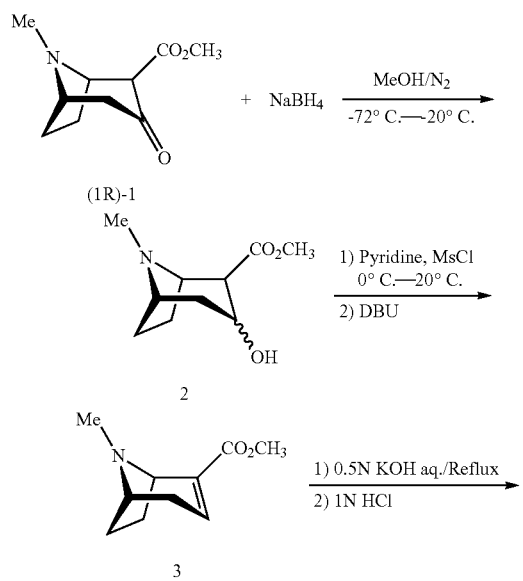

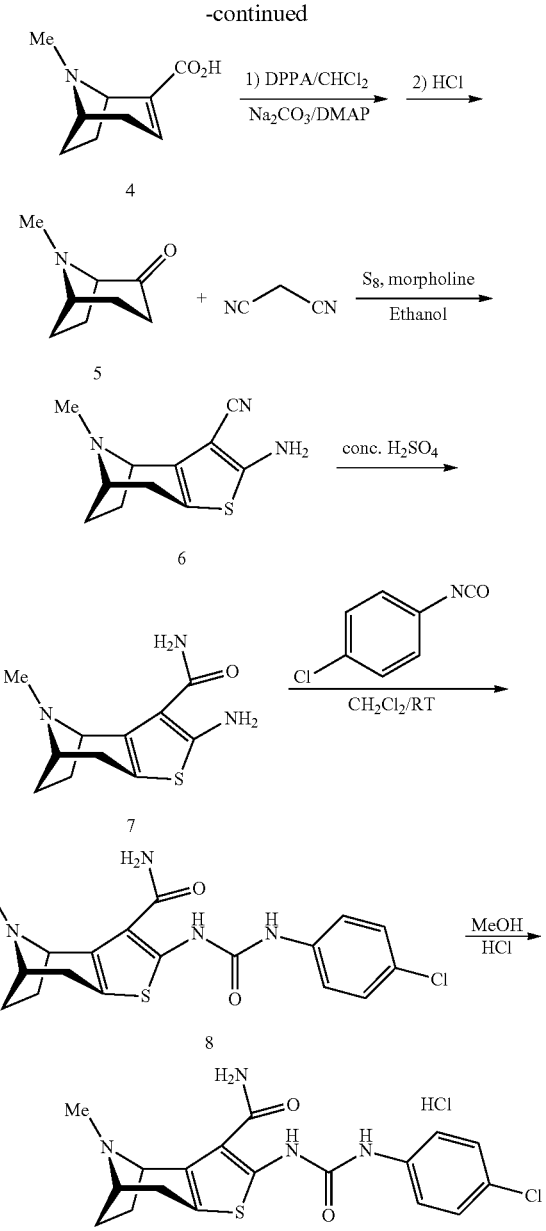

In another aspect, described herein, the process for the preparation of (4R,7S)-2-(3-(4-chlorophenyl)ureido)-9-methyl-5,6,7,8-tetrahydro-4H-4,7-epiminocyclohepta[b]thiophene-3-carboxamide hydrochloride, comprises:

A) the reaction of a compound with the structure

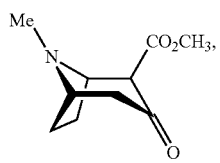

with sodium borohydride in the presence of a solvent to produce a compound with the structure

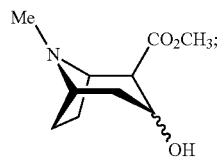

B) followed by the reaction of the compound with the structure

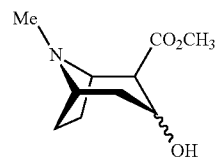

with pyridine and methanesulfonyl chloride in the presence of a solvent, followed by treatment with 1,8-diazabicyclo[5.4.0]undec-7-ene (DBU) to produce a compound with the structure

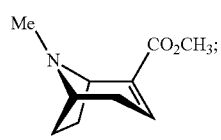

C) followed by the reaction of the compound with the structure

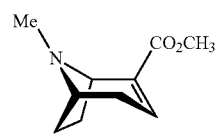

with an aqueous base and then an acid to produce a compound with the structure

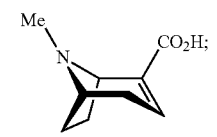

D) followed by the reaction of the compound with the structure

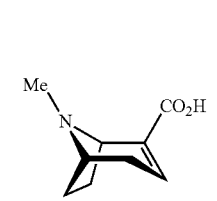

with sodium carbonate, 4-dimethylaminopyridine (DMAP), and diphenyl phosphoryl azide (DPPA) in the presence of a solvent followed by treatment with an acid to produce a compound with the structure

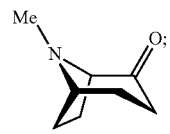

E) followed by the reaction of the compound with the structure

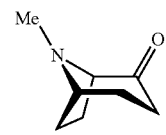

with malononitrile, sulfur, and morpholine to produce a compound with the structure

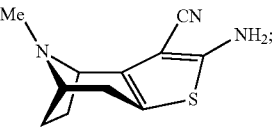

F) followed by the reaction of the compound with the structure

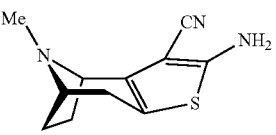

with concentrated sulfuric acid to produce a compound with the structure

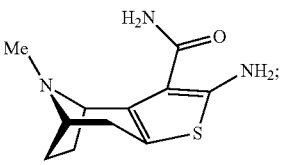

G) followed by the reaction of the compound with the structure

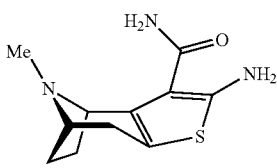

with 4-chlorophenyl isocyanate in the presence of a solvent to produce a compound with the structure

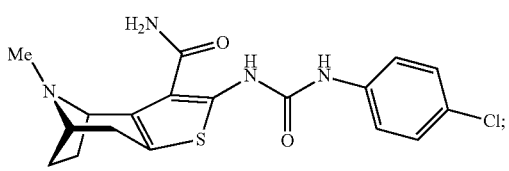

H) followed by the reaction of the compound with the structure

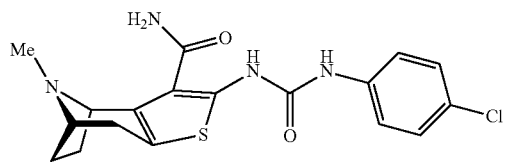

with hydrochloric acid in the presence of a solvent produce (4R,7S)-2-(3-(4-chlorophenyl)ureido)-9-methyl-5,6,7,8-tetrahydro-4H-4,7-epiminocyclohepta[b]thiophene-3-carboxamide hydrochloride having the structure

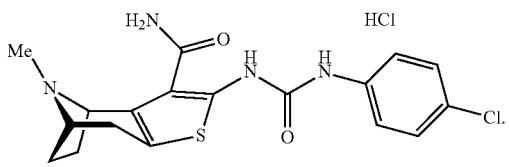

In some embodiments of the process of Scheme 1, the base is selected from MOH, $M_2CO_3$, and $MHCO_3$ wherein M is selected from lithium, sodium, potassium, and cesium; 1,8-diazabicyclo[5.4.0]undec-7-ene (DBU), $R_1R_2R_3N$ wherein $R_1$, $R_2$, and $R_3$ are each independently $C_1$-$C_6$alkyl. In some embodiments of the process of Scheme 1, the base is MOH. In some embodiments of the process of Scheme 1, the base is NaOH. In some embodiments of the process of Scheme 1, the base is KOH. In some embodiments of the process of Scheme 1, the base is 1,8-diazabicyclo[5.4.0]undec-7-ene (DBU). In some embodiments of the process of Scheme 1, the base is $R_1R_2R_3N$ wherein $R_1$, $R_2$, and $R_3$ are each independently $C_1$-$C_6$alkyl. In some embodiments of the process of Scheme 1, the base is $R_1R_2R_3N$ wherein $R_1$, $R_2$, and $R_3$ are each ethyl. In some embodiments of the process of Scheme 1, the base is $R_1R_2R_3N$ wherein $R_1$ and $R_2$ are isopropyl and $R_3$ is ethyl.

In some embodiments of the process of Scheme 1, the acid is an inorganic acid. In some embodiments of the process of Scheme 1, the acid is an inorganic acid wherein the inorganic acid is hydrochloric acid, hydrobromic acid, sulfuric acid, phosphoric acid, or metaphosphoric acid. In some embodiments of the process of Scheme 1, the acid is an inorganic acid wherein the inorganic acid is hydrochloric acid. In some embodiments of the process of Scheme 1, the acid is an inorganic acid wherein the inorganic acid is hydrobromic acid. In some embodiments of the process of Scheme 1, the acid is an inorganic acid wherein the inorganic acid is sulfuric acid. In some embodiments of the process of Scheme 1, the acid is an inorganic acid wherein the inorganic acid is phosphoric acid. In some embodiments of the process of Scheme 1, the acid is an inorganic acid wherein the inorganic acid is metaphosphoric acid.

In some embodiments of the process of Scheme 1, the acid is an organic acid. In some embodiments of the process of Scheme 1, the acid is an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid.

In some embodiments of the process of Scheme 1, the solvent is selected from water, $C_1$-$C_6$alcohol, tetrahydrofuran, 2-methyltetrahyrofuran, toluene, dichloromethane, dichloroethane, and mixtures thereof. In some embodiments of the process of Scheme 1, the solvent is water. In some embodiments of the process of Scheme 1, the solvent is $C_1$-$C_6$alcohol. In some embodiments of the process of Scheme 1, the solvent is methanol. In some embodiments of the process of Scheme 1, the solvent is isopropanol. In some embodiments of the process of Scheme 1, the solvent is tetrahydrofuran. In some embodiments of the process of Scheme 1, the solvent is 2-methyltetrahyrofuran. In some embodiments of the process of Scheme 1, the solvent is toluene. In some embodiments of the process of Scheme 1, the solvent is dichloromethane. In some embodiments of the process of Scheme 1, the solvent is dichloroethane.

In some embodiments, described herein, the process for the preparation of (4R,7S)-2-(3-(4-chlorophenyl)ureido)-9-methyl-5,6,7,8-tetrahydro-4H-4,7-epiminocyclohepta[b]thiophene-3-carboxamide hydrochloride, is outlined in Scheme 2:

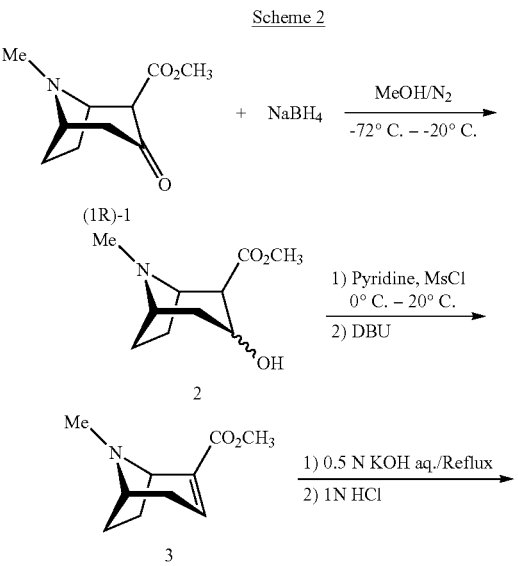

-continued

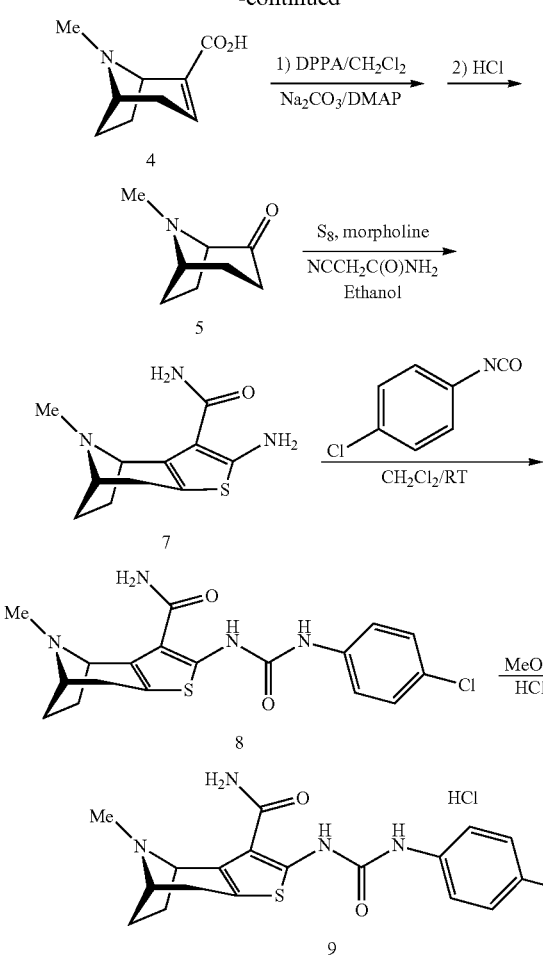

In another aspect, described herein, the process for the preparation of (4R,7S)-2-(3-(4-chlorophenyl)ureido)-9-methyl-5,6,7,8-tetrahydro-4H-4,7-epiminocyclohepta[b]thiophene-3-carboxamide hydrochloride, comprises:

A) the reaction of a compound with the structure

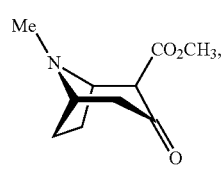

with sodium borohydride in the presence of a solvent to produce a compound with the structure

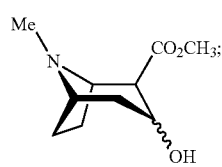

B) followed by the reaction of the compound with the structure

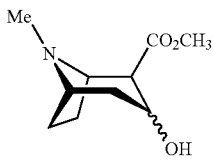

with pyridine and methanesulfonyl chloride in the presence of a solvent, followed by treatment with 1,8-diazabicyclo[5.4.0]undec-7-ene (DBU) to produce a compound with the structure

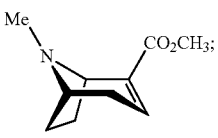

C) followed by the reaction of the compound with the structure

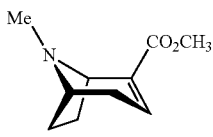

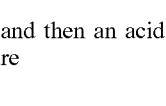

with an aqueous base and then an acid to produce a compound with the structure

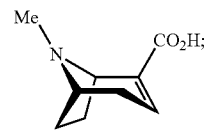

D) followed by the reaction of the compound with the structure

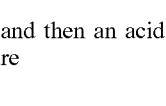

with sodium carbonate, 4-dimethylaminopyridine (DMAP), and diphenyl phosphoryl azide (DPPA) in the presence of a solvent followed by treatment with an acid to produce a compound with the structure

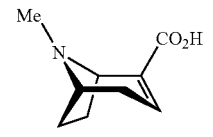

E) followed by the reaction of the compound with the structure

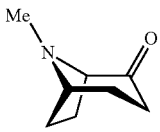

with NCCH₂C(O)NH₂, sulfur, and morpholine to produce a compound with the structure

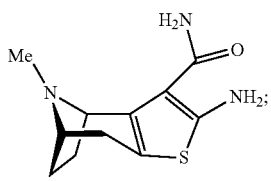

F) followed by the reaction of the compound with the structure

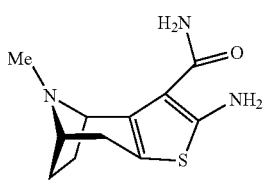

with 4-chlorophenyl isocyanate in the presence of a solvent to produce a compound with the structure

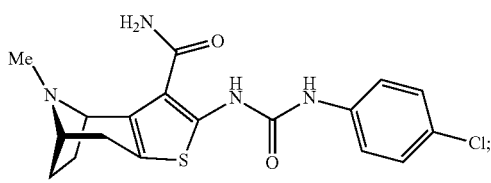

G) followed by the reaction of the compound with the structure

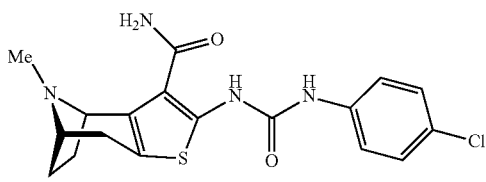

with hydrochloric acid in the presence of a solvent produce (4R,7S)-2-(3-(4-chlorophenyl)ureido)-9-methyl-5,6,7,8-tetrahydro-4H-4,7-epiminocyclohepta[b]thiophene-3-carboxamide hydrochloride having the structure

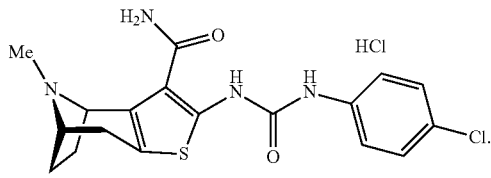

In some embodiments of the process of Scheme 2, the base is selected from MOH, $M_2CO_3$, and $MHCO_3$ wherein M is selected from lithium, sodium, potassium, and cesium; 1,8-diazabicyclo[5.4.0]undec-7-ene (DBU), $R_1R_2R_3N$ wherein $R_1$, $R_2$, and $R_3$ are each independently $C_1$-$C_6$alkyl. In some embodiments of the process of Scheme 2, the base is MOH. In some embodiments of the process of Scheme 2, the base is NaOH. In some embodiments of the process of Scheme 2, the base is KOH. In some embodiments of the process of Scheme 2, the base is 1,8-diazabicyclo[5.4.0]undec-7-ene (DBU). In some embodiments of the process of Scheme 2, the base is $R_1R_2R_3N$ wherein $R_1$, $R_2$, and $R_3$ are each independently $C_1$-$C_6$alkyl. In some embodiments of the process of Scheme 2, the base is $R_1R_2R_3N$ wherein $R_1$, $R_2$, and $R_3$ are each ethyl. In some embodiments of the process of Scheme 2, the base is $R_1R_2R_3N$ wherein $R_1$ and $R_2$ are isopropyl and $R_3$ is ethyl.

In some embodiments of the process of Scheme 2, the acid is an inorganic acid. In some embodiments of the process of Scheme 2, the acid is an inorganic acid wherein the inorganic acid is hydrochloric acid, hydrobromic acid, sulfuric acid, phosphoric acid, or metaphosphoric acid. In some embodiments of the process of Scheme 2, the acid is an inorganic acid wherein the inorganic acid is hydrochloric acid. In some embodiments of the process of Scheme 2, the acid is an inorganic acid wherein the inorganic acid is hydrobromic acid. In some embodiments of the process of Scheme 2, the acid is an inorganic acid wherein the inorganic acid is sulfuric acid. In some embodiments of the process of Scheme 2, the acid is an inorganic acid wherein the inorganic acid is phosphoric acid. In some embodiments of the process of Scheme 2, the acid is an inorganic acid wherein the inorganic acid is metaphosphoric acid.

In some embodiments of the process of Scheme 2, the acid is an organic acid. In some embodiments of the process of Scheme 2, the acid is an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid.

In some embodiments of the process of Scheme 2, the solvent is selected from water, $C_1$-$C_6$alcohol, tetrahydrofuran, 2-methyltetrahyrofuran, toluene, dichloromethane, dichloroethane, and mixtures thereof. In some embodiments of the process of Scheme 2, the solvent is water. In some embodiments of the process of Scheme 2, the solvent is $C_1$-$C_6$ alcohol. In some embodiments of the process of Scheme 2, the solvent is methanol. In some embodiments of the process of Scheme 2, the solvent is isopropanol. In some embodiments of the process of Scheme 2, the solvent is tetrahydrofuran. In some embodiments of the process of Scheme 2, the solvent is 2-methyltetrahyrofuran. In some embodiments of the process of Scheme 2, the solvent is toluene. In some embodiments of the process of Scheme 2, the solvent is dichloromethane. In some embodiments of the process of Scheme 2, the solvent is dichloroethane.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups are optionally removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and are optionally subsequently removed by metal or pi-acid catalysts. For example, an allyl-blocked carboxylic acid are optionally deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

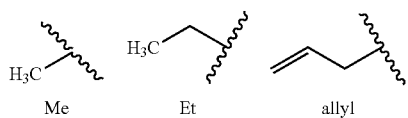

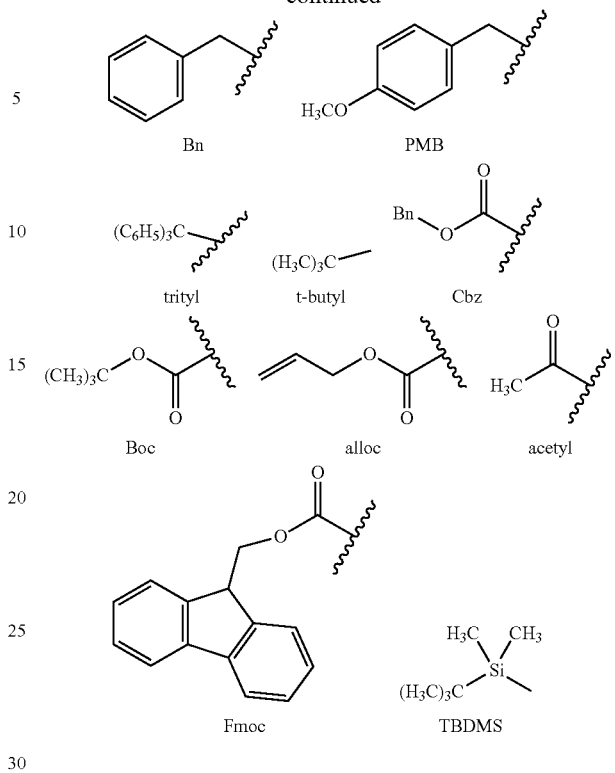

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Pharmaceutical Compositions and Methods of Administration

Pharmaceutical compositions may be formulated in a conventional manner using one or more physiologically acceptable carriers including excipients and auxiliaries which facilitate processing of the active compounds into preparations which are optionally used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

A pharmaceutical composition, as used herein, refers to a mixture of a compound of Formula (I), (Ia), (Ib), (II), (IIa), or (IIb) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount depends on the severity of the disease, the age and relative health of the subject, the potency of the compound used and other factors. The compounds of Formula (I), (Ia), (Ib), (II), (IIa), or (IIb) are optionally used singly or in combination with one or more therapeutic agents as components of mixtures (as in combination therapy).

The pharmaceutical formulations described herein are optionally administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of Formula (I), (Ia), (Ib), (II), (IIa), or (IIb) described herein, are optionally formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (Ia), (Ib), (II), (IIa), or (IIb) described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity. In some situations, compounds may exist as tautomers. All tautomers are included within the scope of the compounds presented herein. Additionally, many of the compounds described herein exist in unsolvated as well as solvated forms with pharmaceutically acceptable solvents such as water, ethanol, and the like. The solvated forms of the compounds presented herein are also considered to be disclosed herein.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use are optionally obtained by mixing one or more solid excipient with one or more of the compounds of Formula (I), (Ia), (Ib), (II), (IIa), or (IIb) described herein, optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that are used orally include push-fit capsules made of gelatin, as well as soft, sealed capsules made of gelatin and a plasticizer, such as glycerol or sorbitol. The push-fit capsules optionally contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula (I), (Ia), (Ib), (II), (IIa), or (IIb) described herein, with one or more pharmaceutical excipients to form a bulk blend composition. When referring to these bulk blend compositions as homogeneous, it is meant that the particles of the compound of Formula (I), (Ia), (Ib), (II), (IIa), or (IIb) described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations are optionally manufactured by conventional pharmacological techniques.

The pharmaceutical solid dosage forms described herein include a compound of Formula (I), (Ia), (Ib), (II), (IIa), or (IIb) described herein, and optionally one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (I), (Ia), (Ib), (II), (IIa), or (IIb) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that are optionally filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol optionally is selected to have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compounds of Formula (I) described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (I) described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Microencapsulated compounds described herein may be formulated by methods that include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

The pharmaceutical solid oral dosage forms including formulations described herein, which include a compound described herein, can be further formulated to provide a controlled release of the compound of Formula (I). Controlled release refers to the release of the compounds described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In other embodiments, the formulations described herein, which include a compound of Formula (I) described herein, are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations including, but are not limited to, those described in U.S. Pat. Nos. 5,011,692; 5,017,381; 5,229,135; 5,840,329; 4,871,549; 5,260,068; 5,260,069; 5,508,040; 5,567,441 and 5,837,284.

Many other types of controlled release systems are suitable for use with the formulations described herein.

Examples of such delivery systems include, e.g., polymer-based systems, such as polylactic and polyglycolic acid, polyanhydrides and polycaprolactone; porous matrices, non-polymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.

In some embodiments, pharmaceutical formulations are provided that include particles of the compounds described herein, e.g. compounds of Formula (I), and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Generally, an agent, such as a compound of Formula (I), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

Methods of Dosing and Treatment Regimens

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compounds of Formula (I), (Ia), (Ib), (II), (IIa), or (IIb) described herein, and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound of Formula (I), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

In some embodiments, a compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered in combination with an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments, a compound of Formula (I), (Ia), (Ib), (II), (IIa), or (IIb) is administered in combination with streptomycin. In some embodiments, a compound of Formula (I), (Ia), (Ib), (II), (IIa), or (IIb) is administered in combination with amikacin. In some embodiments, a compound of Formula (I), (Ia), (Ib), (II), (IIa), or (IIb) is administered in combination with neomycin. In some embodiments, a compound of Formula (I), (Ia), (Ib), (II), (IIa), or (IIb) is administered in combination with kanamycin. In some embodiments, a compound of Formula (I), (Ia), (Ib), (II), (IIa), or (IIb) is administered in combination with gentamicin. In some embodiments, a compound of Formula (I), (Ia), (Ib), (II), (IIa), or (IIb) is administered in combination with tobramycin.

In some embodiments, a compound of Formula (I), (Ia), (Ib), (II), (IIa), or (IIb) is administered for 1-7 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 7 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 6 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 5 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 4 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 3 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 2 days, and then the compound of Formula (I), (Ia), (Ib), (II), (IIa), or (IIb) is administered in combination with an aminoglycoside antibiotic. In some embodiments, a compound of Formula (I), (Ia), (Ib), (II), (IIa), or (IIb) is administered for 1 day, and then the compound of Formula (I), (Ia), (Ib), (II), (IIa), or (IIb) is administered in combination with an aminoglycoside antibiotic. In some embodiments, the compound of Formula (I), (Ia), (Ib), (II), (IIa), or (IIb) is administered an additional 7 days following the administration of the aminoglycoside antibiotic. In some embodiments, the compound of Formula (I), (Ia), (Ib), (II), (IIa), or (IIb) is administered an additional 6 days following the administration of the aminoglycoside antibiotic. In some embodiments, the compound of Formula (I), (Ia), (Ib), (II), (IIa), or (IIb) is administered an additional 5 days following the administration of the aminoglycoside antibiotic. In some embodiments, the compound of Formula (I), (Ia), (Ib), (II), (IIa), or (IIb) is administered an additional 4 days following the administration of the aminoglycoside antibiotic. In some embodiments, the compound of Formula (I), (Ia), (Ib), (II), (IIa), or (IIb) is administered an additional 3 days following the administration of the aminoglycoside antibiotic. In some embodiments, the compound of Formula (I), (Ia), (Ib), (II), (IIa), or (IIb) is administered an additional 2 days following the administration of the aminoglycoside antibiotic. In some embodiments, the compound of Formula (I), (Ia), (Ib), (II), (IIa), or (IIb) is administered an additional 1 day following the administration of the aminoglycoside antibiotic.

In some embodiments the compound of Formula (I), (Ia), (Ib), (II), (IIa), or (IIb) and the aminoglycoside antibiotic are administered in combination in a single dosage form. In some embodiments the compound of Formula (I), (Ia), (Ib), (II), (IIa), or (IIb) and the aminoglycoside antibiotic are administered in combination in separate dosage forms.

In some embodiments, a compound of Formula (I), (Ia), (Ib), (II), (IIa), or (IIb) is administered in combination with a chemotherapeutic agent. In some embodiments, a compound of Formula (I), (Ia), (Ib), (II), (IIa), or (IIb) is administered in combination with a chemotherapeutic agent selected from cisplatin and carboplatin. In some embodiments, a compound of Formula (I), (Ia), (Ib), (II), (IIa), or (IIb) is administered in combination with cisplatin. In some embodiments, a compound of Formula (I), (Ia), (Ib), (II), (IIa), or (IIb) is administered in combination with carboplatin.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I), (Ia), (Ib), (II), (IIa), or (IIb) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary.

Thus, for example, the compounds can be used as a prophylactic and can be administered continuously to subjects with a propensity to develop conditions or diseases in order to prevent the occurrence of the disease or condition. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease or condition. The length of treatment can vary for each subject, and the length can be determined using the known criteria.

EXAMPLES

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm ($\delta$) and coupling constants, J are reported in Hertz. For proton spectra the solvent peak was used as the reference peak.

Example 1: Preparation of 2-[3-(4-chlorophenyl)ureido]-6-(cyclopropylmethyl)-4,5,6,7-tetrahydrothieno[2,3-c]pyridine-3-carboxamide hydrochloride (9)

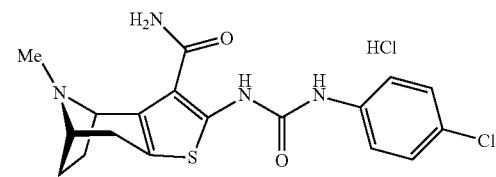

Step 1: (5S)-methyl 3-hydroxy-8-methyl-8-azabicyclo[3.2.1]octane-2-carboxylate (2)

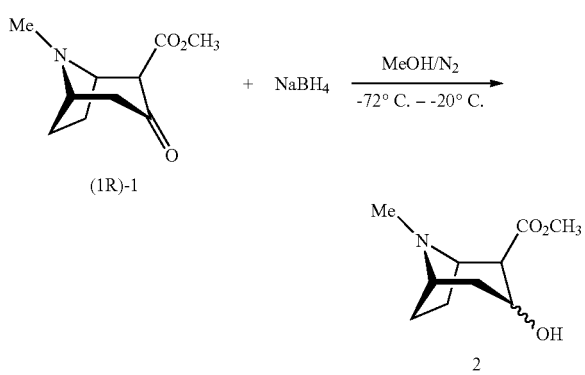

To a 3 L round bottom flask equipped with a magnetic stir bar and nitrogen inlet was added (R)-2-Carbomethoxy-3- tropinone 1 (50 g, 254 mmol) and methanol (1.01 L). The resulting mixture was stirred rapidly at room temperature (20±2° C.) under nitrogen for one hour to give a brown clear solution, which was cooled to −72° C. (internal temperature) in a dry ice-acetone bath with continuing stirring under nitrogen. Sodium borohydride (24 g, 635 mmol) was added in one portion and the reaction mixture was first stirred at −72° C. (internal temperature) under nitrogen for 30 minutes, and then moved into another cooling bath that was filled with ethanol and pre-cooled to −20° C. (internal temperature) with an immersion cooler. The reaction was stirred at −20° C. under nitrogen for 16 hours.

With rapid stirring under nitrogen, the reaction mixture was cooled again to −72° C. (internal temperature). The nitrogen inlet on the reaction flask was replaced with a Claisen adapter. One joint of the Claisen adapter was connected to the nitrogen inlet. On the other joint of the Claisen adapter was put an addition funnel capped with a septum and containing conc. HCl (115 mL). While stirring rapidly under nitrogen at −72° C., the reaction was quenched by adding conc. HCl dropwise over a period of 45 minutes. After addition was completed, the resulting light yellow slurry was warmed gradually to room temperature (20±2° C.) over one hour, and then concentrated under reduced pressure (Rotovap at 40° C. bath temperature) to give a yellow oily solid. To the 3 L round bottom flask containing the yellow oily solid residue was added brine (850 mL) in one portion and the resulting light brown solution was cooled to 0-5° C. with an ice-water bath. The 3 L round bottom flask was equipped again with a Claisen adapter, nitrogen inlet and an addition funnel containing conc. ammonium hydroxide (140 mL). With ice-water bath cooling and rapid stirring, ammonium hydroxide was dropped into the above light brown solution to adjust the pH value to about 10 over a period of 30 minutes. The aqueous solution was then extracted with methylene dichloride (950 ml×3), and the combined organic phases were dried over $Na_2SO_4$. Filtration, concentration (Rotovap at 40° C. bath temperature) and drying under high vacuum (oil pump) for 16 hours gave a light brown oily solid product 2 (41.5 g, 82%) which is a mixture of 3-hydroxytropanes.

Step 2: (5S)-methyl 8-methyl-8-azabicyclo[3.2.1]oct-2-ene-2-carboxylate (3)

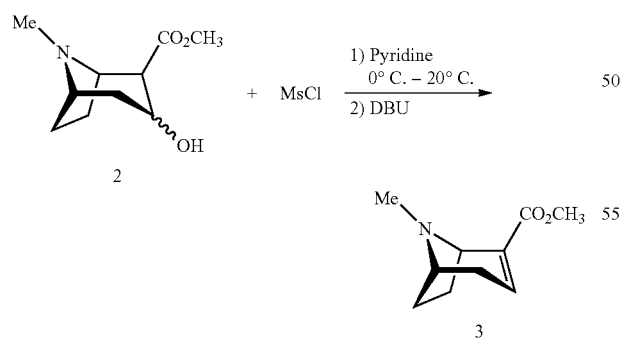

To an oven-dried 2 L round bottom flask equipped with a magnetic stirring bar and nitrogen inlet was added at room temperature (20±2° C.) compound 2 (41.5 g, 208 mmol) and anhydrous pyridine (414 mL) to form a dark red solution, which was then cooled in an ice-water bath with stirring for 30 minutes. To the above stirred solution was dropped in methanesulfonyl chloride (38.3 mL, 500 mmol) via a sealed addition funnel over 15 minutes. The resulting mixture was stirred for another 30 minutes with ice-water bath cooling. The ice-water bath was then removed and the reaction mixture was stirred at room temperature (20±2° C.) under $N_2$ for 48 hours. The reaction flask was again cooled in an ice-water bath for 25 minutes. 1,8-Diazabicyclo[5.4.0]undec-7-ene (DBU) (156 mL, 1040 mmol) was dropped into the reaction mixture via a sealed addition funnel over 40 minutes. After addition finished, the stirring was continued for another 30 minutes. The ice-water bath was then removed and the reaction mixture was stirred at room temperature (20±2° C.) under $N_2$ for 24 hours.

The reaction mixture was carefully added to a 5 L round bottom flask charged with a magnetic stirring bar and diethyl ether (2.5 L) over 15 minutes with vigorously stirring. After addition finished, stirring was continued for another 10 min and then stopped. The mixture was left to stand for 40 min. The dark red ether phase was decanted out and the residue was washed with ether (350 mL×2). All the ether phases were combined and concentrated under reduced pressure (first used low vacuum to remove ether, then used high vacuum to remove most of pyridine) at water bath temperature <45° C. to give dark red oily residue (75 g) that was purified using Teledyne ISCO Combiflash automatic chromatography system (330 g Redisep silica gel column, Solvent A: 1% $Et_3N$/10% MeOH/89% EtOAc in Solvent B: 1% $Et_3N$/99% EtOAc gradient) to give pure product 3 (26.3 g, 70%) as a red oil, plus impure product 3 6.6 g; $^1$H-NMR (300 MHz, $CDCl_3$) δ 6.82-6.78 (m, 1H, H-3), 3.76 (d, J=5.2 Hz, 1H, H-1), 3.72 (s, 3H, $OCH_3$), 3.22 (t, J=5.5 Hz, 1H, H-5), 2.61 (d, J=19.5 Hz, 1H, H-4$_{ax}$), 2.33 (s, 3H, $NCH_3$), 2.21-2.06 (m, 2H), 1.89-1.70 (m, 2H), 1.54-1.41 (m, 1H); CIMS [M+1]$^+$ 182.

Step 3: (5S)-8-methyl-8-azabicyclo[3.2.1]oct-2-ene-2-carboxylic acid (4)

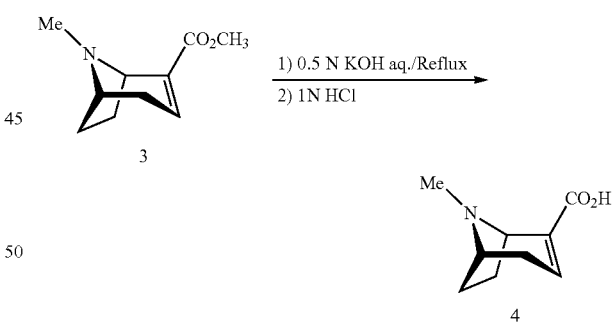

A solution of compound 3 (14.7 g, 81 mmol) in 0.5 N KOH aqueous solution (324 mL, 162 mmol) in a 1 L round bottom flask was heated to reflux (oil bath 135-140° C.) for 40 min. The clear yellow solution was cooled down to room temperature (20±2° C.), then put into an ice-water bath and acidified with 1 N HCl (~160 ml) to pH=6. Concentration under reduced pressure gave a yellow solid, which was extracted with absolute ethanol (400 ml×3). Combined extracts were filtered and concentrated under reduced pressure to give 4 (13 g, 96%) as a light yellow solid; $^1$H-NMR (300 MHz, DMSO-d6) δ 6.58-6.52 (m, 1H, H-3), 3.59 (d, J=5.2 Hz, 1H, H-1), 3.12 (t, J=5.2 Hz, 1H, H-5), 2.52-2.41 (m, 1H, H-4$_{ax}$), 2.20 (s, 3H, $NCH_3$), 2.05-1.88 (m, 2H), 1.76

(dd, J=19.5, 4.4 Hz, 1H, H-4$_{eq}$), 1.66-1.58 (m, 1H), 1.46-1.36 (m, 1H); CIMS [M+1]$^+$ 168.

Step 4: (5S)-8-methyl-8-azabicyclo[3.2.1]octan-2-one (5)

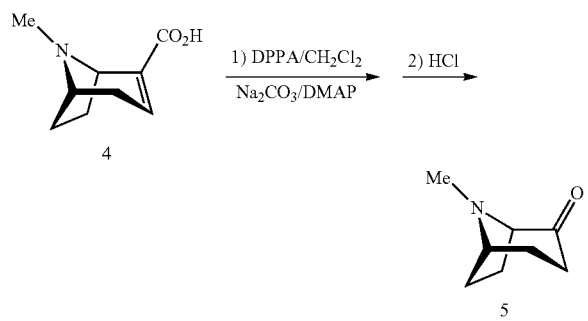

To an oven-dried 2 L round bottom flask equipped with a magnetic stir bar and nitrogen inlet was added compound 4 (13 g, 77.8 mmol), Na$_2$CO$_3$ (11.6 g, 109 mmol) and DMAP (238 mg, 1.9 mmol). Under nitrogen atmosphere, anhydrous methylene dichloride (292 mL) was added to the above flask followed by the addition of diphenyl phosphoryl azide (DPPA) (20.2 mL, 93.4 mmol). The resulted reaction mixture was stirred vigorously at room temperature (20±2° C.) for 65 hours to form an off-white to light yellow slurry. Volatile components were removed under reduced pressure and the residue was dissolved in water (78 mL) followed by the slowly and carefully addition of 1N HCl (340 mL). The mixture was heated to reflux (oil bath 120° C.) for 50 minutes until gas evolution ceased. After concentration under reduced pressure, the residue was brought to basic (pH≈10) with saturated aqueous Na$_2$CO$_3$ solution and extracted with methylene dichloride (500 mL×2) and chloroform (500 mL×2). The combined organic phases were dried over Na$_2$SO$_4$. Filtration and concentration gave yellow liquid residue (14.95 g), which was purified using Teledyne ISCO Combiflash automatic chromatography system (220 g Redisep silica gel column, first eluent with EtOAc in CH$_2$Cl$_2$ gradient, then with 1% Et$_3$N/99% EtOAc in CH$_2$Cl$_2$) to give pure product 5 (6.5 g, 60%) as a slightly yellow oil; $^1$H-NMR (300 MHz, CDCl$_3$) δ 3.34-3.28 (m, 1H, H-5), 3.27 (d, J=6.9 Hz, 1H, H-1), 2.40 (s, 3H, NCH$_3$), 2.39-2.15 (m, 5H), 1.81-1.66 (m, 3H).

Step 5: (4R,7S)-2-amino-9-methyl-5,6,7,8-tetrahydro-4H-4,7-epiminocyclohepta-[b]thiophene-3-carbonitrile (6)

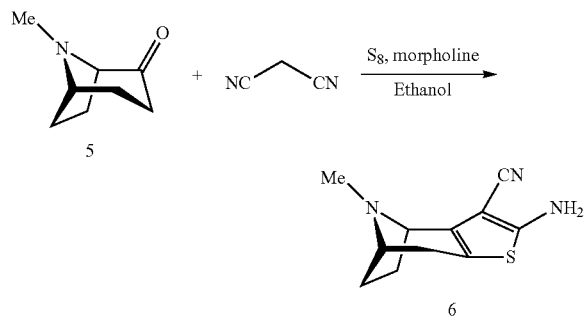

To a mixture of compound 5 (6.5 g, 46.7 mmol), malononitrile (3.39 g, 51.4 mmol) and sulfur (1.64 g, 51.4 mmol) in absolute ethanol (75 mL) in an oven-dried 250 ml round bottom flask at room temperature (20±2° C.) under nitrogen atmosphere was dropped in morpholine (11 mL, 131 mmol) in 5 minutes. After addition was completed, the reaction mixture was heated at 50° C. under nitrogen atmosphere with stirring for 16 hours to give a dark black brown solution. Upon cooling to room temperature (20±2° C.), the reaction mixture was mixed with 25 g of silica gel, concentrated to dryness and purified using Teledyne ISCO Combiflash automatic chromatography system (120 g Redisep silica gel column, eluent with EtOAc in CH$_2$Cl$_2$ gradient) to give 6 (9.01 g, 88%) as a light brown solid; $^1$H-NMR (300 MHz, DMSO-d6) δ 7.02 (s, br, 2H, —NH$_2$), 3.53 (d, J=5.2 Hz, 1H, H-1), 3.36-3.29 (m, 1H, H-5), 2.78 (dd, J=16.2, 4.4 Hz, 1H, H-4$_{ax}$), 2.21 (s, 3H, NCH$_3$), 2.15-1.95 (m, 3H), 1.70-1.61 (m, 1H), 1.50-1.41 (m, 1H); CIMS [M+1]$^+$ 220.

Step 6: (4R,7S)-2-amino-9-methyl-5,6,7,8-tetrahydro-4H-4,7-epiminocyclohepta-[b]thiophene-3-carboxamide (7)

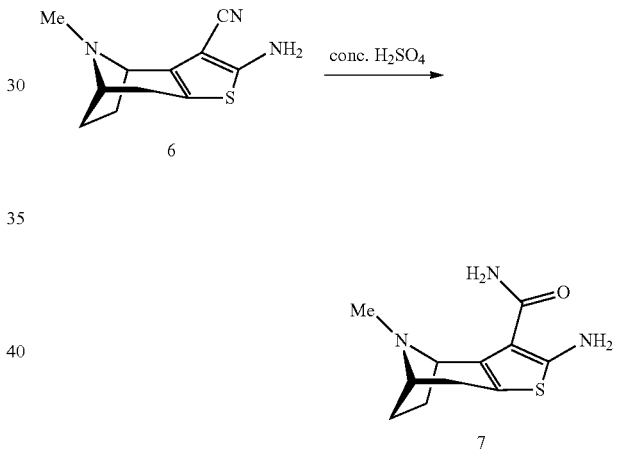

A 250 ml round bottom flask charged with 6 (9.01 g, 41 mmol) and a magnetic stir bar was cooled in an ice-water bath. Conc. sulfuric acid (41 mL) precooled in an ice-water bath was dropped in slowly with stirring to form a dark black brown solution. The reaction solution was stirred at room temperature (20±2° C.) for 40 hours and then cooled in an ice-water bath and slowly added into an ice-water cooled 10% NaOH aqueous solution (450 mL). The resulted aqueous solution was adjusted to pH=10 with 10% NaOH aqueous solution and extracted with methylene dichloride (contain 5-10% methanol, 650 mL×2) and chloroform (contain 5-10% methanol, 650 mL×2). The combined organic extracts were dried over Na$_2$SO$_4$. Filtration and concentration gave 7 (9.36 g, 96%) as a brown solid; $^1$H-NMR (300 MHz, DMSO-d6) δ 6.70 (s, br, 2H, —NH$_2$), 6.50 (s, br, 2H, —CONH$_2$), 4.01 (d, J=5.0 Hz, 1H, H-1), 3.35-3.25 (m, 1H, H-5), 2.84 (dd, J=16.2, 4.4 Hz, 1H, H-4$_{ax}$), 2.20 (s, 3H, NCH$_3$), 2.09-1.97 (m, 3H), 1.79-1.69 (m, 1H), 1.50-1.39 (m, 1H); CIMS [M+1]$^+$ 238.

Step 5/6: (4R,7S)-2-amino-9-methyl-5,6,7,8-tetrahydro-4H-4,7-epiminocyclohepta-[b]thiophene-3-carboxamide (7)

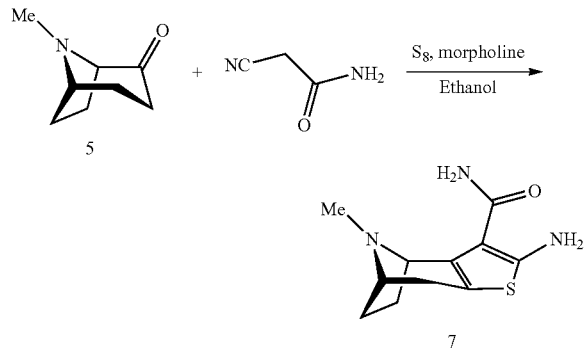

In an alternate procedure, the chemical transformations in Steps 5 and 6 were carried out in a single step. To a mixture of (1R)-2-tropinone (32.0 g, 0.23 mol), 2-cyanoacetamide (21.6 g, 0.25 mol) and sulfur (8.2 g, 0.26 mol) in absolute ethanol (370 mL) in an oven-dried 1000 mL 3-necked roundbottom flask at room temperature (15±2° C.) under nitrogen atmosphere was dropped in morpholine (57.0 g, 0.66 mol) in 20 minutes. After addition was completed, the reaction mixture was heated at 50° C. under nitrogen atmosphere with stirring for 30 hours to give a solution. The reaction was repeated once. Upon cooling to room temperature (15±2° C.), the two batches of reaction mixture was mixed with 180 g of silica gel, concentrated to dryness and purified using Combiflash automatic chromatography system (900 g silica gel column, eluent with MeOH in $CH_2Cl_2$ gradient, 0-10%). The product was slurried with 210 mL of MTBE and collected to afford 7 (89 g, 82%) as a light yellow solid.

Step 7: (4R,7S)-2-(3-(4-chlorophenyl)ureido)-9-methyl-5,6,7,8-tetrahydro-4H-4,7-epiminocyclohepta[b]thiophene-3-carboxamide (8)

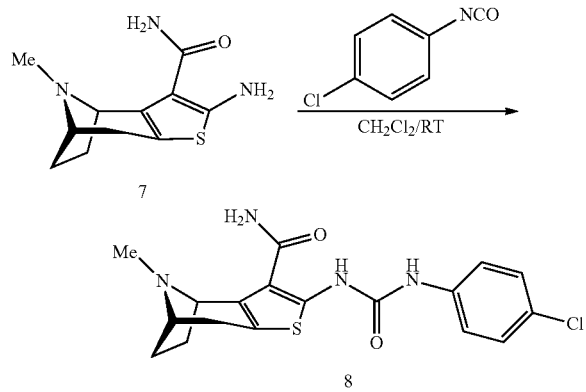

To a mixture of 7 (9.36 g, 39.5 mmol) and anhydrous methylene chloride (360 mL) in a 2 L round bottom flask at room temperature (20±2° C.) under nitrogen atmosphere was dropped in through an addition funnel a solution of 4-chlorophenyl isocyanate (6.67 g, 43.5 mmol) in anhydrous methylene chloride (250 mL) over 20 minutes. After addition was completed, the reaction mixture was stirred under nitrogen atmosphere at room temperature (20±2° C.) for 16 hours. The reaction mixture was mixed with 100 mL methanol and 25 g of silica gel, concentrated to dryness and purified using Teledyne ISCO Combiflash automatic chromatography system (330 g Redisep silica gel column, first eluent with EtOAc in $CH_2Cl_2$ gradient, then with 1% $Et_3N$/ 10% MeOH/89% EtOAc in $CH_2Cl_2$ gradient) to afford 15.8 g light brown solid product that was recrystallized from methanol/hexane to give 8 (10.1 g, 65%) as a slightly yellow to off-white solid: mp 154-156° C.; $[\alpha]^{22}_D$=+19.05 (c=0.2, MeOH); $^1$H-NMR (300 MHz, DMSO-d6) δ 10.70 (s, br, 1H, NH—CO), 10.05 (s, br, 1H, NH—CO), 7.51 (d, J=8.8 Hz, 2H, ArH), 7.31 (d, J=8.8 Hz, 2H, ArH), 7.10 (s, br, 2H, —$CONH_2$), 4.21-4.05 (m, br, 1H, H-1), 3.49-3.30 (m, br, 1H, H-5), 2.99 (d, J=15.3 Hz, 1H, H-4$_{ax}$), 2.39-1.98 (m, 6H), 1.91-1.70 (m, br, 1H), 1.48 (s, br, 1H); CIMS [M+1]$^+$ 391; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 9 min, flow rate: 1 ml/min, column temperature: 20±2° C., detector: λ=254 nm, $t_R$=4.2 min; Chiral HPLC column: Chiralcel OD, mobile phase A: 1% diethylamine in hexane, mobile phase B: 1% diethylamine in ethanol, A:B=1:1 (v/v), flow rate: 0.76 ml/min, column temperature: 20±2° C., detector: λ=254 nm, $t_R$=15.3 min>99%.

Step 8: (4R,7S)-2-(3-(4-chlorophenyl)ureido)-9-methyl-5,6,7,8-tetrahydro-4H-4,7-epiminocyclohepta[b]thiophene-3-carboxamide hydrochloride (9)

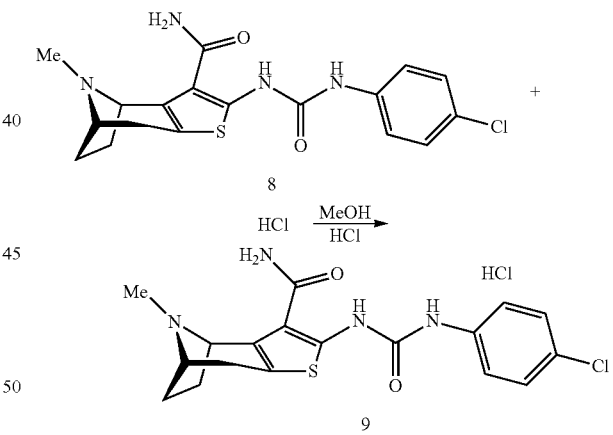

A solution of 8 (16.8 g, 43 mmol) in methanol (1.5 L) in a 3 L round bottom flask was cooled in an ice-water bath. White precipitates appeared. While stirring, 1 N HCl (64 mL) was dropped in over 5 minutes and the system gradually turned into a clear solution. After addition was completed, the solution was stirred at room temperature (20±2° C.) for 15 minutes and diluted with water (450 mL). All the methanol was evaporated under reduced pressure and the residue was mixed with water (450 mL) and lyophilized to give the title compound (9) (18.0 g) as an off-white solid: mp 200-202° C.; $[\alpha]^{22}_D$=+4.65 (c=0.2, MeOH); $^1$H-NMR (300 MHz, DMSO-d6) δ 11.22 (s, br, 0.31H, —NH), 10.33 (s, 0.63H, NH—CO), 10.31 (s, 0.37H, NH—CO), 10.18 (s, 0.63H, NH—CO), 10.17 (s, br, 0.61H, —NH), 10.15 (s, 0.37H, NH—CO), 7.49 (dd, J=9.0, 2.2 Hz, 2H, ArH), 7.45 (s, br, 2H, —CONH$_2$), 7.35 (dd, J=9.0, 2.2 Hz, 2H, ArH), 4.93-4.87 (m, br, 1H, H-1), 4.21-4.15 (m, br, 0.63H, H-5), 4.15-4.05 (m, br, 0.37H, H-5), 3.38 (dd, J=16.5, 4.1 Hz, 0.61H, H-4$_{ax}$), 3.20 (dd, J=18.4, 4.9 Hz, 0.39H, H-4$_{ax}$), 2.89-2.76 (m, 1H, H-4 eq), 2.80 (d, J=4.9 Hz, 2H, NCH$_3$), 2.69 (d, J=4.9 Hz, 1H, NCH$_3$), 2.49-2.22 (m, 2H), 2.21-2.06 (m, 1H), 1.92-1.76 (m, 1H); $^{13}$C-NMR (75 MHz, DMSO-d6) δ 166.3 (0.4C), 166.2 (0.6C), 151.9, 145.6 (0.4C), 145.5 (0.6C), 138.8, 132.0 (0.6C), 129.3 (2C), 128.0 (0.4C), 126.5, 120.8, 120.3 (2C), 114.1 (0.4C), 113.3 (0.6C), 62.5 (0.6C), 62.1 (0.6C), 60.2 (0.4C), 58.2 (0.4C), 33.8 (0.4C), 32.6 (0.6C), 32.4 (0.6C), 31.2 (0.4C), 28.1 (0.6C), 27.6 (0.6C), 25.8 (0.8C); CIMS [M+1]$^+$ 391; Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 9 min, flow rate: 1 ml/min, column temperature: 20±2° C., detector: λ=254 nm, t$_R$=4.2 min; Chiral HPLC column: Chiralcel OD, mobile phase A: 1% diethylamine in hexane, mobile phase B: 1% diethylamine in ethanol, A:B=1:1 (v/v), flow rate: 0.76 ml/min, column temperature: 20±2° C., detector: λ=254 nm, t$_R$=15.3 min>99%; Anal. Calcd for C$_{18}$H$_{20}$Cl$_2$N$_4$O$_2$S.2H$_2$O: C, 46.66; H, 5.22; N, 12.09. Found C, 46.67; H, 5.15; N, 12.14.

The N-methyl group of compound 9 exists in both a pseudo equatorial and pseudo axial orientation. This gives rise to duplicate $^1$H-NMR resonances for the methyl group as well as other affected protons. These effects are also observed in the $^{13}$C-NMR spectrum. The H and C resonances are therefore reported as fractional values.

Example 2: Preparation of (4R,7S)-2-(3-(4-chlorophenyl)ureido)-5,6,7,8-tetrahydro-4H-4,7-epiminocyclohepta[b]thiophene-3-carboxamide hydrochloride (10)

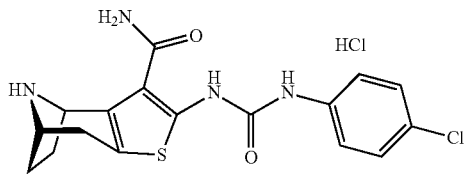

10

The title compound (10) is prepared in a similar manner as described in Example 1.

Example 3: Preparation of (4R,7S)-2-[3-(4-chlorophenyl)ureido]-5,8-dimethyl-5,6,7,8-tetrahydro-4H-4,7-epiminocyclohepta[b]thiophene-3-carboxamide hydrochloride (11)

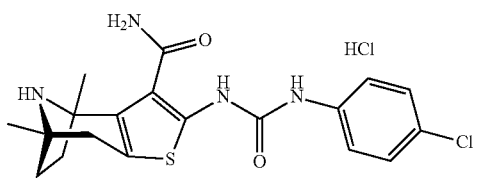

11

The title compound (11) is prepared in a similar manner as described in Example 1.

Example 4: Preparation of (4R,7S)-2-[3-(4-benzoylphenyl)ureido]-9-methyl-5,6,7,8-tetrahydro-4H-4,7-epiminocyclohepta[b]thiophene-3-carboxamide hydrochloride (12)

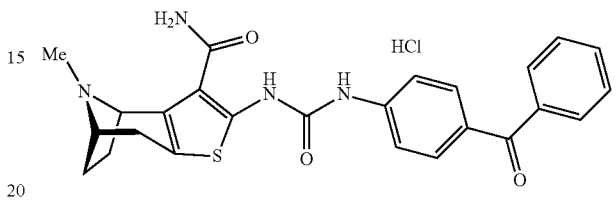

12

The title compound (12) is prepared in a similar manner as described in Example 1.

Example 5: Preparation of (4R,7S)-2-[3-(4-chlorophenyl)ureido]-9-(cyclohexylmethyl)-5,6,7,8-tetrahydro-4H-4,7-epiminocyclohepta[b]thiophene-3-carboxamide hydrochloride (13)

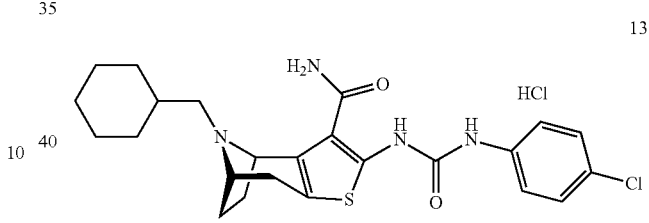

13

The title compound (13) is prepared in a similar manner as described in Example 1.

Example 6: Preparation of (4R,7S)-2-[3-(4-chlorophenyl)ureido]-9-(cyclobutylmethyl)-5,6,7,8-tetrahydro-4H-4,7-epiminocyclohepta[b]thiophene-3-carboxamide hydrochloride (14)

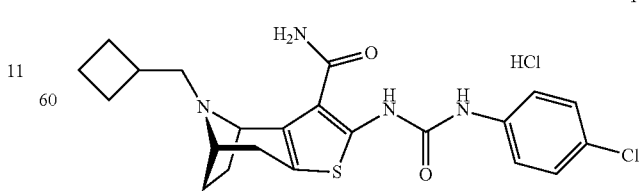

14

The title compound (14) is prepared in a similar manner as described in Example 1.

Example 7: Preparation of (4R,7S)-2-[3-(4-chlorophenyl)ureido]-9-ethyl-5,6,7,8-tetrahydro-4H-4,7-epiminocyclohepta[b]thiophene-3-carboxamide hydrochloride (15)

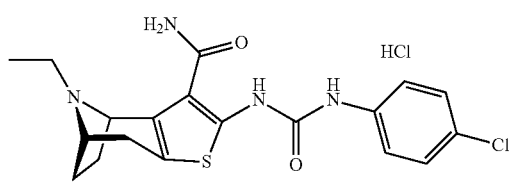

15

The title compound (15) is prepared in a similar manner as described in Example 1.

Example 8: Preparation of (4R,7S)-Methyl 3-{3-carbamoyl-2-[3-(4-chlorophenyl)ureido]-5,6,7,8-tetrahydro-4H-4,7-epiminocyclohepta[b]thiophen-9-yl}-2,2-dimethylpropanoate hydrochloride (16)

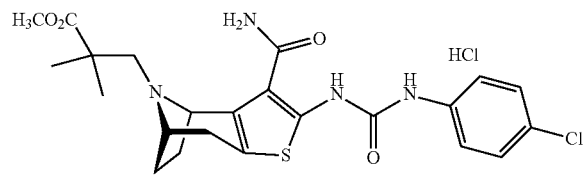

16

The title compound (16) is prepared in a similar manner as described in Example 1.

Example 9: Preparation of (4R,7S)-3-carbamoyl-2-[3-(4-chlorophenyl)ureido]-9,9-dimethyl-5,6,7,8-tetrahydro-4H-thienocyclohepten-4,7-iminium iodide (17)

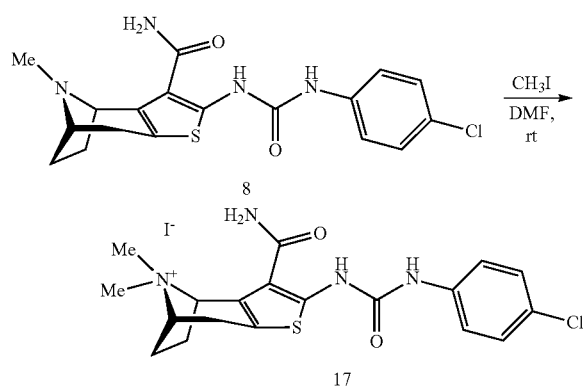

A solution of compound 8 and iodomethane (1.3 equivalents) in N,N-dimethylformamide is stirred at room temperature for 18 h. The reaction mixture is then concentrated under reduced pressure. The resulting residue is triturated with methylene chloride to give compound 17.

Example 10: Preparation of (4R,7S)-3-carbamoyl-2-[3-(4-chlorophenyl)ureido]-9-ethyl-9-methyl-5,6,7,8-tetrahydro-4H-thienocyclohepten-4,7-iminium iodide (18)

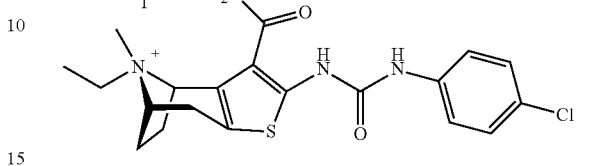

18

The title compound (18) is prepared in a similar manner as described in Example 9.

Example 11: Preparation of (4R,7S)-3-carbamoyl-2-[3-(4-chlorophenyl)ureido]-9-(cyclobutylmethyl)-9-methyl-5,6,7,8-tetrahydro-4H-thienocyclohepten-4,7-iminium iodide (19)

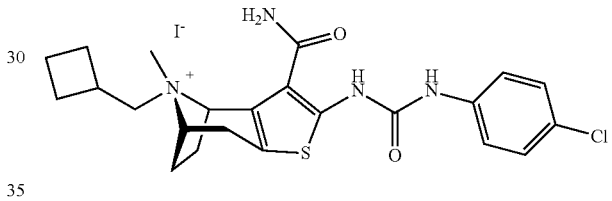

19

The title compound (19) is prepared in a similar manner as described in Example 9.

Biological Assays

Example 12: Neomycin Hair Cell Toxicity Assay in Zebrafish

Zebrafish are bred and newly fertilized embryos are collected the week prior and raised at 28.5° C. in petri dishes containing embryo medium. Newly hatched free-swimming larvae are fed paramecium and dry fish food at 4 days post fertilization (dpf) with lights on. For treatment, fish 5-7 dpf are transferred to cell culture baskets and place within a well of a 6-well plate containing 7 milliliters of 1× embryo medium. Typically, tests are done with ten fish per basket but work well with up to 50 fish. All treatment and wash volumes are 7 milliliters.

1. Fish are pre-treated with test compound for 1 hour. Concentrations between 0.010 to 25 micromolar of test compound are tested.
2. Treat with 200 micromolar neomycin (neomycin sulfate, Sigma, St. Louis, Mo., catalog #N1142)+ test compound for 30 minutes.
3. Rinse fish briefly 4 times in embryo medium and add 700 µl of 0.05% DASPEI (2-{4-(dimethylamino)styryl}-N-ethylpyridinium iodide, Molecular Probes, Eugene, Oreg.) and allowed to stain for 15 minutes.
4. Rinse twice in embryo medium and add 350 µL MS222 (0.55 ug/ml final concentration, 3-aminobenzoic acid ethyl ester, methansulfoneate salt, Sigma, St. Louis, Mo.) to anesthetize.

5. View with epifluorescence dissecting microscope equipped with a DASPEI filter set (excitation 450-490 nM and barrier 515 nM, Chroma Technologies, Brattleboro, Vt.). For assessment of initial dose response curves, fish are transferred to wide depression slide with wide-bore pipette. The DASPEI staining of ten neuromasts (SO1, SO2, IO1, IO2, IO3, IO4, M2, MI1, MI2 and O2) on one side of an animal are evaluated. Each neuromast is scored for presence of DASPEI staining (score=2), reduced DASPEI staining (score=1) or absence of DASPEI staining (score=0). Total scores for an animal are tabulated, to give a composite score that can range from 0 to 20. Average scores and standard deviations are calculated for animals in each treatment group. Scores are normalized to control group (vehicle only, no drug, no neomycin) and expressed as % hair cell survival. HCmax is the maximum protection (hair cell survival) observed. 6. If at least 50% hair cells survive, the HC50 (concentration that would produce 50% hair cell survival) is calculated as a linear extrapolation from the nearest concentrations of protective drug that produce hair cell survival below and above 50%. If less than 50% hair cells survive, the HC50 is not determined.

1× embryo media (standard lab EM):
1 mM $MgSO_4$,
0.15 mM $KH_2PO_4$,
0.05 mM $Na_2HPO_4$,
1 mM $CaCl_2$,
0.5 mM KCl
15 mM NaCl
0.7 mM $NaHCO_3$ The results for compound 9 in the Neomycin Hair Cell Toxicity Assay are shown in Table 1.

TABLE 1

| Compound | $HC_{50}$ | Max HC Protection |
| --- | --- | --- |
| 9 | <1.0 µM | 96% protection at 2.6 µM |

Example 13: Cisplatin Hair Cell Toxicity Assay in Zebrafish

Zebrafish are bred and newly fertilized embryos are collected the week prior and raised at 28.5° C. in petri dishes containing embryo medium. Newly hatched free-swimming larvae are fed paramecium and dry fish food at 4 days post fertilization (dpf) with lights on. For treatment, fish 5-7 dpf are transferred to cell culture baskets and place within a well of a 6-well plate containing 7 milliliters of 1× embryo medium. Typically, tests are done with ten fish per basket but work well with up to 50 fish. All treatment and wash volumes are 7 milliliters.

1. In a 48-well plate, place 10-12 fish/well in 300 µl of EM.
2. Add ORC-13661 and vehicle control to each well at concentrations listed below. Swirl and place in incubator for 15 min. ORC-13661 concentrations tested: 0.103 µM, 0.308 µM, 0.925 µM, 2.78 µM, 8.33 µM.
3. Add cisplatin 50 µM to pretreated and control wells. Swirl and place in incubator for 24 hrs.
4. Place 1-2 drops of MS222 in each well to anesthetize fish, then aspirate treated EM.
5. Add 300 µl/well of 4% paraformaldehyde to fix fish. Fix overnight at 4° C. or 2 hrs at room temperature (RT).
6. Rinse wells with PBS for 15 min each 3 times.
7. Add 300 µl/well of blocking solution for 1 hr at RT.
8. Incubate with 300 µl/well of 1:400 mouse anti-Parvalbumin antibody overnight at 4° C.
9. Rinse wells with PBS-T for 15 min each 3 times.
10. Incubate with 300 µl/well of 1:500 Alexa 488 goat anti-mouse secondary antibody for 2-4 hrs at RT.
11. Rinse wells with PBS-T for 15 min each 3 times.
12. Rinse wells with PBS for 15 min each 3 times.
13. Mount each group of fish on coverslips with Fluoromount G. Image on Zeiss Axioplan at 40× magnification with GFP filter and count number of hair cells in 4 neuromasts: SO1, SO2, O1, OC1.
14. Average the total number of hair cells from the 4 neuromasts per fish in each treatment group and normalize to vehicle control group to get hair cell counts as % control+/− standard deviation.

The results for compound 9 in the Cisplatin Hair Cell Toxicity Assay are shown in Table 2 and FIG. 1.

TABLE 2

| Compound | $HC_{50}$ | Max HC Protection |
| --- | --- | --- |
| 9 | <1.0 µM | 90% protection at 8.33 µM |

Example 14: Auditory Brainstem Response (ABR) Assay

Chronic treatment of rats with aminoglycosides (AGs) such as kanamycin or amikacin results in an elevation of ABR thresholds, typically most pronounced at higher frequencies. For rats, hearing is tested at a range of frequencies to determine the intensity of sound (measured in decibels) necessary to evoke a response. As hearing loss becomes more severe, a higher intensity is needed to evoke a response. Each rat serves as its own control; hearing thresholds are determined at each frequency prior to any treatment and then at 2 weeks after a 10-day course of AG treatment (or control drug exposures).

The ABR assay measures short latency field potentials recorded from the scalp of animals that were sedated or noninvasively immobilized. A series of 10-1000 clicks or pure tone pulses were presented to the animal at a rapid rate, resulting in a stereotyped series of waveforms reflecting the electrical events in brain stem auditory regions. For each animal, hearing thresholds, wave 1 latencies and input-output functions for stimulus frequencies at 2, 4, 8, 16 and 32 kHz were measured prior to any treatment to determine the initial sensitivity and dynamic range of hearing, and then repeated at the end of drug treatment and at the end of the experiment (2-weeks after dosing).

Treatment Groups:
Amikacin (SC) @ 320 mg/kg/day for 10 days; n=13 (hereafter "AMI/320")
AMI/320+ Compound 9 (PO) @ 5 mg/kg/day for 10 days n=7
Compound 9 alone @ 5 mg/kg/day for 10 days; n=5
Vehicle of Compound 9 (IP) for 10 days; n=6.

Figure 2:
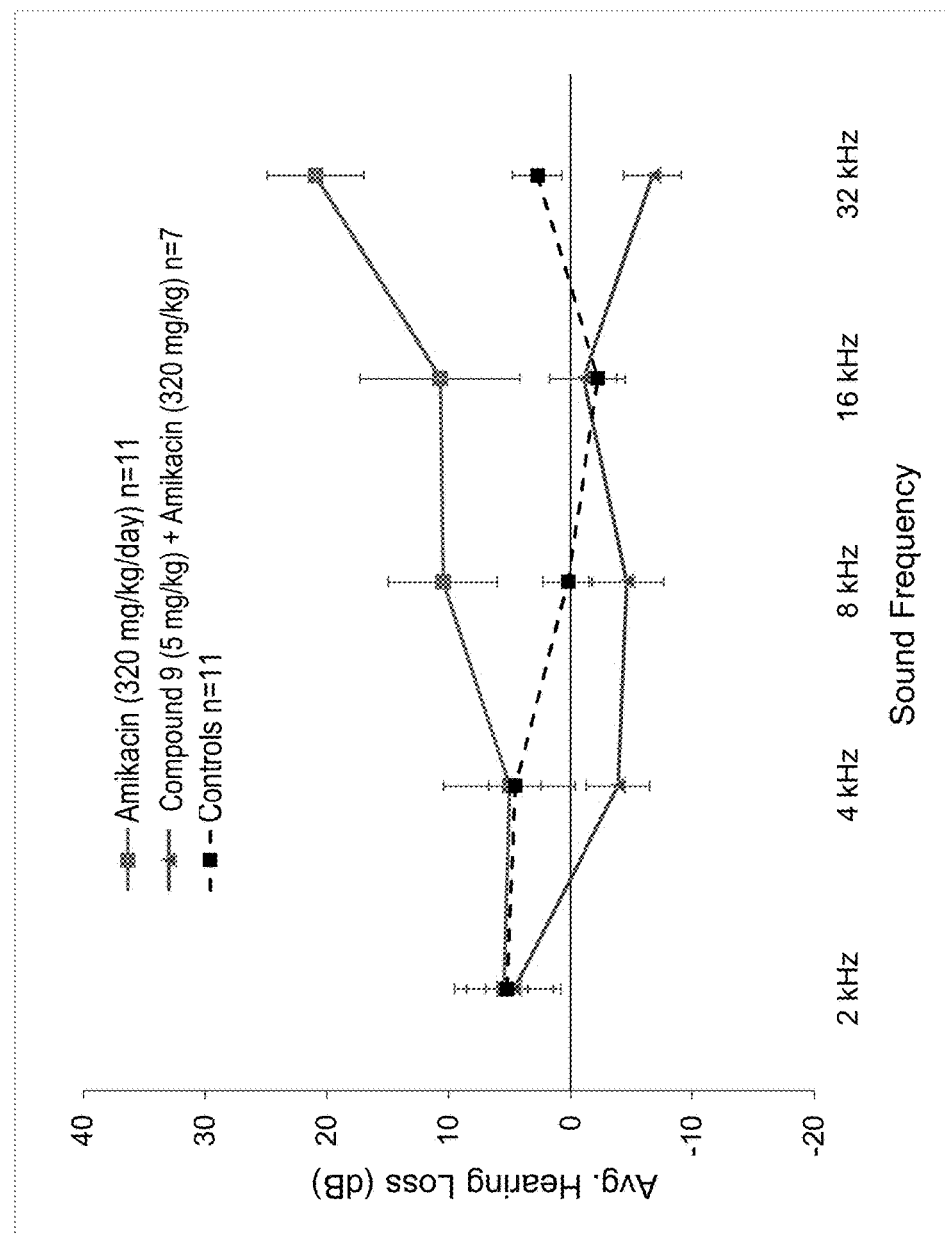
FIG. 2 shows high frequency hearing loss in rats following treatment with amikacin alone or amikacin plus compound 9.

ABR records were evaluated by a "blinded", trained experimenter. Hearing loss (Threshold Shift) was determined by subtracting the threshold during pre-treatment (Day 0) from the final ABR threshold (Day 24; two weeks following treatment). Within the variation of the test, a positive value means that the rat suffered hearing loss during the exposure period. This was seen in the animals treated with amikacin alone (FIG. 2). Co-administration of Compound 9 led to robust protection of the high frequency loss due to Amikacin exposure (FIG. 2). Animals in the control groups showed no significant change in threshold at any frequency over the study period (FIG. 2).

Example 15: Effect of Amikacin and Compound 9 on Kidney Function

The study consisted of three groups of Fischer 344 rats aged 6 weeks and weighing approximately 200 g at the start of the study. Group 1 consisted of six rats, randomly selected to receive amikacin only, Group 2 consisted of six rats chosen randomly to receive amikacin and compound 9, and Group 3 consisted of three rats, 2 rats given compound 9 and 1 rat given only 0.5% Methylcellulose, the diluent for compound 9. All animals receiving amikacin were given 320 mg/kg subcutaneously (SQ) from a freshly prepared solution of amikacin of 40 mg/mL. The compound 9 formualtion was prepared by weighing 13.08 mg of compound 9 dissolved in 12 mL of 0.5% MC in saline with vortexing, sonification and homogenization to obtain a solution with concentration at 12 mg/12 mL=1 mg/mL, dose volume is 5 mL/kg (5 mg/kg). The compound 9 solution was given by oral gavage at a dose of 5 mg/kg.

One day prior to the onset of dosing, blood was drawn from all rats for serum analysis and all rats were put into metabolic cages for 24 hour urine collection and analysis. All rats were returned to normal cages and allowed to eat and drink ad lib. All rats received their assigned treatments for 10 days and then were returned to metabolic cages for the $10^{th}$ day. Three rats were randomly chosen from each of Group 1 and Group 2 to have additional blood draws at 30 min, 60 mn, 2 hr, 4 hr, 8 hr and 24 hr after the $10^{th}$ dose for amikacin and compound 9 PK analysis. All rats had blood drawn for serum analysis at the end of day 10 and the 24 hour urine collected from day 10. After the final blood draw, all rats were euthanized and their kidneys removed and prepared for histopathology testing. The left kidneys were longitudinally sectioned, the right kidneys were cross sectioned. The pathologist read the slides, blinded to the group from which they were assigned. They graded viewed five different locations on each slide and gave each location a score for degree of damage: no damage (0 score); minimal (1-10%, 1 score), mild (11-20%, 2 score), moderate (21-50%, 3 score), or marked (51-100%, 4 score).

Figure 3:
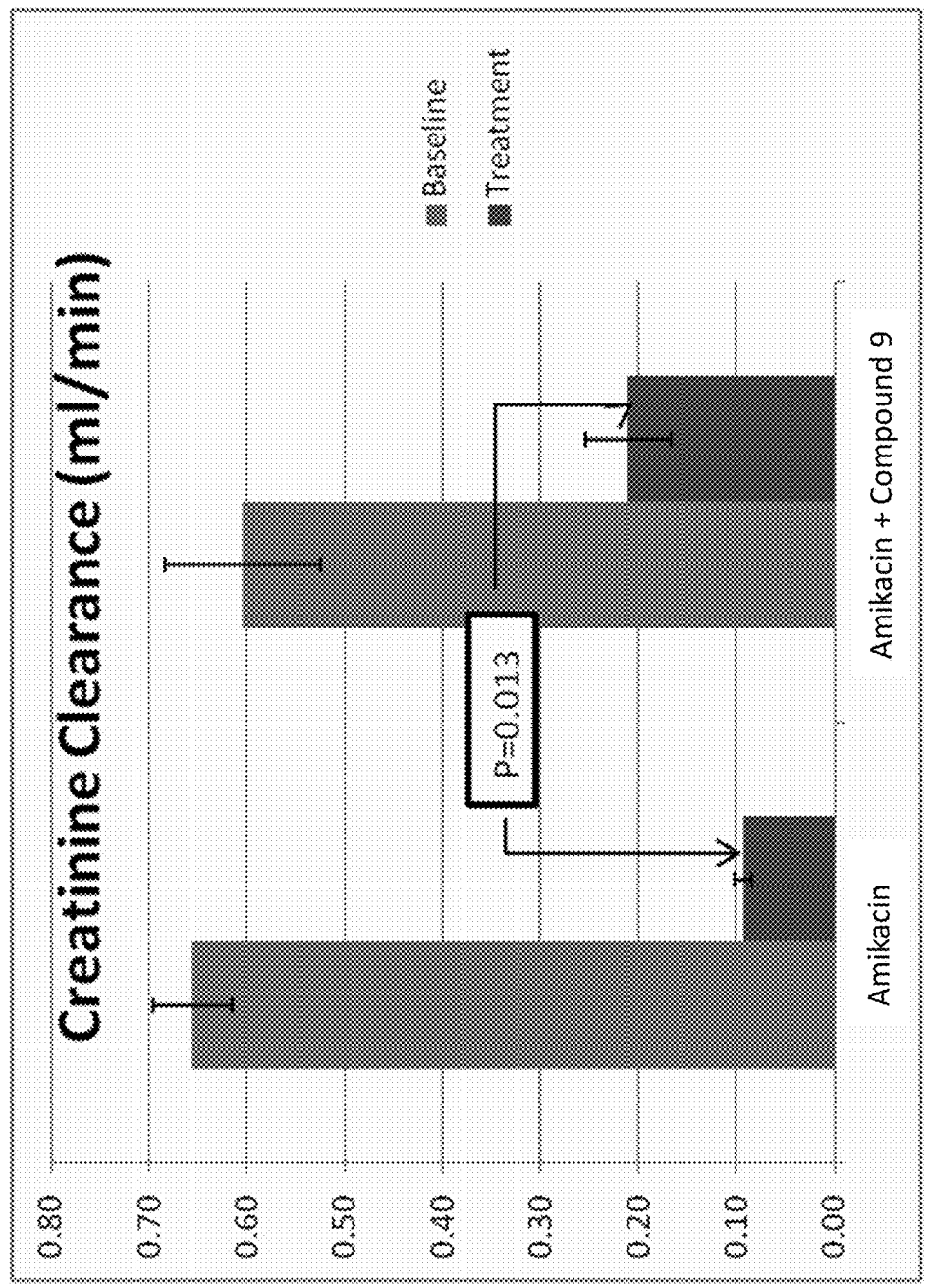
FIG. 3 shows creatinine clearance in rats following treatment with amikacin alone or amikacin plus compound 9.

Previous studies have shown that aminoglycoside renal toxicity primarily affects the proximal and distal tubules of the kidney, eventually causing apotheosis of the epithelial cells. The resulting damage causes, in part, decreased glomerular filtration rate (GFR) which may be a result of the tubular damage or partly through other mechanisms. The GFR was approximated using the creatinine clearance. The first objective of this experiment was to demonstrate that amikacin given at 320 mg/kg/day for 10 days was sufficient to cause significant nephrotoxicity measured by a reduction in creatinene clearance; and second that rats treated with amikacin plus compound 9 have significantly less renal toxicity measured by an increase in creatinine clearance relative to amikacin only rats. FIG. 3 shows the the mean and standard error of the mean of the creatinine clearance (CrCl) in rats from Group 1 and 2 post-treatment compared to their pretreatment values. The one-sided two-sample t-test p-value for the comparison of the amikacin only (Group 1) and amikacin+compound 9 (Group 2) are shown in a box between the two columns. Both Group 1 and Group 2 animals post treatment are significantly different from baseline and these significance levels are not shown.

Figure 4:
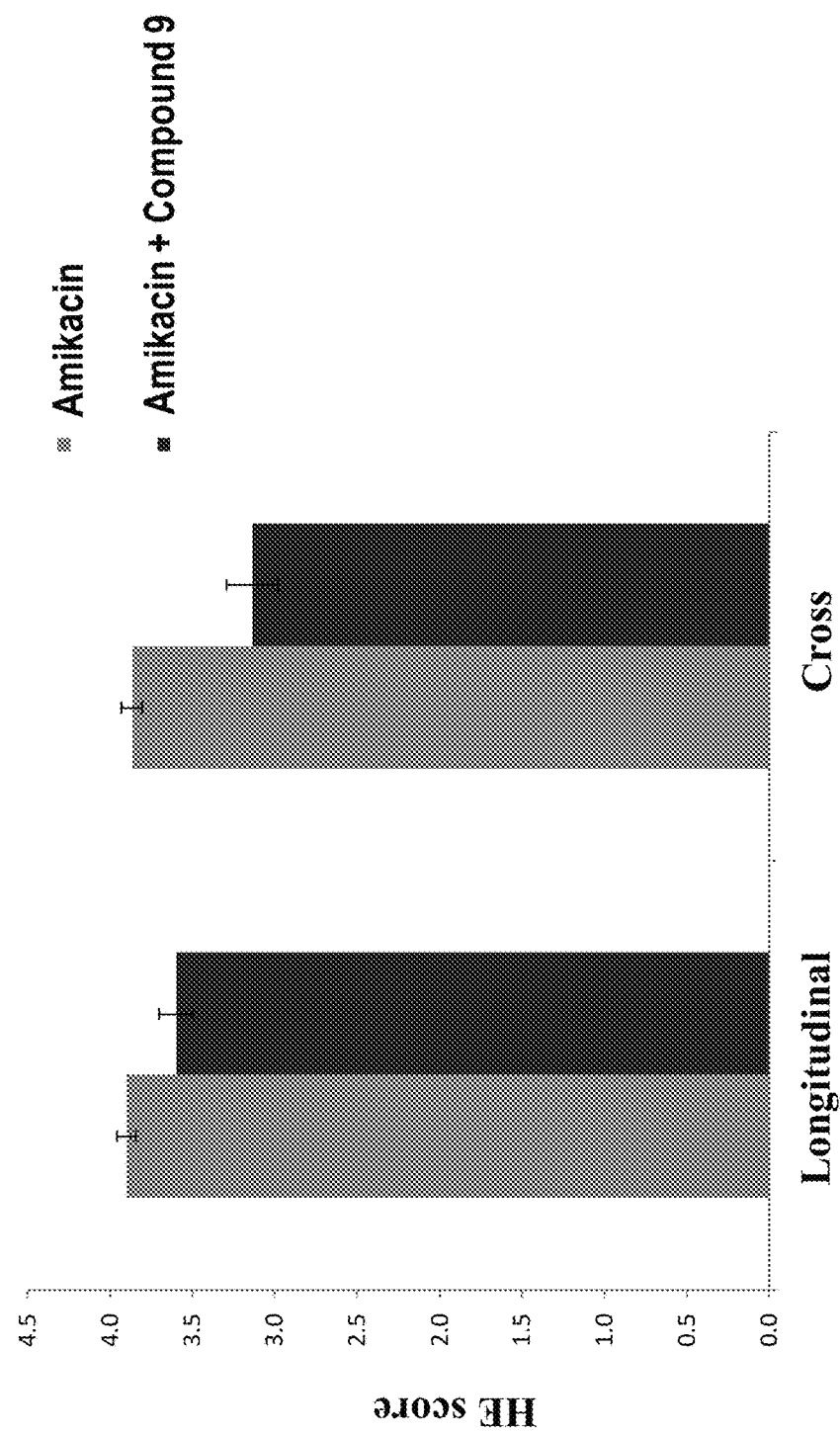
FIG. 4 shows histopathology data in rat kidney following treatment with amikacin alone or amikacin plus compound 9.

FIG. 4 shows the results of the histopathology of amikacin only rats versus that of the amikacin+compound 9 treated rats for each the longitudinal sectioning of the kidney and the cross sectioning of the kidney. Although the differences are not great numerically, they are significant at p<0.005 level. A 4 means close to 100% damage, while a 3 means <50% damage, so a change of 3.9 to 3.6 is meaningful and a change of 3.9 to 3.1 may mean an improvement of as much as 50% in the damage caused.

Example 16: Clinical Trial of the Protective Effect of a Compound of Formula (I), (Ia), (Ib), (II), (IIa), or (IIb) Against Ototoxicity The majority of patients with Cystic Fibrosis that live to adulthood have periodic bouts of pulmonary *pseudomonas* infections severe enough to warrant parenteral aminoglycoside therapy despite their potential risk for ototoxicity. At least 20% of adult cystic fibrosis patients have definite measurable hearing loss, especially in the higher frequencies as measured by standard and high frequency audiometric tests. Renal toxicity is another frequent unwanted side effect occurring in as many as 7% of the patients treated with aminoglycosides. The purpose of this study is to examine whether ototoxicity and renal toxicity due to parenteral aminoglycosides therapy for *pseudomonas* infections in patients with cystic fibrosis can be prevented by a compound of Formula (I), (Ia), (Ib), (II), (IIa), or (IIb).

Patients: Eligible subjects will be men and women 18-65 years of age.

Inclusion Criteria
    Definitive diagnosis of Cystic Fibrosis
    Scheduled for hospital or ambulatory intravenous treatment of pulmonary pseudomonas infections using only an aminoglycoside antibiotic
    Has normal or near normal renal function Exclusion Criteria
    Has been treated with parenteral aminoglycoside antibiotics within the previous 3 months
    Detection of mechanical occlusion of external ear
    Having signs of disturbed integrity of tympanic membrane on otoscopy or tympanometry
    Has >20 db hearing loss at all frequencies below 8 khtz Study Design:

| Arms |
| --- |
| Experimental: Compound of Formula (I), (Ia), (Ib), (II), (IIa), or (IIb) |
| Compound of Formula (I), (Ia), (Ib), (II), (IIa), or (IIb) 5 mg/kg po daily + amikacin or tobramycin |
| Tobramycin or amikacin alone |

Primary Outcome Measures
    Compare threshold hearing levels change from before therapy to 4 weeks following the completion of therapy between the two arms using standard and high frequency audiometric tests.
    Compare changes in creatinine clearance, urine Kim-1, serum creatinine and Bun from before therapy to the day following the completion of therapy between the two arms.

What is claimed is:

1. A method for preventing and/or protecting against sensory hair cell death associated with exposure to an ototoxic agent in an individual comprising administering to the individual a therapeutically effective amount of:

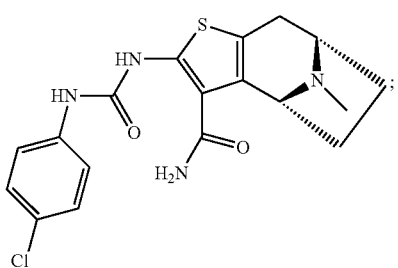

or a pharmaceutically acceptable salt thereof.

2. The method of claim 1, wherein the ototoxic agent is an aminoglycoside antibiotic, chemotherapeutic agent, loop diuretic, antimalarial sesquiterpene lactone endoperoxide, antimalarial quinine, salicylate, or interferon polypeptide.

3. The method of claim 2, wherein the ototoxic agent is an aminoglycoside antibiotic.

4. The method of claim 3, wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin.

5. The method of claim 4, wherein the aminoglycoside antibiotic is streptomycin.

6. The method of claim 4, wherein the aminoglycoside antibiotic is neomycin.

7. The method of claim 4, wherein the aminoglycoside antibiotic is amikacin.

8. The method of claim 2, wherein the ototoxic agent is a chemotherapeutic agent.

9. The method of claim 8, wherein the chemotherapeutic agent is cisplatin or carboplatin.

* * * * *